US012565517B2

(12) United States Patent
Kojoh et al.

(10) Patent No.: US 12,565,517 B2
(45) Date of Patent: Mar. 3, 2026

(54) CYCLIC PEPTIDE HAVING CTLA-4 INHIBITORY ACTIVITY AND USE THEREOF

(71) Applicant: GeneFrontier Corporation, Kashiwa (JP)

(72) Inventors: Kanehisa Kojoh, Kashiwa (JP); Kumiko Tsuihiji, Kashiwa (JP); Shizue Katoh, Kashiwa (JP); Mikiko Nakamura, Kashiwa (JP)

(73) Assignee: GeneFrontier Corporation, Kashiwa (JP)

( * ) Notice: Subject to any disclaimer, the term of this patent is extended or adjusted under 35 U.S.C. 154(b) by 974 days.

(21) Appl. No.: 17/767,550

(22) PCT Filed: Sep. 30, 2020

(86) PCT No.: PCT/JP2020/037100

§ 371 (c)(1),
(2) Date: Apr. 8, 2022

(87) PCT Pub. No.: WO2021/070696

PCT Pub. Date: Apr. 15, 2021

(65) Prior Publication Data

US 2024/0092836 A1 Mar. 21, 2024

(30) Foreign Application Priority Data

Oct. 8, 2019 (JP) ................................ 2019-185266

(51) Int. Cl.
*C07K 7/64* (2006.01)

(52) U.S. Cl.
CPC ..................................... *C07K 7/64* (2013.01)

(58) Field of Classification Search
None
See application file for complete search history.

(56) References Cited

U.S. PATENT DOCUMENTS

| | | | |
|---|---|---|---|
| 6,084,067 | A | 7/2000 | Freeman et al. |
| 2012/0231496 | A1 | 9/2012 | Kanamori et al. |
| 2014/0051645 | A1 | 2/2014 | Matschiner et al. |
| 2016/0304580 | A1 | 10/2016 | Ellmark et al. |
| 2018/0117084 | A1 | 5/2018 | Halpert et al. |
| 2019/0169600 | A1 | 6/2019 | Kita et al. |

FOREIGN PATENT DOCUMENTS

| | | | |
|---|---|---|---|
| JP | 2008-271903 | A | 11/2008 |
| JP | 2009-060905 | A | 3/2009 |
| JP | 2016-526885 | A | 9/2016 |
| JP | 2018-519255 | A | 7/2018 |
| WO | WO 2017/213158 | A1 | 12/2017 |

OTHER PUBLICATIONS

Costello et al. (Pancreat Disord Ther; Suppl 4; doi:10.4172/2165-7092.S4-002) (Year: 2013).*
Bashiruddin et al., "Construction and screening of vast libraries of natural product-like macrocyclic peptides using in vitro display technologies," *Curr. Opin. Chem. Biol.*, 24: 131-138 (2015).
Desimmie et al., "Phage Display-directed Discovery of LEDGF/p75 Binding Cyclic Peptide Inhibitors of HIV Replication," *Mol. Ther.*, 20(11): 2064-2075 (2012).
Guillen Schlippe et al., "In Vitro Selection of Highly Modified Cyclic Peptides That Act as Tight Binding Inhibitors," *J. Am. Chem. Soc.*, 134(25): 10469-10477 (2012).
Leach et al., "Enhancement of Antitumor Immunity by CTLA-4 Blockade," *Science*, 271(5256): 1734-1736 (1996).
Roxin et al., " Flexible or fixed: a comparative review of linear and cyclic cancer-targeting peptides," *Future Med. Chem.*, 4(12): 1601-1618 (2012).
Tavassoli, "SICLOPPS cyclic peptide libraries in drug discovery," *Curr. Opin. Chem. Biol.*, 38: 30-35 (2017).
Zorzi et al., "Cyclic peptide therapeutics: past, present and future," *Curr. Opin. Chem. Biol.*, 38: 24-29 (2017).
Japanese Patent Office, International Search Report in International Patent Application No. PCT/JP2020/037100 (Dec. 15, 2020).
ADIS R&D Profile, "Ipilimumab," Drugs R.D., 10(2): 97-110 (2010).
Amano et al., "Pharmacological Properties and Clinical Efficacy of Ipilimumab, Human Anti-Human CTLA-4 Monoclonal Antibody (YERVOY®)," Folia Pharmacol. Jpn., 147: 243-252 (2016).
Bristol-Myers Squibb Company, U.S. Food & Drug Administration (FDA) Label Information for "YERVOY® (ipilimumab) injection, for Intravenous Use," Reference ID 4494966 (2019).

* cited by examiner

*Primary Examiner* — Sergio Coffa
(74) *Attorney, Agent, or Firm* — Leydig, Voit & Mayer, Ltd.

(57) ABSTRACT

The present invention provides a cyclic peptide which comprises the amino acid sequence represented by formula (I)

$$X_1\text{-His-Pro-}X_4\text{-Leu-}X_6\text{-}X_7\text{-}X_8\text{-Ser-}X_{10}\text{-His-Phe} \quad (I)$$

in the cycle and has an activity to specifically bind to human CTLA-4, wherein $X_1$, $X_4$, $X_6$, $X_7$, $X_8$ and $X_{10}$ are each independently any amino acid.

16 Claims, 3 Drawing Sheets

Specification includes a Sequence Listing.

SEQUENCE LISTING

```
<160> NUMBER OF SEQ ID NOS: 221

<210> SEQ ID NO 1
<211> LENGTH: 223
<212> TYPE: PRT
<213> ORGANISM: Homo sapiens

<400> SEQUENCE: 1

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220


<210> SEQ ID NO 2
<211> LENGTH: 288
<212> TYPE: PRT
<213> ORGANISM: Homo sapiens

<400> SEQUENCE: 2

Met Gly His Thr Arg Arg Gln Gly Thr Ser Pro Ser Lys Cys Pro Tyr
1               5                   10                  15
```

```
Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
        275                 280                 285
```

<210> SEQ ID NO 3
<211> LENGTH: 108
<212> TYPE: DNA
<213> ORGANISM: Artificial Sequence
<220> FEATURE:
<223> OTHER INFORMATION: Oligo DNA encoding randomized amino acid sequence
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)

<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (64)..(65)
<223> OTHER INFORMATION: n is a, c, g, or t
<220> FEATURE:
<221> NAME/KEY: misc_feature
<222> LOCATION: (67)..(68)
<223> OTHER INFORMATION: n is a, c, g, or t

<400> SEQUENCE: 3
gactataaag atgacgatga caaaggcggg tgcnnsnnsn nsnnsnnsnn snnsnnsnns 60
nnsnnsnnst gtggaggcga gcagaagctg atctctgagg aggatctg 108

<210> SEQ ID NO 4
<211> LENGTH: 36
<212> TYPE: PRT
<213> ORGANISM: Artificial Sequence
<220> FEATURE:
<223> OTHER INFORMATION: cyclic peptide with randomized amino acid
sequence
<220> FEATURE:
<221> NAME/KEY: misc_feature
<222> LOCATION: (12)..(23)
<223> OTHER INFORMATION: Xaa can be any naturally occurring amino acid

<400> SEQUENCE: 4

Asp Tyr Lys Asp Asp Asp Asp Lys Gly Gly Cys Xaa Xaa Xaa Xaa Xaa
1               5                   10                  15

Xaa Xaa Xaa Xaa Xaa Xaa Xaa Cys Gly Gly Glu Gln Lys Leu Ile Ser
            20                  25                  30

Glu Glu Asp Leu
        35

<210> SEQ ID NO 5
<211> LENGTH: 112
<212> TYPE: DNA
<213> ORGANISM: Artificial Sequence
<220> FEATURE:
<223> OTHER INFORMATION: 5'UTR Oligo DNA

<400> SEQUENCE: 5
gaaattaata cgactcacta tagggagacc acaacggttt ccctctagaa ataattttgt 60
ttaactttaa gaaggagata taccaatgga ctataaagat gacgatgaca aa 112

<210> SEQ ID NO 6
<211> LENGTH: 60
<212> TYPE: DNA
<213> ORGANISM: Artificial Sequence
<220> FEATURE:
<223> OTHER INFORMATION: Primer Myc-g3p

<400> SEQUENCE: 6
gagcagaagc tgatctctga ggaggatctg aagcttgaat atcaaggcca atcgtctgac 60

<210> SEQ ID NO 7
<211> LENGTH: 108
<212> TYPE: DNA
<213> ORGANISM: Artificial Sequence
<220> FEATURE:
<223> OTHER INFORMATION: Primer g3p-SecMstop

<400> SEQUENCE: 7
ctcgagttat tcattaggtg aggcgttgag ggccagcacg gatgccttgc gcctggctta 60
tccagacggg cgtgctgaat tttgcgccgg aaacgtcacc aatgaaac 108

<210> SEQ ID NO 8
<211> LENGTH: 48
<212> TYPE: DNA
<213> ORGANISM: Artificial Sequence
<220> FEATURE:
<223> OTHER INFORMATION: 5' primer

<400> SEQUENCE: 8
gaaattaata cgactcacta tagggagacc acaacggttt ccctctag 48

<210> SEQ ID NO 9
<211> LENGTH: 32
<212> TYPE: DNA
<213> ORGANISM: Artificial Sequence
<220> FEATURE:
<223> OTHER INFORMATION: Primer SecMstop

<400> SEQUENCE: 9
ggattagtta ttcattaggt gaggcgttga gg 32

<210> SEQ ID NO 10
<211> LENGTH: 22
<212> TYPE: DNA
<213> ORGANISM: Artificial Sequence
<220> FEATURE:
<223> OTHER INFORMATION: RT reverse primer Myc R

<400> SEQUENCE: 10
cagatcctcc tcagagatca gc 22

<210> SEQ ID NO 11
<211> LENGTH: 29
<212> TYPE: DNA
<213> ORGANISM: Artificial Sequence
<220> FEATURE:
<223> OTHER INFORMATION: Primer FLAG F

<400> SEQUENCE: 11
atggactata aagatgacga tgacaaagg 29

<210> SEQ ID NO 12
<211> LENGTH: 35
<212> TYPE: DNA
<213> ORGANISM: Artificial Sequence
<220> FEATURE:
<223> OTHER INFORMATION: Primer Eco1-(-M)-FLAG_F

<400> SEQUENCE: 12
ccgaattcga ctataaagat gacgatgaca aaggc 35

<210> SEQ ID NO 13
<211> LENGTH: 33
<212> TYPE: DNA
<213> ORGANISM: Artificial Sequence
<220> FEATURE:
<223> OTHER INFORMATION: Primer Myc-Hind3_R

<400> SEQUENCE: 13
aaaaaaaaaa gcttcagatc ctcctcagag atc 33

<210> SEQ ID NO 14
<211> LENGTH: 28
<212> TYPE: DNA
<213> ORGANISM: Artificial Sequence
<220> FEATURE:
<223> OTHER INFORMATION: Primer pET-MALseqF

<400> SEQUENCE: 14
ccagaaaggt gaaatcatgc cgaacatc 28

<210> SEQ ID NO 15
<211> LENGTH: 14
<212> TYPE: PRT
<213> ORGANISM: Artificial Sequence
<220> FEATURE:
<223> OTHER INFORMATION: H12SSI-Ctla4-3-02

<400> SEQUENCE: 15

Cys Met His Pro Phe Leu Leu Val Val Ser His His Phe Cys
1 5 10

<210> SEQ ID NO 16
<211> LENGTH: 14
<212> TYPE: PRT
<213> ORGANISM: Artificial Sequence
<220> FEATURE:
<223> OTHER INFORMATION: H12SSI-Ctla4-3-51

<400> SEQUENCE: 16

Cys Gly Leu Gly Gln Gly Tyr Trp Phe Lys Val Trp Phe Cys
1 5 10

<210> SEQ ID NO 17
<211> LENGTH: 14
<212> TYPE: PRT
<213> ORGANISM: Artificial Sequence
<220> FEATURE:
<223> OTHER INFORMATION: H12SSI-Ctla4-3-33

<400> SEQUENCE: 17

Cys Ala Lys Asn Phe Gly Tyr Trp Tyr His Gln Trp Phe Cys
1 5 10

<210> SEQ ID NO 18
<211> LENGTH: 14
<212> TYPE: PRT
<213> ORGANISM: Artificial Sequence
<220> FEATURE:
<223> OTHER INFORMATION: H12SSI-Ctla4-3-80

<400> SEQUENCE: 18

Cys Gly Ala Gly Lys Gly Phe Trp Phe Lys Val Trp Phe Cys
1 5 10

<210> SEQ ID NO 19
<211> LENGTH: 14
<212> TYPE: PRT
<213> ORGANISM: Artificial Sequence
<220> FEATURE:
<223> OTHER INFORMATION: H12SSI-Ctla4-2-23

<400> SEQUENCE: 19

Cys Gly Phe His Asp Gly Phe Trp Tyr Asn Val Trp Phe Cys
1 5 10

<210> SEQ ID NO 20
<211> LENGTH: 14
<212> TYPE: PRT
<213> ORGANISM: Artificial Sequence
<220> FEATURE:
<223> OTHER INFORMATION: H12SSI-Ctla4-3-90

<400> SEQUENCE: 20

Cys Gly Val Asn Leu Gly Phe Trp Phe Asn Val Trp Phe Cys
1 5 10

<210> SEQ ID NO 21
<211> LENGTH: 14
<212> TYPE: PRT
<213> ORGANISM: Artificial Sequence
<220> FEATURE:
<223> OTHER INFORMATION: H12SSI-Ctla4-3-38

<400> SEQUENCE: 21

Cys Ile Ile Gln Gly Gln Tyr Trp Trp Asn Ile Trp His Cys
1 5 10

<210> SEQ ID NO 22
<211> LENGTH: 16
<212> TYPE: PRT
<213> ORGANISM: Artificial Sequence
<220> FEATURE:
<223> OTHER INFORMATION: Clone #19

<400> SEQUENCE: 22

Cys Met His Pro Phe Leu Pro Ile Val Ser His His Phe Cys Glu Arg
1 5 10 15

<210> SEQ ID NO 23
<211> LENGTH: 15
<212> TYPE: PRT
<213> ORGANISM: Artificial Sequence
<220> FEATURE:
<223> OTHER INFORMATION: Original clone

<400> SEQUENCE: 23

Lys Cys Met His Pro Phe Leu Leu Val Val Ser His His Phe Cys
1 5 10 15

<210> SEQ ID NO 24
<211> LENGTH: 17
<212> TYPE: PRT
<213> ORGANISM: Artificial Sequence
<220> FEATURE:
<223> OTHER INFORMATION: Clone #19

<400> SEQUENCE: 24

Lys Cys Met His Pro Phe Leu Pro Ile Val Ser His His Phe Cys Glu
1 5 10 15

Arg

<210> SEQ ID NO 25
<211> LENGTH: 15
<212> TYPE: PRT
<213> ORGANISM: Artificial Sequence
<220> FEATURE:
<223> OTHER INFORMATION: Original clone

<400> SEQUENCE: 25

Gly Cys Met His Pro Phe Leu Leu Val Val Ser His His Phe Cys
1 5 10 15

<210> SEQ ID NO 26
<211> LENGTH: 17
<212> TYPE: PRT
<213> ORGANISM: Artificial Sequence
<220> FEATURE:
<223> OTHER INFORMATION: Clone #19

<400> SEQUENCE: 26

Gly Cys Met His Pro Phe Leu Pro Ile Val Ser His His Phe Cys Glu
1 5 10 15

Arg

<210> SEQ ID NO 27
<211> LENGTH: 16
<212> TYPE: PRT
<213> ORGANISM: Artificial Sequence
<220> FEATURE:
<223> OTHER INFORMATION: Clone #10

<400> SEQUENCE: 27

Cys Leu His Pro Phe Leu Pro Ile Val Ser His His Phe Cys Gly Arg
1 5 10 15

<210> SEQ ID NO 28
<211> LENGTH: 114
<212> TYPE: DNA
<213> ORGANISM: Artificial Sequence
<220> FEATURE:
<223> OTHER INFORMATION: Randomized oligo DNA
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (73)..(74)
<223> OTHER INFORMATION: n is a, c, g, or t
<220> FEATURE:
<221> NAME/KEY: misc_feature
<222> LOCATION: (76)..(77)
<223> OTHER INFORMATION: n is a, c, g, or t

<400> SEQUENCE: 28
gactataaag atgacgatga caaaggcggt tgcnnscatc cannsctgcc gatannstca 60
nnscatttct gtnnsnnsgg atccgagcag aagctgatct ctgaggagga tctg 114

<210> SEQ ID NO 29
<211> LENGTH: 18
<212> TYPE: PRT
<213> ORGANISM: Artificial Sequence
<220> FEATURE:
<223> OTHER INFORMATION: Original clone

<400> SEQUENCE: 29

Gly Gly Cys Met His Pro Phe Leu Leu Val Val Ser His His Phe Cys
1 5 10 15

Gly Gly

<210> SEQ ID NO 30
<211> LENGTH: 18
<212> TYPE: PRT
<213> ORGANISM: Artificial Sequence
<220> FEATURE:
<223> OTHER INFORMATION: C4-302mat-1-1-24

<400> SEQUENCE: 30

Gly Gly Cys Met His Pro Phe Leu Pro Val Val Ser His His Phe Cys
1 5 10 15

Gly Gly

<210> SEQ ID NO 31
<211> LENGTH: 18
<212> TYPE: PRT
<213> ORGANISM: Artificial Sequence
<220> FEATURE:
<223> OTHER INFORMATION: C4-302mat-2-100-18

<400> SEQUENCE: 31

Gly Gly Cys Met His Pro Phe Leu Pro Val Val Ser His His Phe Cys
1 5 10 15

Arg Gly

<210> SEQ ID NO 32
<211> LENGTH: 18
<212> TYPE: PRT
<213> ORGANISM: Artificial Sequence
<220> FEATURE:
<223> OTHER INFORMATION: C4-302mat-3-1-48

<400> SEQUENCE: 32

Gly Gly Cys Met His Pro Phe Leu Pro Val Val Ser His His Phe Cys
1 5 10 15

Gly Ala

<210> SEQ ID NO 33
<211> LENGTH: 18
<212> TYPE: PRT
<213> ORGANISM: Artificial Sequence
<220> FEATURE:
<223> OTHER INFORMATION: C4-302mat-3-100-37

<400> SEQUENCE: 33

Gly Gly Cys Met His Pro Phe Leu Pro Val Val Ser His His Phe Cys
1 5 10 15

Gly Arg

<210> SEQ ID NO 34
<211> LENGTH: 18
<212> TYPE: PRT

<213> ORGANISM: Artificial Sequence
<220> FEATURE:
<223> OTHER INFORMATION: C4-302mat-1-1-35

<400> SEQUENCE: 34

Gly Gly Cys Met His Pro Phe Leu Pro Val Ala Ser His His Phe Cys
1 5 10 15

Gly Gly

<210> SEQ ID NO 35
<211> LENGTH: 18
<212> TYPE: PRT
<213> ORGANISM: Artificial Sequence
<220> FEATURE:
<223> OTHER INFORMATION: C4-302mat-3-1-22

<400> SEQUENCE: 35

Gly Gly Cys Met His Pro Phe Leu Pro Val Ala Ser His His Phe Cys
1 5 10 15

Gly Arg

<210> SEQ ID NO 36
<211> LENGTH: 18
<212> TYPE: PRT
<213> ORGANISM: Artificial Sequence
<220> FEATURE:
<223> OTHER INFORMATION: C4-302mat-3-100-27

<400> SEQUENCE: 36

Gly Gly Cys Met His Pro Phe Leu Pro Val Ala Ser His His Phe Cys
1 5 10 15

Ala Gly

<210> SEQ ID NO 37
<211> LENGTH: 18
<212> TYPE: PRT
<213> ORGANISM: Artificial Sequence
<220> FEATURE:
<223> OTHER INFORMATION: GGCLHPFLPVVSHHFCGD

<400> SEQUENCE: 37

Gly Gly Cys Leu His Pro Phe Leu Pro Val Val Ser His His Phe Cys
1 5 10 15

Gly Asp

<210> SEQ ID NO 38
<211> LENGTH: 18
<212> TYPE: PRT
<213> ORGANISM: Artificial Sequence
<220> FEATURE:
<223> OTHER INFORMATION: C4-302mat-2-1-38

<400> SEQUENCE: 38

Gly Gly Cys Leu His Pro Phe Leu Pro Leu Val Ser His His Phe Cys
1 5 10 15

Gly Gly

<210> SEQ ID NO 39
<211> LENGTH: 18
<212> TYPE: PRT
<213> ORGANISM: Artificial Sequence
<220> FEATURE:
<223> OTHER INFORMATION: C4-302mat-3-100-44

<400> SEQUENCE: 39

Gly Gly Cys Leu His Pro Phe Leu Pro Ile Val Ser His His Phe Cys
1 5 10 15

Gly Arg

<210> SEQ ID NO 40
<211> LENGTH: 18
<212> TYPE: PRT
<213> ORGANISM: Artificial Sequence
<220> FEATURE:
<223> OTHER INFORMATION: C4-302mat-3-1-45

<400> SEQUENCE: 40

Gly Gly Cys Arg His Pro Phe Leu Pro Ile Val Ser Arg His Phe Cys
1 5 10 15

Arg Gly

<210> SEQ ID NO 41
<211> LENGTH: 18
<212> TYPE: PRT
<213> ORGANISM: Artificial Sequence
<220> FEATURE:
<223> OTHER INFORMATION: C4-302mat-3-100-20

<400> SEQUENCE: 41

Gly Gly Cys Val His Pro Phe Leu Pro Val Val Ser His His Phe Cys
1 5 10 15

Arg Gly

<210> SEQ ID NO 42
<211> LENGTH: 18
<212> TYPE: PRT
<213> ORGANISM: Artificial Sequence
<220> FEATURE:
<223> OTHER INFORMATION: C4-302mat-3-100-9

<400> SEQUENCE: 42

Gly Gly Cys Lys His Pro Phe Leu Pro Val Val Ser His His Phe Cys
1 5 10 15

Gly Gly

<210> SEQ ID NO 43
<211> LENGTH: 18
<212> TYPE: PRT
<213> ORGANISM: Artificial Sequence
<220> FEATURE:
<223> OTHER INFORMATION: C4-302mat-3-1-10

<400> SEQUENCE: 43

Gly Gly Cys Lys His Pro Tyr Leu Pro Val Ala Ser His His Phe Cys
1 5 10 15

Arg Gly

<210> SEQ ID NO 44
<211> LENGTH: 18
<212> TYPE: PRT
<213> ORGANISM: Artificial Sequence
<220> FEATURE:
<223> OTHER INFORMATION: C4-302mat-2-1-27

<400> SEQUENCE: 44

Gly Gly Cys Met His Pro Tyr Leu Pro Val Ile Ser His His Phe Cys
1 5 10 15

-continued

Gly Gly

<210> SEQ ID NO 45
<211> LENGTH: 18
<212> TYPE: PRT
<213> ORGANISM: Artificial Sequence
<220> FEATURE:
<223> OTHER INFORMATION: C4-302mat-3-100-12

<400> SEQUENCE: 45

Gly Gly Cys Met His Pro Tyr Leu Pro Val Ile Ser His His Phe Cys
1 5 10 15

Gly Arg

<210> SEQ ID NO 46
<211> LENGTH: 18
<212> TYPE: PRT
<213> ORGANISM: Artificial Sequence
<220> FEATURE:
<223> OTHER INFORMATION: C4-302mat-2-1-3

<400> SEQUENCE: 46

Gly Gly Cys Met His Pro Phe Leu Pro Val Thr Ser His His Phe Cys
1 5 10 15

Gly Gly

<210> SEQ ID NO 47
<211> LENGTH: 18
<212> TYPE: PRT
<213> ORGANISM: Artificial Sequence
<220> FEATURE:
<223> OTHER INFORMATION: C4-302mat-2-100-27

<400> SEQUENCE: 47

Gly Gly Cys Met His Pro Phe Leu Pro Ile Val Ser His His Phe Cys
1 5 10 15

Gly Ser

<210> SEQ ID NO 48
<211> LENGTH: 18
<212> TYPE: PRT
<213> ORGANISM: Artificial Sequence
<220> FEATURE:
<223> OTHER INFORMATION: C4-302mat-3-1-27

<400> SEQUENCE: 48

Gly Gly Cys Met His Pro Phe Leu Pro Ile Val Ser His His Phe Cys
1 5 10 15

Glu Arg

<210> SEQ ID NO 49
<211> LENGTH: 18
<212> TYPE: PRT
<213> ORGANISM: Artificial Sequence
<220> FEATURE:
<223> OTHER INFORMATION: C4-302mat-3-1-23

<400> SEQUENCE: 49

Gly Gly Cys Met His Pro Phe Leu Pro Ile Ala Ser Leu His Phe Cys
1 5 10 15

Gly Arg

<210> SEQ ID NO 50
<211> LENGTH: 18
<212> TYPE: PRT
<213> ORGANISM: Artificial Sequence
<220> FEATURE:
<223> OTHER INFORMATION: C4-302mat-3-1-32

<400> SEQUENCE: 50

Gly Gly Cys Met His Pro Phe Leu Pro Ile Leu Ser His His Phe Cys
1 5 10 15

Ala Gly

<210> SEQ ID NO 51
<211> LENGTH: 18
<212> TYPE: PRT
<213> ORGANISM: Artificial Sequence
<220> FEATURE:
<223> OTHER INFORMATION: C4-302mat-3-1-31

<400> SEQUENCE: 51

Gly Ser Cys Met His Pro Phe Leu Pro Val Ala Ser Arg His Phe Cys
1 5 10 15

Gly Arg

<210> SEQ ID NO 52
<211> LENGTH: 18
<212> TYPE: PRT
<213> ORGANISM: Artificial Sequence
<220> FEATURE:
<223> OTHER INFORMATION: C4-302mat-3-1-5

<400> SEQUENCE: 52

Gly Gly Cys Met His Pro Phe Leu Pro Val Val Ser Arg His Phe Cys
1 5 10 15

Gly Gly

<210> SEQ ID NO 53
<211> LENGTH: 18
<212> TYPE: PRT
<213> ORGANISM: Artificial Sequence
<220> FEATURE:
<223> OTHER INFORMATION: C4-302mat-3-1-12

<400> SEQUENCE: 53

Gly Gly Cys Met His Pro Phe Leu Pro Val Val Ser Arg His Phe Cys
1 5 10 15

Gly Arg

<210> SEQ ID NO 54
<211> LENGTH: 18
<212> TYPE: PRT
<213> ORGANISM: Artificial Sequence
<220> FEATURE:
<223> OTHER INFORMATION: C4-302mat-3-1-35

<400> SEQUENCE: 54

Gly Gly Cys Met His Pro Phe Leu Gln Thr Val Ser His His Phe Cys
1 5 10 15

Gly Gly

<210> SEQ ID NO 55
<211> LENGTH: 18
<212> TYPE: PRT
<213> ORGANISM: Artificial Sequence
<220> FEATURE:
<223> OTHER INFORMATION: C4-302mat-2-1-35

<400> SEQUENCE: 55

Gly Gly Cys Met His Pro Phe Leu Gln Val Val Ser His His Phe Cys
1 5 10 15

Gly Ser

<210> SEQ ID NO 56
<211> LENGTH: 18
<212> TYPE: PRT
<213> ORGANISM: Artificial Sequence
<220> FEATURE:
<223> OTHER INFORMATION: C4-302mat-2-100-4

<400> SEQUENCE: 56

Gly Gly Cys Met His Pro Phe Leu Gln Val Val Ser His His Phe Cys
1 5 10 15

Gly Gly

<210> SEQ ID NO 57
<211> LENGTH: 18
<212> TYPE: PRT
<213> ORGANISM: Artificial Sequence
<220> FEATURE:
<223> OTHER INFORMATION: C4-302mat-1-1-21

<400> SEQUENCE: 57

Gly Gly Cys Ile His Pro Phe Leu Gln Val Val Ser His His Phe Cys
1 5 10 15

Gly Gly

<210> SEQ ID NO 58
<211> LENGTH: 18
<212> TYPE: PRT
<213> ORGANISM: Artificial Sequence
<220> FEATURE:
<223> OTHER INFORMATION: C4-302mat-1-100-23

<400> SEQUENCE: 58

Gly Gly Cys Val His Pro Phe Leu Gln Val Val Ser His His Phe Cys
1 5 10 15

Gly Gly

<210> SEQ ID NO 59
<211> LENGTH: 18
<212> TYPE: PRT
<213> ORGANISM: Artificial Sequence
<220> FEATURE:
<223> OTHER INFORMATION: C4-302mat-2-1-40

<400> SEQUENCE: 59

Gly Gly Cys Met His Pro Phe Leu Gln Val Ala Ser His His Phe Cys
1 5 10 15

Gly Gly

<210> SEQ ID NO 60
<211> LENGTH: 18
<212> TYPE: PRT
<213> ORGANISM: Artificial Sequence
<220> FEATURE:
<223> OTHER INFORMATION: C4-302mat-3-1-2

<400> SEQUENCE: 60

```
Gly Gly Cys Met His Pro Tyr Leu Gln Val Val Ser His His Phe Cys
1               5                   10                  15

Gly Arg


<210> SEQ ID NO 61
<211> LENGTH: 18
<212> TYPE: PRT
<213> ORGANISM: Artificial Sequence
<220> FEATURE:
<223> OTHER INFORMATION: C4-302mat-1-1-37

<400> SEQUENCE: 61

Gly Gly Cys Met His Pro Phe Leu Arg Val Val Ser His His Phe Cys
1               5                   10                  15

Gly Gly


<210> SEQ ID NO 62
<211> LENGTH: 18
<212> TYPE: PRT
<213> ORGANISM: Artificial Sequence
<220> FEATURE:
<223> OTHER INFORMATION: C4-302mat-3-1-14

<400> SEQUENCE: 62

Gly Gly Cys Met His Pro Phe Leu Arg Val Val Ser His His Phe Cys
1               5                   10                  15

Gly Arg


<210> SEQ ID NO 63
<211> LENGTH: 18
<212> TYPE: PRT
<213> ORGANISM: Artificial Sequence
<220> FEATURE:
<223> OTHER INFORMATION: C4-302mat-2-1-12

<400> SEQUENCE: 63

Gly Gly Cys Lys His Pro Phe Leu Arg Val Val Ser His His Phe Cys
1               5                   10                  15

Arg Arg


<210> SEQ ID NO 64
<211> LENGTH: 18
<212> TYPE: PRT
<213> ORGANISM: Artificial Sequence
<220> FEATURE:
<223> OTHER INFORMATION: C4-302mat-2-1-24

<400> SEQUENCE: 64

Gly Gly Cys Met His Pro Phe Leu Arg Ile Val Ser Gln His Phe Cys
1               5                   10                  15

Arg Arg


<210> SEQ ID NO 65
<211> LENGTH: 18
<212> TYPE: PRT
<213> ORGANISM: Artificial Sequence
<220> FEATURE:
<223> OTHER INFORMATION: C4-302mat-3-1-8

<400> SEQUENCE: 65

Gly Gly Cys Met His Pro Phe Leu Lys Ile Ala Ser His His Phe Cys
1               5                   10                  15
```

Gly Gly

<210> SEQ ID NO 66
<211> LENGTH: 18
<212> TYPE: PRT
<213> ORGANISM: Artificial Sequence
<220> FEATURE:
<223> OTHER INFORMATION: C4-302mat-2-1-37

<400> SEQUENCE: 66

```
Gly Gly Cys Met His Pro Phe Leu Leu Val Ala Ser His His Phe Cys
1               5                   10                  15

Gly Val
```

<210> SEQ ID NO 67
<211> LENGTH: 18
<212> TYPE: PRT
<213> ORGANISM: Artificial Sequence
<220> FEATURE:
<223> OTHER INFORMATION: C4-302mat-2-100-33

<400> SEQUENCE: 67

```
Gly Ser Cys Met His Pro Phe Leu Leu Val Ala Ser His His Phe Cys
1               5                   10                  15

Arg Gly
```

<210> SEQ ID NO 68
<211> LENGTH: 18
<212> TYPE: PRT
<213> ORGANISM: Artificial Sequence
<220> FEATURE:
<223> OTHER INFORMATION: C4-302mat-3-1-9

<400> SEQUENCE: 68

```
Gly Gly Cys Met His Pro Tyr Leu Leu Val Ala Ser His His Phe Cys
1               5                   10                  15

Glu Arg
```

<210> SEQ ID NO 69
<211> LENGTH: 18
<212> TYPE: PRT
<213> ORGANISM: Artificial Sequence
<220> FEATURE:
<223> OTHER INFORMATION: C4-302mat-2-100-24

<400> SEQUENCE: 69

```
Gly Gly Cys Met His Pro Tyr Leu Leu Val Val Ser His His Phe Cys
1               5                   10                  15

Gly Arg
```

<210> SEQ ID NO 70
<211> LENGTH: 18
<212> TYPE: PRT
<213> ORGANISM: Artificial Sequence
<220> FEATURE:
<223> OTHER INFORMATION: C4-302mat-3-1-15

<400> SEQUENCE: 70

```
Gly Gly Cys Met His Pro Tyr Leu Leu Val Val Ser Arg His Phe Cys
1               5                   10                  15

Gly Arg
```

<210> SEQ ID NO 71

<211> LENGTH: 18
<212> TYPE: PRT
<213> ORGANISM: Artificial Sequence
<220> FEATURE:
<223> OTHER INFORMATION: C4-302mat-3-1-25

<400> SEQUENCE: 71

Gly Asp Cys Lys His Pro Tyr Leu Leu Thr Val Ser His His Phe Cys
1 5 10 15

Gly Arg

<210> SEQ ID NO 72
<211> LENGTH: 18
<212> TYPE: PRT
<213> ORGANISM: Artificial Sequence
<220> FEATURE:
<223> OTHER INFORMATION: C4-302mat-2-100-40

<400> SEQUENCE: 72

Gly Gly Cys Met His Pro Phe Leu Leu Val Val Ser Arg His Phe Cys
1 5 10 15

Gly Arg

<210> SEQ ID NO 73
<211> LENGTH: 18
<212> TYPE: PRT
<213> ORGANISM: Artificial Sequence
<220> FEATURE:
<223> OTHER INFORMATION: C4-302mat-3-1-11

<400> SEQUENCE: 73

Gly Gly Cys Met His Pro Phe Leu Leu Thr Val Ser Arg His Phe Cys
1 5 10 15

Gly Gly

<210> SEQ ID NO 74
<211> LENGTH: 18
<212> TYPE: PRT
<213> ORGANISM: Artificial Sequence
<220> FEATURE:
<223> OTHER INFORMATION: C4-302mat-3-100-39

<400> SEQUENCE: 74

Gly Gly Cys Lys His Pro Phe Leu Leu Ile Val Ser His His Phe Cys
1 5 10 15

Gly Arg

<210> SEQ ID NO 75
<211> LENGTH: 18
<212> TYPE: PRT
<213> ORGANISM: Artificial Sequence
<220> FEATURE:
<223> OTHER INFORMATION: C4m#19-5th4w-NN6-67

<400> SEQUENCE: 75

Gly Gly Cys Leu His Pro Phe Leu Pro Ile Arg Ser Val His Phe Cys
1 5 10 15

Pro Arg

<210> SEQ ID NO 76
<211> LENGTH: 18
<212> TYPE: PRT
<213> ORGANISM: Artificial Sequence
<220> FEATURE:

<223> OTHER INFORMATION: GGCLHPFLPIRSVHFCPF

<400> SEQUENCE: 76

Gly Gly Cys Leu His Pro Phe Leu Pro Ile Arg Ser Val His Phe Cys
1 5 10 15

Pro Phe

<210> SEQ ID NO 77
<211> LENGTH: 18
<212> TYPE: PRT
<213> ORGANISM: Artificial Sequence
<220> FEATURE:
<223> OTHER INFORMATION: C4m#19-5th4w-NN6-25

<400> SEQUENCE: 77

Gly Gly Cys Leu His Pro Val Leu Pro Ile Arg Ser Arg His Phe Cys
1 5 10 15

Pro Val

<210> SEQ ID NO 78
<211> LENGTH: 18
<212> TYPE: PRT
<213> ORGANISM: Artificial Sequence
<220> FEATURE:
<223> OTHER INFORMATION: C4m#19-5th4w-NN6-21

<400> SEQUENCE: 78

Gly Gly Cys Trp His Pro Trp Leu Pro Ile Leu Ser Pro His Phe Cys
1 5 10 15

Pro Arg

<210> SEQ ID NO 79
<211> LENGTH: 18
<212> TYPE: PRT
<213> ORGANISM: Artificial Sequence
<220> FEATURE:
<223> OTHER INFORMATION: C4m#19-5th4w-NN6-39

<400> SEQUENCE: 79

Gly Gly Cys Trp His Pro Phe Leu Pro Ile Arg Ser Leu His Phe Cys
1 5 10 15

Pro Arg

<210> SEQ ID NO 80
<211> LENGTH: 18
<212> TYPE: PRT
<213> ORGANISM: Artificial Sequence
<220> FEATURE:
<223> OTHER INFORMATION: C4m#19-5th4w-NN6-70

<400> SEQUENCE: 80

Gly Gly Cys Met His Pro Phe Leu Pro Ile Arg Ser Met His Phe Cys
1 5 10 15

Pro Leu

<210> SEQ ID NO 81
<211> LENGTH: 18
<212> TYPE: PRT
<213> ORGANISM: Artificial Sequence
<220> FEATURE:
<223> OTHER INFORMATION: C4m#19-5th2w-NNS6-14

<400> SEQUENCE: 81

Gly Gly Cys Trp His Pro Phe Leu Pro Ile Arg Ser Tyr His Phe Cys
1 5 10 15

Pro Trp

<210> SEQ ID NO 82
<211> LENGTH: 18
<212> TYPE: PRT
<213> ORGANISM: Artificial Sequence
<220> FEATURE:
<223> OTHER INFORMATION: C4m#19-5th4w-NN6-47

<400> SEQUENCE: 82

Gly Gly Cys Pro His Pro Trp Leu Pro Ile Phe Ser Arg His Phe Cys
1 5 10 15

Pro Val

<210> SEQ ID NO 83
<211> LENGTH: 18
<212> TYPE: PRT
<213> ORGANISM: Artificial Sequence
<220> FEATURE:
<223> OTHER INFORMATION: C4m#19-5th4w-NN6-54

<400> SEQUENCE: 83

Gly Gly Cys Leu His Pro Gly Leu Pro Ile Arg Ser Leu His Phe Cys
1 5 10 15

Pro Arg

<210> SEQ ID NO 84
<211> LENGTH: 18
<212> TYPE: PRT
<213> ORGANISM: Artificial Sequence
<220> FEATURE:
<223> OTHER INFORMATION: C4m#19-5th4w-NN6-81

<400> SEQUENCE: 84

Gly Gly Cys Phe His Pro Tyr Leu Pro Ile Arg Ser Trp His Phe Cys
1 5 10 15

Ser Arg

<210> SEQ ID NO 85
<211> LENGTH: 18
<212> TYPE: PRT
<213> ORGANISM: Artificial Sequence
<220> FEATURE:
<223> OTHER INFORMATION: C4m#19-5th4w-NN6-53

<400> SEQUENCE: 85

Gly Gly Cys Arg His Pro Phe Leu Pro Ile Tyr Ser Val His Phe Cys
1 5 10 15

Ala Cys

<210> SEQ ID NO 86
<211> LENGTH: 18
<212> TYPE: PRT
<213> ORGANISM: Artificial Sequence
<220> FEATURE:
<223> OTHER INFORMATION: C4m#19-5th4w-NN6-34

<400> SEQUENCE: 86

Gly Gly Cys Phe His Pro Phe Leu Pro Ile Arg Ser Asp His Phe Cys
1 5 10 15

Ser Arg

```
<210> SEQ ID NO 87
<211> LENGTH: 18
<212> TYPE: PRT
<213> ORGANISM: Artificial Sequence
<220> FEATURE:
<223> OTHER INFORMATION: C4m#19-5th4w-NN6-4

<400> SEQUENCE: 87

Gly Gly Cys Arg His Pro Tyr Leu Pro Ile Val Ser Arg His Phe Cys
1               5                   10                  15

Pro Phe


<210> SEQ ID NO 88
<211> LENGTH: 18
<212> TYPE: PRT
<213> ORGANISM: Artificial Sequence
<220> FEATURE:
<223> OTHER INFORMATION: C4m#19-5th2w-NNS6-21

<400> SEQUENCE: 88

Gly Gly Cys Trp His Pro Phe Leu Pro Ile Arg Ser Ser His Phe Cys
1               5                   10                  15

Pro Ser


<210> SEQ ID NO 89
<211> LENGTH: 18
<212> TYPE: PRT
<213> ORGANISM: Artificial Sequence
<220> FEATURE:
<223> OTHER INFORMATION: C4m#19-5th4w-NN6-20

<400> SEQUENCE: 89

Gly Gly Cys Ser His Pro Gln Leu Pro Ile Leu Ser Asp His Phe Cys
1               5                   10                  15

Ser Ala


<210> SEQ ID NO 90
<211> LENGTH: 18
<212> TYPE: PRT
<213> ORGANISM: Artificial Sequence
<220> FEATURE:
<223> OTHER INFORMATION: C4m#19-5th4w-NN6-77

<400> SEQUENCE: 90

Gly Gly Cys Arg His Pro Phe Leu Pro Ile Val Ser Thr His Phe Cys
1               5                   10                  15

Ser Arg


<210> SEQ ID NO 91
<211> LENGTH: 18
<212> TYPE: PRT
<213> ORGANISM: Artificial Sequence
<220> FEATURE:
<223> OTHER INFORMATION: C4m#19-5th4w-NN6-23

<400> SEQUENCE: 91

Gly Gly Cys Arg His Pro His Leu Pro Ile Trp Ser Trp His Phe Cys
1               5                   10                  15

Gly Arg


<210> SEQ ID NO 92
<211> LENGTH: 18
```

<212> TYPE: PRT
<213> ORGANISM: Artificial Sequence
<220> FEATURE:
<223> OTHER INFORMATION: C4m#19-5th4w-NN6-44

<400> SEQUENCE: 92

Gly Gly Cys Arg His Pro Phe Leu Pro Ile Val Ser Trp His Phe Cys
1 5 10 15

Gly Arg

<210> SEQ ID NO 93
<211> LENGTH: 18
<212> TYPE: PRT
<213> ORGANISM: Artificial Sequence
<220> FEATURE:
<223> OTHER INFORMATION: C4m#19-5th4w-NN6-92-1

<400> SEQUENCE: 93

Gly Gly Cys Val His Pro Phe Leu Pro Ile Arg Ser Val His Phe Cys
1 5 10 15

Ala Leu

<210> SEQ ID NO 94
<211> LENGTH: 18
<212> TYPE: PRT
<213> ORGANISM: Artificial Sequence
<220> FEATURE:
<223> OTHER INFORMATION: C4m#19-5th4w-NN6-91

<400> SEQUENCE: 94

Gly Gly Cys Met His Pro Tyr Leu Arg Ile Ile Ser Pro His Phe Cys
1 5 10 15

Arg Gly

<210> SEQ ID NO 95
<211> LENGTH: 18
<212> TYPE: PRT
<213> ORGANISM: Artificial Sequence
<220> FEATURE:
<223> OTHER INFORMATION: C4m#19-5th4w-NN6-19

<400> SEQUENCE: 95

Gly Gly Cys Arg His Pro Tyr Leu Pro Ile Trp Ser Ile His Phe Cys
1 5 10 15

Gln Lys

<210> SEQ ID NO 96
<211> LENGTH: 18
<212> TYPE: PRT
<213> ORGANISM: Artificial Sequence
<220> FEATURE:
<223> OTHER INFORMATION: C4m#19-5th4w-NN6-55-1

<400> SEQUENCE: 96

Gly Gly Cys Trp His Pro Phe Leu Pro Ile Ser Ser Pro His Phe Cys
1 5 10 15

Gly Arg

<210> SEQ ID NO 97
<211> LENGTH: 18
<212> TYPE: PRT
<213> ORGANISM: Artificial Sequence
<220> FEATURE:
<223> OTHER INFORMATION: C4m#19-5th4w-NN6-55-4

<400> SEQUENCE: 97

Gly Gly Cys Val His Pro Ser Leu Pro Ile Leu Ser Val His Phe Cys
1 5 10 15

Pro Arg

<210> SEQ ID NO 98
<211> LENGTH: 18
<212> TYPE: PRT
<213> ORGANISM: Artificial Sequence
<220> FEATURE:
<223> OTHER INFORMATION: C4m#19-5th2w-NNS6-22

<400> SEQUENCE: 98

Gly Gly Cys Met His Pro Phe Leu Pro Ile Gln Ser Val His Phe Cys
1 5 10 15

Ser Arg

<210> SEQ ID NO 99
<211> LENGTH: 18
<212> TYPE: PRT
<213> ORGANISM: Artificial Sequence
<220> FEATURE:
<223> OTHER INFORMATION: C4m#19-5th4w-NN6-93

<400> SEQUENCE: 99

Gly Gly Cys Cys His Pro Trp Leu Pro Ile Val Ser Thr His Phe Cys
1 5 10 15

Gly Leu

<210> SEQ ID NO 100
<211> LENGTH: 18
<212> TYPE: PRT
<213> ORGANISM: Artificial Sequence
<220> FEATURE:
<223> OTHER INFORMATION: C4m#19-5th4w-NN6-9

<400> SEQUENCE: 100

Gly Gly Cys Phe His Pro Tyr Leu Pro Ile Arg Ser Trp His Phe Cys
1 5 10 15

Gly Arg

<210> SEQ ID NO 101
<211> LENGTH: 18
<212> TYPE: PRT
<213> ORGANISM: Artificial Sequence
<220> FEATURE:
<223> OTHER INFORMATION: C4m#19-5th4w-NN6-52

<400> SEQUENCE: 101

Gly Gly Cys Leu His Pro Phe Leu Pro Ile Arg Ser Val His Phe Cys
1 5 10 15

Gly Cys

<210> SEQ ID NO 102
<211> LENGTH: 18
<212> TYPE: PRT
<213> ORGANISM: Artificial Sequence
<220> FEATURE:
<223> OTHER INFORMATION: C4m#19-5th2w-NNS6-55

<400> SEQUENCE: 102

Gly Gly Cys Met His Pro Tyr Leu Pro Ile Lys Ser Val His Phe Cys 1 5 10 15

Pro Leu

<210> SEQ ID NO 103
<211> LENGTH: 18
<212> TYPE: PRT
<213> ORGANISM: Artificial Sequence
<220> FEATURE:
<223> OTHER INFORMATION: C4m#19-5th4w-NN6-82

<400> SEQUENCE: 103

Gly Gly Cys Phe His Pro Phe Leu Pro Ile Arg Ser Leu His Phe Cys
1 5 10 15

Cys Arg

<210> SEQ ID NO 104
<211> LENGTH: 18
<212> TYPE: PRT
<213> ORGANISM: Artificial Sequence
<220> FEATURE:
<223> OTHER INFORMATION: C4m#19-5th4w-NN6-50

<400> SEQUENCE: 104

Gly Gly Cys Lys His Pro Val Leu Pro Ile Trp Ser Trp His Phe Cys
1 5 10 15

Arg Ile

<210> SEQ ID NO 105
<211> LENGTH: 18
<212> TYPE: PRT
<213> ORGANISM: Artificial Sequence
<220> FEATURE:
<223> OTHER INFORMATION: C4m#19-5th4w-NN6-78

<400> SEQUENCE: 105

Gly Gly Cys Trp His Pro Ala Leu Pro Ile Arg Ser Trp His Phe Cys
1 5 10 15

Pro Arg

<210> SEQ ID NO 106
<211> LENGTH: 18
<212> TYPE: PRT
<213> ORGANISM: Artificial Sequence
<220> FEATURE:
<223> OTHER INFORMATION: C4m#19-5th4w-NN6-57

<400> SEQUENCE: 106

Gly Gly Cys Met His Pro Tyr Leu Pro Ile Val Ser Val His Phe Cys
1 5 10 15

Pro Cys

<210> SEQ ID NO 107
<211> LENGTH: 18
<212> TYPE: PRT
<213> ORGANISM: Artificial Sequence
<220> FEATURE:
<223> OTHER INFORMATION: C4m#19-5th4w-NN6-59

<400> SEQUENCE: 107

Gly Gly Cys Leu His Pro His Leu Pro Ile Trp Ser Leu His Phe Cys
1 5 10 15

Pro Leu

<210> SEQ ID NO 108
<211> LENGTH: 18
<212> TYPE: PRT
<213> ORGANISM: Artificial Sequence
<220> FEATURE:
<223> OTHER INFORMATION: C4m#19-5th4w-NN6-24

<400> SEQUENCE: 108

Gly Gly Cys Trp His Pro Trp Leu Pro Ile Tyr Ser His His Phe Cys
1 5 10 15

Pro Ile

<210> SEQ ID NO 109
<211> LENGTH: 18
<212> TYPE: PRT
<213> ORGANISM: Artificial Sequence
<220> FEATURE:
<223> OTHER INFORMATION: C4m#19-5th4w-NN6-32

<400> SEQUENCE: 109

Gly Gly Cys Pro His Pro Phe Leu Pro Ile Trp Ser Val His Phe Cys
1 5 10 15

Pro Phe

<210> SEQ ID NO 110
<211> LENGTH: 18
<212> TYPE: PRT
<213> ORGANISM: Artificial Sequence
<220> FEATURE:
<223> OTHER INFORMATION: C4m#19-5th4w-NN6-56

<400> SEQUENCE: 110

Gly Gly Cys Trp His Pro Phe Leu Pro Ile Gln Ser Leu His Phe Cys
1 5 10 15

Gly Val

<210> SEQ ID NO 111
<211> LENGTH: 18
<212> TYPE: PRT
<213> ORGANISM: Artificial Sequence
<220> FEATURE:
<223> OTHER INFORMATION: C4m#19-5th2w-NNS6-67

<400> SEQUENCE: 111

Gly Gly Cys Gln His Pro Trp Leu Pro Ile Ser Ser Trp His Phe Cys
1 5 10 15

Pro Arg

<210> SEQ ID NO 112
<211> LENGTH: 18
<212> TYPE: PRT
<213> ORGANISM: Artificial Sequence
<220> FEATURE:
<223> OTHER INFORMATION: C4m#19-5th4w-NN6-69-1

<400> SEQUENCE: 112

Gly Gly Cys Ser His Pro Phe Leu Pro Ile Leu Ser Val His Phe Cys
1 5 10 15

Pro Phe

<210> SEQ ID NO 113
<211> LENGTH: 18
<212> TYPE: PRT

<213> ORGANISM: Artificial Sequence
<220> FEATURE:
<223> OTHER INFORMATION: C4m#19-5th4w-NN6-69-3

<400> SEQUENCE: 113

Gly Gly Cys Leu His Pro Trp Leu Pro Ile Val Ser Val His Phe Cys
1 5 10 15

Ala Arg

<210> SEQ ID NO 114
<211> LENGTH: 18
<212> TYPE: PRT
<213> ORGANISM: Artificial Sequence
<220> FEATURE:
<223> OTHER INFORMATION: C4m#19-5th4w-NN6-79

<400> SEQUENCE: 114

Gly Gly Cys Trp His Pro Val Leu Pro Ile Arg Ser Cys His Phe Cys
1 5 10 15

Ala Val

<210> SEQ ID NO 115
<211> LENGTH: 18
<212> TYPE: PRT
<213> ORGANISM: Artificial Sequence
<220> FEATURE:
<223> OTHER INFORMATION: C4m#19-5th4w-NN6-68

<400> SEQUENCE: 115

Gly Gly Cys Leu His Pro Trp Leu Pro Ile Arg Ser Arg His Phe Cys
1 5 10 15

Ser Arg

<210> SEQ ID NO 116
<211> LENGTH: 18
<212> TYPE: PRT
<213> ORGANISM: Artificial Sequence
<220> FEATURE:
<223> OTHER INFORMATION: C4m3127-4th-NNS6-28

<400> SEQUENCE: 116

Gly Gly Cys Leu His Pro Phe Leu Pro Ile Phe Ser Ser His Phe Cys
1 5 10 15

Ala Leu

<210> SEQ ID NO 117
<211> LENGTH: 18
<212> TYPE: PRT
<213> ORGANISM: Artificial Sequence
<220> FEATURE:
<223> OTHER INFORMATION: C4m#19-5th4w-NN6-7

<400> SEQUENCE: 117

Gly Gly Cys Arg His Pro Phe Leu Pro Ile Trp Ser Trp His Phe Cys
1 5 10 15

Pro Phe

<210> SEQ ID NO 118
<211> LENGTH: 18
<212> TYPE: PRT
<213> ORGANISM: Artificial Sequence
<220> FEATURE:
<223> OTHER INFORMATION: C4m#19-5th4w-NN6-85

<400> SEQUENCE: 118

Gly Gly Cys Trp His Pro Phe Leu Pro Ile Phe Ser Val His Phe Cys
1 5 10 15

Gly Cys

<210> SEQ ID NO 119
<211> LENGTH: 18
<212> TYPE: PRT
<213> ORGANISM: Artificial Sequence
<220> FEATURE:
<223> OTHER INFORMATION: C4m#19-5th2w-NNS6-71

<400> SEQUENCE: 119

Gly Gly Cys Arg His Pro Tyr Leu Pro Ile Ala Ser Pro His Phe Cys
1 5 10 15

Pro Gly

<210> SEQ ID NO 120
<211> LENGTH: 18
<212> TYPE: PRT
<213> ORGANISM: Artificial Sequence
<220> FEATURE:
<223> OTHER INFORMATION: C4m3127-4th-NNS6-90

<400> SEQUENCE: 120

Gly Gly Cys Lys His Pro Val Leu Pro Ile Val Ser Leu His Phe Cys
1 5 10 15

Pro Trp

<210> SEQ ID NO 121
<211> LENGTH: 18
<212> TYPE: PRT
<213> ORGANISM: Artificial Sequence
<220> FEATURE:
<223> OTHER INFORMATION: C4m#19-5th4w-NN6-37

<400> SEQUENCE: 121

Gly Gly Cys Leu His Pro Phe Leu Pro Ile Ser Ser Trp His Phe Cys
1 5 10 15

Gly Arg

<210> SEQ ID NO 122
<211> LENGTH: 18
<212> TYPE: PRT
<213> ORGANISM: Artificial Sequence
<220> FEATURE:
<223> OTHER INFORMATION: C4m#19-5th2w-NNS6-94

<400> SEQUENCE: 122

Gly Gly Cys Phe His Pro Tyr Leu Pro Ile Ser Ser Val His Phe Cys
1 5 10 15

Gly Arg

<210> SEQ ID NO 123
<211> LENGTH: 18
<212> TYPE: PRT
<213> ORGANISM: Artificial Sequence
<220> FEATURE:
<223> OTHER INFORMATION: C4m#19-5th4w-NN6-51

<400> SEQUENCE: 123

Gly Gly Cys Trp His Pro Tyr Leu Pro Ile Val Ser Trp His Phe Cys
1 5 10 15

Ser Arg

<210> SEQ ID NO 124
<211> LENGTH: 18
<212> TYPE: PRT
<213> ORGANISM: Artificial Sequence
<220> FEATURE:
<223> OTHER INFORMATION: C4m#19-5th4w-NN6-11

<400> SEQUENCE: 124

Gly Gly Cys Arg His Pro Phe Leu Pro Ile Trp Ser His His Phe Cys
1 5 10 15

Val Cys

<210> SEQ ID NO 125
<211> LENGTH: 18
<212> TYPE: PRT
<213> ORGANISM: Artificial Sequence
<220> FEATURE:
<223> OTHER INFORMATION: C4m#19-5th4w-NN6-87

<400> SEQUENCE: 125

Gly Gly Cys Leu His Pro Val Leu Pro Ile Arg Ser Phe His Phe Cys
1 5 10 15

Trp Arg

<210> SEQ ID NO 126
<211> LENGTH: 18
<212> TYPE: PRT
<213> ORGANISM: Artificial Sequence
<220> FEATURE:
<223> OTHER INFORMATION: C4m3127-4th-NNS6-87

<400> SEQUENCE: 126

Gly Gly Cys Arg His Pro Trp Leu Pro Ile Val Ser Trp His Phe Cys
1 5 10 15

Ser Arg

<210> SEQ ID NO 127
<211> LENGTH: 18
<212> TYPE: PRT
<213> ORGANISM: Artificial Sequence
<220> FEATURE:
<223> OTHER INFORMATION: C4m#19-5th4w-NN6-90

<400> SEQUENCE: 127

Gly Gly Cys Arg His Pro Trp Leu Pro Ile Val Ser Tyr His Phe Cys
1 5 10 15

Ser Ser

<210> SEQ ID NO 128
<211> LENGTH: 18
<212> TYPE: PRT
<213> ORGANISM: Artificial Sequence
<220> FEATURE:
<223> OTHER INFORMATION: C4m#19-5th2w-NNS6-25

<400> SEQUENCE: 128

Gly Gly Cys Lys His Pro Phe Leu Pro Ile Ser Ser His His Phe Cys
1 5 10 15

Pro Tyr

<210> SEQ ID NO 129
<211> LENGTH: 18
<212> TYPE: PRT
<213> ORGANISM: Artificial Sequence
<220> FEATURE:
<223> OTHER INFORMATION: C4m3127-4th-NNS6-83

<400> SEQUENCE: 129

Gly Gly Cys Arg His Pro Phe Leu Pro Ile Phe Ser Lys His Phe Cys
1 5 10 15

Glu Leu

<210> SEQ ID NO 130
<211> LENGTH: 18
<212> TYPE: PRT
<213> ORGANISM: Artificial Sequence
<220> FEATURE:
<223> OTHER INFORMATION: C4m3127-4th-NNS6-17

<400> SEQUENCE: 130

Gly Gly Cys Arg His Pro Val Leu Pro Ile Val Ser Leu His Phe Cys
1 5 10 15

Pro Gly

<210> SEQ ID NO 131
<211> LENGTH: 18
<212> TYPE: PRT
<213> ORGANISM: Artificial Sequence
<220> FEATURE:
<223> OTHER INFORMATION: C4m#19-5th2w-NNS6-12

<400> SEQUENCE: 131

Gly Gly Cys Trp His Pro Tyr Leu Pro Ile Arg Ser Val His Phe Cys
1 5 10 15

Gly Arg

<210> SEQ ID NO 132
<211> LENGTH: 18
<212> TYPE: PRT
<213> ORGANISM: Artificial Sequence
<220> FEATURE:
<223> OTHER INFORMATION: C4m3127-4th-NNS6-72

<400> SEQUENCE: 132

Gly Gly Cys Val His Pro Tyr Leu Pro Ile Ser Ser Ile His Phe Cys
1 5 10 15

Ser Met

<210> SEQ ID NO 133
<211> LENGTH: 18
<212> TYPE: PRT
<213> ORGANISM: Artificial Sequence
<220> FEATURE:
<223> OTHER INFORMATION: C4m#19-5th2w-NNS6-90

<400> SEQUENCE: 133

Gly Gly Cys Arg His Pro Phe Leu Pro Ile Val Ser Phe His Phe Cys
1 5 10 15

Pro Phe

<210> SEQ ID NO 134
<211> LENGTH: 18
<212> TYPE: PRT
<213> ORGANISM: Artificial Sequence
<220> FEATURE:
<223> OTHER INFORMATION: C4m#19-5th4w-NN6-86

<400> SEQUENCE: 134

Gly Gly Cys Ala His Pro Val Leu Pro Ile Arg Ser Leu His Phe Cys
1 5 10 15

Pro His

<210> SEQ ID NO 135
<211> LENGTH: 18
<212> TYPE: PRT
<213> ORGANISM: Artificial Sequence
<220> FEATURE:
<223> OTHER INFORMATION: C4m#19-5th4w-NN6-58

<400> SEQUENCE: 135

Gly Gly Cys Arg His Pro Phe Leu Pro Ile Ser Ser Ile His Phe Cys
1 5 10 15

Cys Ile

<210> SEQ ID NO 136
<211> LENGTH: 18
<212> TYPE: PRT
<213> ORGANISM: Artificial Sequence
<220> FEATURE:
<223> OTHER INFORMATION: C4m#19-5th2w-NNS6-3

<400> SEQUENCE: 136

Gly Gly Cys Ala His Pro Phe Leu Pro Ile Phe Ser Pro His Phe Cys
1 5 10 15

Pro Phe

<210> SEQ ID NO 137
<211> LENGTH: 18
<212> TYPE: PRT
<213> ORGANISM: Artificial Sequence
<220> FEATURE:
<223> OTHER INFORMATION: C4m#19-5th4w-NN6-2

<400> SEQUENCE: 137

Gly Gly Cys Trp His Pro His Leu Pro Ile Val Ser Ser His Phe Cys
1 5 10 15

Leu Phe

<210> SEQ ID NO 138
<211> LENGTH: 18
<212> TYPE: PRT
<213> ORGANISM: Artificial Sequence
<220> FEATURE:
<223> OTHER INFORMATION: C4m#19-5th4w-NN6-71

<400> SEQUENCE: 138

Gly Gly Cys Pro His Pro Trp Leu Pro Ile Ala Ser Val His Phe Cys
1 5 10 15

Pro Phe

<210> SEQ ID NO 139
<211> LENGTH: 18
<212> TYPE: PRT
<213> ORGANISM: Artificial Sequence
<220> FEATURE:
<223> OTHER INFORMATION: C4m#19-5th4w-NN6-62

<400> SEQUENCE: 139

Gly Gly Cys Gln His Pro Tyr Leu Pro Ile Trp Ser Phe His Phe Cys
1 5 10 15

Pro Phe

<210> SEQ ID NO 140
<211> LENGTH: 18
<212> TYPE: PRT
<213> ORGANISM: Artificial Sequence
<220> FEATURE:
<223> OTHER INFORMATION: C4m#19-5th4w-NN6-30

<400> SEQUENCE: 140

Gly Gly Cys Trp His Pro Phe Leu Pro Ile Met Ser Phe His Phe Cys
1 5 10 15

Pro Tyr

<210> SEQ ID NO 141
<211> LENGTH: 18
<212> TYPE: PRT
<213> ORGANISM: Artificial Sequence
<220> FEATURE:
<223> OTHER INFORMATION: C4m#19-5th4w-NN6-38

<400> SEQUENCE: 141

Gly Gly Cys Ser His Pro Phe Leu Pro Ile Phe Ser Leu His Phe Cys
1 5 10 15

Pro Val

<210> SEQ ID NO 142
<211> LENGTH: 18
<212> TYPE: PRT
<213> ORGANISM: Artificial Sequence
<220> FEATURE:
<223> OTHER INFORMATION: C4m#19-5th2w-NNS6-8

<400> SEQUENCE: 142

Gly Gly Cys Arg His Pro Phe Leu Pro Ile Phe Ser Leu His Phe Cys
1 5 10 15

Ala Arg

<210> SEQ ID NO 143
<211> LENGTH: 18
<212> TYPE: PRT
<213> ORGANISM: Artificial Sequence
<220> FEATURE:
<223> OTHER INFORMATION: C4m3127-4th-NNS6-16

<400> SEQUENCE: 143

Gly Gly Cys Trp His Pro Tyr Leu Pro Ile Phe Ser Val His Phe Cys
1 5 10 15

Pro Arg

<210> SEQ ID NO 144
<211> LENGTH: 18
<212> TYPE: PRT
<213> ORGANISM: Artificial Sequence
<220> FEATURE:
<223> OTHER INFORMATION: C4m#19-5th4w-NN6-63

<400> SEQUENCE: 144

Gly Gly Cys Trp His Pro Tyr Leu Pro Ile Leu Ser Arg His Phe Cys
1 5 10 15

Gln Ala

<210> SEQ ID NO 145
<211> LENGTH: 18
<212> TYPE: PRT
<213> ORGANISM: Artificial Sequence
<220> FEATURE:
<223> OTHER INFORMATION: C4m#19-5th4w-NN6-14

<400> SEQUENCE: 145

Gly Gly Cys Trp His Pro Phe Leu Pro Ile Arg Ser Val His Phe Cys
1               5                   10                  15

Cys Arg

<210> SEQ ID NO 146
<211> LENGTH: 18
<212> TYPE: PRT
<213> ORGANISM: Artificial Sequence
<220> FEATURE:
<223> OTHER INFORMATION: C4m#19-5th4w-NN6-1

<400> SEQUENCE: 146

Gly Gly Cys Arg His Pro Tyr Leu Pro Ile Phe Ser Ala His Phe Cys
1               5                   10                  15

Arg Ser

<210> SEQ ID NO 147
<211> LENGTH: 18
<212> TYPE: PRT
<213> ORGANISM: Artificial Sequence
<220> FEATURE:
<223> OTHER INFORMATION: C4m#19-5th4w-NN6-6

<400> SEQUENCE: 147

Gly Gly Cys Met His Pro Phe Leu Pro Ile Lys Ser Ser His Phe Cys
1               5                   10                  15

Arg Lys

<210> SEQ ID NO 148
<211> LENGTH: 18
<212> TYPE: PRT
<213> ORGANISM: Artificial Sequence
<220> FEATURE:
<223> OTHER INFORMATION: C4m#19-5th2w-NNS6-51

<400> SEQUENCE: 148

Gly Gly Cys Arg His Pro Phe Leu Pro Ile Val Ser Leu His Phe Cys
1               5                   10                  15

Pro Phe

<210> SEQ ID NO 149
<211> LENGTH: 18
<212> TYPE: PRT
<213> ORGANISM: Artificial Sequence
<220> FEATURE:
<223> OTHER INFORMATION: C4m#19-5th4w-NN6-45

<400> SEQUENCE: 149

Gly Gly Cys Arg His Pro Trp Leu Pro Ile Trp Ser Val His Phe Cys
1               5                   10                  15

Gly Val

<210> SEQ ID NO 150

<211> LENGTH: 18
<212> TYPE: PRT
<213> ORGANISM: Artificial Sequence
<220> FEATURE:
<223> OTHER INFORMATION: C4m3127-4th-NNS6-12

<400> SEQUENCE: 150

Gly Gly Cys Ser His Pro Phe Leu Pro Ile Arg Ser Arg His Phe Cys
1 5 10 15

Pro Phe

<210> SEQ ID NO 151
<211> LENGTH: 18
<212> TYPE: PRT
<213> ORGANISM: Artificial Sequence
<220> FEATURE:
<223> OTHER INFORMATION: C4m#19-5th2w-NNS6-75

<400> SEQUENCE: 151

Gly Gly Cys Trp His Pro Trp Leu Pro Ile Lys Ser Pro His Phe Cys
1 5 10 15

Ala Leu

<210> SEQ ID NO 152
<211> LENGTH: 18
<212> TYPE: PRT
<213> ORGANISM: Artificial Sequence
<220> FEATURE:
<223> OTHER INFORMATION: C4m#19-5th4w-NN6-74

<400> SEQUENCE: 152

Gly Gly Cys Phe His Pro Phe Leu Pro Ile Tyr Ser Trp His Phe Cys
1 5 10 15

Ala Arg

<210> SEQ ID NO 153
<211> LENGTH: 18
<212> TYPE: PRT
<213> ORGANISM: Artificial Sequence
<220> FEATURE:
<223> OTHER INFORMATION: C4m#19-5th4w-NN6-5-1

<400> SEQUENCE: 153

Gly Gly Cys Trp His Pro Tyr Leu Pro Ile Gln Ser Leu His Phe Cys
1 5 10 15

Pro Phe

<210> SEQ ID NO 154
<211> LENGTH: 18
<212> TYPE: PRT
<213> ORGANISM: Artificial Sequence
<220> FEATURE:
<223> OTHER INFORMATION: C4m#19-5th4w-NN6-5-3

<400> SEQUENCE: 154

Gly Gly Cys Trp His Pro Phe Leu Pro Ile Leu Ser Leu His Phe Cys
1 5 10 15

Gly Trp

<210> SEQ ID NO 155
<211> LENGTH: 18
<212> TYPE: PRT
<213> ORGANISM: Artificial Sequence
<220> FEATURE:

<223> OTHER INFORMATION: C4m#19-5th4w-NN6-46-1

<400> SEQUENCE: 155

Gly Gly Cys Val His Pro Ala Leu Pro Ile Trp Ser Phe His Phe Cys
1 5 10 15

Pro Ser

<210> SEQ ID NO 156
<211> LENGTH: 18
<212> TYPE: PRT
<213> ORGANISM: Artificial Sequence
<220> FEATURE:
<223> OTHER INFORMATION: C4m#19-5th4w-NN6-64

<400> SEQUENCE: 156

Gly Gly Cys Trp His Pro Val Leu Pro Ile Arg Ser Val His Phe Cys
1 5 10 15

Cys Arg

<210> SEQ ID NO 157
<211> LENGTH: 18
<212> TYPE: PRT
<213> ORGANISM: Artificial Sequence
<220> FEATURE:
<223> OTHER INFORMATION: C4m3127-4th-NNS6-48

<400> SEQUENCE: 157

Gly Gly Cys Phe His Pro Trp Leu Pro Ile Ala Ser Trp His Phe Cys
1 5 10 15

Gly Arg

<210> SEQ ID NO 158
<211> LENGTH: 18
<212> TYPE: PRT
<213> ORGANISM: Artificial Sequence
<220> FEATURE:
<223> OTHER INFORMATION: C4m3127-4th-NNS6-64

<400> SEQUENCE: 158

Gly Gly Cys Leu His Pro Tyr Leu Pro Ile Val Ser Ser His Phe Cys
1 5 10 15

Pro Phe

<210> SEQ ID NO 159
<211> LENGTH: 18
<212> TYPE: PRT
<213> ORGANISM: Artificial Sequence
<220> FEATURE:
<223> OTHER INFORMATION: C4m3127-4th-NNS6-80

<400> SEQUENCE: 159

Gly Gly Cys Gly His Pro Phe Leu Pro Ile Phe Ser Leu His Phe Cys
1 5 10 15

Pro Arg

<210> SEQ ID NO 160
<211> LENGTH: 18
<212> TYPE: PRT
<213> ORGANISM: Artificial Sequence
<220> FEATURE:
<223> OTHER INFORMATION: C4m3127-4th-NNS6-79

<400> SEQUENCE: 160

Gly Gly Cys Leu His Pro Phe Leu Pro Ile Arg Ser Val His Phe Cys
1 5 10 15

Leu Arg

<210> SEQ ID NO 161
<211> LENGTH: 18
<212> TYPE: PRT
<213> ORGANISM: Artificial Sequence
<220> FEATURE:
<223> OTHER INFORMATION: C4m3127-4th-NNS6-2

<400> SEQUENCE: 161

Gly Gly Cys Trp His Pro Ser Leu Pro Ile Tyr Ser Pro His Phe Cys
1 5 10 15

Pro Leu

<210> SEQ ID NO 162
<211> LENGTH: 18
<212> TYPE: PRT
<213> ORGANISM: Artificial Sequence
<220> FEATURE:
<223> OTHER INFORMATION: C4m#19-5th4w-NN6-65

<400> SEQUENCE: 162

Gly Gly Cys Trp His Pro Phe Leu Pro Ile Leu Ser Leu His Phe Cys
1 5 10 15

Ser Arg

<210> SEQ ID NO 163
<211> LENGTH: 18
<212> TYPE: PRT
<213> ORGANISM: Artificial Sequence
<220> FEATURE:
<223> OTHER INFORMATION: C4m#19-5th4w-NN6-83

<400> SEQUENCE: 163

Gly Gly Cys Leu His Pro Leu Leu Pro Ile Leu Ser Val His Phe Cys
1 5 10 15

Pro Ser

<210> SEQ ID NO 164
<211> LENGTH: 18
<212> TYPE: PRT
<213> ORGANISM: Artificial Sequence
<220> FEATURE:
<223> OTHER INFORMATION: C4m3127-4th-NNS6-60

<400> SEQUENCE: 164

Gly Gly Cys Trp His Pro Phe Leu Pro Ile Ser Ser Trp His Phe Cys
1 5 10 15

Gly Leu

<210> SEQ ID NO 165
<211> LENGTH: 18
<212> TYPE: PRT
<213> ORGANISM: Artificial Sequence
<220> FEATURE:
<223> OTHER INFORMATION: C4m#19-5th2w-NNS6-53

<400> SEQUENCE: 165

Gly Gly Cys Leu His Pro Trp Leu Pro Ile Arg Ser Phe His Phe Cys
1 5 10 15

Gly Ala

<210> SEQ ID NO 166
<211> LENGTH: 18
<212> TYPE: PRT
<213> ORGANISM: Artificial Sequence
<220> FEATURE:
<223> OTHER INFORMATION: C4m#19-5th2w-NNS6-45

<400> SEQUENCE: 166

Gly Gly Cys Arg His Pro Phe Leu Pro Ile Trp Ser Val His Phe Cys
1 5 10 15

Trp Arg

<210> SEQ ID NO 167
<211> LENGTH: 18
<212> TYPE: PRT
<213> ORGANISM: Artificial Sequence
<220> FEATURE:
<223> OTHER INFORMATION: C4m3127-4th-NNS6-3

<400> SEQUENCE: 167

Gly Gly Cys Ser His Pro Phe Leu Pro Ile Trp Ser Val His Phe Cys
1 5 10 15

Gly Gln

<210> SEQ ID NO 168
<211> LENGTH: 18
<212> TYPE: PRT
<213> ORGANISM: Artificial Sequence
<220> FEATURE:
<223> OTHER INFORMATION: C4m#19-5th2w-NNS6-6

<400> SEQUENCE: 168

Gly Gly Cys Trp His Pro Tyr Leu Pro Ile Leu Ser Leu His Phe Cys
1 5 10 15

Gln Arg

<210> SEQ ID NO 169
<211> LENGTH: 18
<212> TYPE: PRT
<213> ORGANISM: Artificial Sequence
<220> FEATURE:
<223> OTHER INFORMATION: C4m#19-5th2w-NNS6-27

<400> SEQUENCE: 169

Gly Gly Cys Phe His Pro Phe Leu Pro Ile Arg Ser Cys His Phe Cys
1 5 10 15

Ala Arg

<210> SEQ ID NO 170
<211> LENGTH: 18
<212> TYPE: PRT
<213> ORGANISM: Artificial Sequence
<220> FEATURE:
<223> OTHER INFORMATION: C4m#19-5th2w-NNS6-37

<400> SEQUENCE: 170

Gly Gly Cys Ile His Pro Phe Leu Pro Ile Trp Ser Ile His Phe Cys
1 5 10 15

Ser Arg

<210> SEQ ID NO 171
<211> LENGTH: 18

<212> TYPE: PRT
<213> ORGANISM: Artificial Sequence
<220> FEATURE:
<223> OTHER INFORMATION: C4m#19-5th2w-NNS6-33

<400> SEQUENCE: 171

Gly Gly Cys Arg His Pro Phe Leu Pro Ile Trp Ser Phe His Phe Cys
1 5 10 15

Trp Gly

<210> SEQ ID NO 172
<211> LENGTH: 18
<212> TYPE: PRT
<213> ORGANISM: Artificial Sequence
<220> FEATURE:
<223> OTHER INFORMATION: C4m#19-5th2w-NNS6-79

<400> SEQUENCE: 172

Gly Gly Cys Arg His Pro Phe Leu Pro Ile Val Ser Arg His Phe Cys
1 5 10 15

Val Ala

<210> SEQ ID NO 173
<211> LENGTH: 18
<212> TYPE: PRT
<213> ORGANISM: Artificial Sequence
<220> FEATURE:
<223> OTHER INFORMATION: C4m3127-4th-NNS6-85

<400> SEQUENCE: 173

Gly Gly Cys Gly His Pro Phe Leu Pro Ile Phe Ser Ser His Phe Cys
1 5 10 15

Pro Leu

<210> SEQ ID NO 174
<211> LENGTH: 18
<212> TYPE: PRT
<213> ORGANISM: Artificial Sequence
<220> FEATURE:
<223> OTHER INFORMATION: C4m#19-5th2w-NNS6-30

<400> SEQUENCE: 174

Gly Gly Cys Trp His Pro Phe Leu Pro Ile Leu Ser Trp His Phe Cys
1 5 10 15

Gly Arg

<210> SEQ ID NO 175
<211> LENGTH: 18
<212> TYPE: PRT
<213> ORGANISM: Artificial Sequence
<220> FEATURE:
<223> OTHER INFORMATION: C4m#19-5th4w-NN6-89

<400> SEQUENCE: 175

Gly Gly Cys Met His Pro Phe Leu Pro Ile Ile Ser Gln His Phe Cys
1 5 10 15

Ala Phe

<210> SEQ ID NO 176
<211> LENGTH: 18
<212> TYPE: PRT
<213> ORGANISM: Artificial Sequence
<220> FEATURE:
<223> OTHER INFORMATION: C4m#19-5th2w-NNS6-86

<400> SEQUENCE: 176

Gly Gly Cys Phe His Pro Tyr Leu Pro Ile Trp Ser Leu His Phe Cys
1 5 10 15

Arg Ser

<210> SEQ ID NO 177
<211> LENGTH: 18
<212> TYPE: PRT
<213> ORGANISM: Artificial Sequence
<220> FEATURE:
<223> OTHER INFORMATION: C4m3127-4th-NNS6-30

<400> SEQUENCE: 177

Gly Gly Cys Trp His Pro Cys Leu Pro Ile Leu Ser Pro His Phe Cys
1 5 10 15

Pro Arg

<210> SEQ ID NO 178
<211> LENGTH: 18
<212> TYPE: PRT
<213> ORGANISM: Artificial Sequence
<220> FEATURE:
<223> OTHER INFORMATION: C4m3127-4th-NNS6-26

<400> SEQUENCE: 178

Gly Gly Cys Ala His Pro Ala Leu Pro Ile Trp Ser Cys His Phe Cys
1 5 10 15

Pro Phe

<210> SEQ ID NO 179
<211> LENGTH: 18
<212> TYPE: PRT
<213> ORGANISM: Artificial Sequence
<220> FEATURE:
<223> OTHER INFORMATION: C4m#19-5th2w-NNS6-74

<400> SEQUENCE: 179

Gly Gly Cys Met His Pro Phe Leu Pro Ile Arg Ser Trp His Phe Cys
1 5 10 15

Ser Arg

<210> SEQ ID NO 180
<211> LENGTH: 18
<212> TYPE: PRT
<213> ORGANISM: Artificial Sequence
<220> FEATURE:
<223> OTHER INFORMATION: C4m3127-4th-NNS6-89

<400> SEQUENCE: 180

Gly Gly Cys Trp His Pro Phe Leu Pro Ile Phe Ser Ala His Phe Cys
1 5 10 15

Met Arg

<210> SEQ ID NO 181
<211> LENGTH: 18
<212> TYPE: PRT
<213> ORGANISM: Artificial Sequence
<220> FEATURE:
<223> OTHER INFORMATION: C4m#19-5th2w-NNS6-84

<400> SEQUENCE: 181

Gly Gly Cys Trp His Pro Phe Leu Pro Ile Val Ser Phe His Phe Cys 1 5 10 15

Pro Phe

<210> SEQ ID NO 182
<211> LENGTH: 18
<212> TYPE: PRT
<213> ORGANISM: Artificial Sequence
<220> FEATURE:
<223> OTHER INFORMATION: C4m#19-5th2w-NNS6-28

<400> SEQUENCE: 182

Gly Gly Cys Ala His Pro Tyr Leu Pro Ile Arg Ser Val His Phe Cys
1 5 10 15

Pro Cys

<210> SEQ ID NO 183
<211> LENGTH: 18
<212> TYPE: PRT
<213> ORGANISM: Artificial Sequence
<220> FEATURE:
<223> OTHER INFORMATION: C4m#19-5th2w-NNS6-4

<400> SEQUENCE: 183

Gly Gly Cys Phe His Pro Trp Leu Pro Ile Ser Ser Leu His Phe Cys
1 5 10 15

Pro Phe

<210> SEQ ID NO 184
<211> LENGTH: 18
<212> TYPE: PRT
<213> ORGANISM: Artificial Sequence
<220> FEATURE:
<223> OTHER INFORMATION: C4m#19-5th2w-NNS6-46

<400> SEQUENCE: 184

Gly Gly Cys Phe His Pro Phe Leu Pro Ile Phe Ser Tyr His Phe Cys
1 5 10 15

Gly Leu

<210> SEQ ID NO 185
<211> LENGTH: 18
<212> TYPE: PRT
<213> ORGANISM: Artificial Sequence
<220> FEATURE:
<223> OTHER INFORMATION: C4m#19-5th4w-NN6-61

<400> SEQUENCE: 185

Gly Gly Cys Pro His Pro Met Leu Pro Ile Phe Ser Val His Phe Cys
1 5 10 15

Pro Tyr

<210> SEQ ID NO 186
<211> LENGTH: 18
<212> TYPE: PRT
<213> ORGANISM: Artificial Sequence
<220> FEATURE:
<223> OTHER INFORMATION: C4m3127-4th-NNS6-94

<400> SEQUENCE: 186

Gly Gly Cys Arg His Pro Val Leu Pro Ile Trp Ser Ser His Phe Cys
1 5 10 15

Pro Trp

<210> SEQ ID NO 187
<211> LENGTH: 18
<212> TYPE: PRT
<213> ORGANISM: Artificial Sequence
<220> FEATURE:
<223> OTHER INFORMATION: C4m#19-5th2w-NNS6-26

<400> SEQUENCE: 187

Gly Gly Cys Leu His Pro Phe Leu Pro Ile Val Ser Ile His Phe Cys
1 5 10 15

Ser Ala

<210> SEQ ID NO 188
<211> LENGTH: 18
<212> TYPE: PRT
<213> ORGANISM: Artificial Sequence
<220> FEATURE:
<223> OTHER INFORMATION: C4m#19-5th4w-NN6-36

<400> SEQUENCE: 188

Gly Gly Cys Arg His Pro Tyr Leu Pro Ile Trp Ser Ala His Phe Cys
1 5 10 15

Cys Arg

<210> SEQ ID NO 189
<211> LENGTH: 18
<212> TYPE: PRT
<213> ORGANISM: Artificial Sequence
<220> FEATURE:
<223> OTHER INFORMATION: C4m#19-5th4w-NN6-75

<400> SEQUENCE: 189

Gly Gly Cys Trp His Pro Phe Leu Pro Ile Lys Ser Val His Phe Cys
1 5 10 15

Cys Ala

<210> SEQ ID NO 190
<211> LENGTH: 18
<212> TYPE: PRT
<213> ORGANISM: Artificial Sequence
<220> FEATURE:
<223> OTHER INFORMATION: C4m#19-5th2w-NNS6-70

<400> SEQUENCE: 190

Gly Gly Cys Arg His Pro Phe Leu Pro Ile Val Ser Trp His Phe Cys
1 5 10 15

Ala Ala

<210> SEQ ID NO 191
<211> LENGTH: 18
<212> TYPE: PRT
<213> ORGANISM: Artificial Sequence
<220> FEATURE:
<223> OTHER INFORMATION: C4m#19-5th2w-NNS6-34

<400> SEQUENCE: 191

Gly Gly Cys Cys His Pro Phe Leu Pro Ile Tyr Ser Val His Phe Cys
1 5 10 15

Ala Ser

<210> SEQ ID NO 192
<211> LENGTH: 18
<212> TYPE: PRT

<213> ORGANISM: Artificial Sequence
<220> FEATURE:
<223> OTHER INFORMATION: C4m#19-5th4w-NN6-94

<400> SEQUENCE: 192

Gly Gly Cys Leu His Pro Phe Leu Pro Ile Tyr Ser Leu His Phe Cys
1 5 10 15

Pro Cys

<210> SEQ ID NO 193
<211> LENGTH: 18
<212> TYPE: PRT
<213> ORGANISM: Artificial Sequence
<220> FEATURE:
<223> OTHER INFORMATION: C4m3127-4th-NNS6-66

<400> SEQUENCE: 193

Gly Gly Cys Ala His Pro His Leu Pro Ile Arg Ser Val His Phe Cys
1 5 10 15

Ser Phe

<210> SEQ ID NO 194
<211> LENGTH: 18
<212> TYPE: PRT
<213> ORGANISM: Artificial Sequence
<220> FEATURE:
<223> OTHER INFORMATION: C4m#19-5th2w-NNS6-43

<400> SEQUENCE: 194

Gly Gly Cys Arg His Pro Phe Leu Pro Ile Trp Ser Ser His Phe Cys
1 5 10 15

Ala Ala

<210> SEQ ID NO 195
<211> LENGTH: 18
<212> TYPE: PRT
<213> ORGANISM: Artificial Sequence
<220> FEATURE:
<223> OTHER INFORMATION: C4m3127-4th-NNS6-7

<400> SEQUENCE: 195

Gly Gly Cys Arg His Pro Phe Leu Pro Ile Arg Ser Pro His Phe Cys
1 5 10 15

Gly Ser

<210> SEQ ID NO 196
<211> LENGTH: 18
<212> TYPE: PRT
<213> ORGANISM: Artificial Sequence
<220> FEATURE:
<223> OTHER INFORMATION: C4m#19-5th4w-NN6-72

<400> SEQUENCE: 196

Gly Gly Cys Trp His Pro Trp Leu Pro Ile Val Ser Val His Phe Cys
1 5 10 15

Gly Cys

<210> SEQ ID NO 197
<211> LENGTH: 18
<212> TYPE: PRT
<213> ORGANISM: Artificial Sequence
<220> FEATURE:
<223> OTHER INFORMATION: C4m3127-4th-NNS6-70

<400> SEQUENCE: 197

Gly Gly Cys Ser His Pro Tyr Leu Pro Ile His Ser Arg His Phe Cys
1 5 10 15

Leu Ser

<210> SEQ ID NO 198
<211> LENGTH: 18
<212> TYPE: PRT
<213> ORGANISM: Artificial Sequence
<220> FEATURE:
<223> OTHER INFORMATION: C4m#19-5th2w-NNS6-68

<400> SEQUENCE: 198

Gly Gly Cys Leu His Pro Trp Leu Pro Ile Val Ser Cys His Phe Cys
1 5 10 15

Pro Arg

<210> SEQ ID NO 199
<211> LENGTH: 18
<212> TYPE: PRT
<213> ORGANISM: Artificial Sequence
<220> FEATURE:
<223> OTHER INFORMATION: C4m#19-5th2w-NNS6-87

<400> SEQUENCE: 199

Gly Gly Cys Leu His Pro Tyr Leu Pro Ile Phe Ser Val His Phe Cys
1 5 10 15

Ala Leu

<210> SEQ ID NO 200
<211> LENGTH: 18
<212> TYPE: PRT
<213> ORGANISM: Artificial Sequence
<220> FEATURE:
<223> OTHER INFORMATION: C4m#19-5th2w-NNS6-66

<400> SEQUENCE: 200

Gly Gly Cys Arg His Pro Phe Leu Pro Ile Phe Ser Val His Phe Cys
1 5 10 15

Pro Phe

<210> SEQ ID NO 201
<211> LENGTH: 18
<212> TYPE: PRT
<213> ORGANISM: Artificial Sequence
<220> FEATURE:
<223> OTHER INFORMATION: C4m3127-4th-NNS6-20

<400> SEQUENCE: 201

Gly Gly Cys Leu His Pro Phe Leu Pro Ile Leu Ser Leu His Phe Cys
1 5 10 15

Pro Phe

<210> SEQ ID NO 202
<211> LENGTH: 18
<212> TYPE: PRT
<213> ORGANISM: Artificial Sequence
<220> FEATURE:
<223> OTHER INFORMATION: C4m#19-5th2w-NNS6-61

<400> SEQUENCE: 202

Gly Gly Cys Cys His Pro Trp Leu Pro Ile Arg Ser Val His Phe Cys
1 5 10 15

Pro Phe

<210> SEQ ID NO 203
<211> LENGTH: 18
<212> TYPE: PRT
<213> ORGANISM: Artificial Sequence
<220> FEATURE:
<223> OTHER INFORMATION: C4m3127-4th-NNS6-19

<400> SEQUENCE: 203

Gly Gly Cys Met His Pro Ser Leu Pro Ile Trp Ser Trp His Phe Cys
1 5 10 15

Pro His

<210> SEQ ID NO 204
<211> LENGTH: 18
<212> TYPE: PRT
<213> ORGANISM: Artificial Sequence
<220> FEATURE:
<223> OTHER INFORMATION: C4m#19-5th4w-NN6-40

<400> SEQUENCE: 204

Gly Gly Cys Phe His Pro Phe Leu Pro Ile Arg Ser His His Phe Cys
1 5 10 15

Met Leu

<210> SEQ ID NO 205
<211> LENGTH: 18
<212> TYPE: PRT
<213> ORGANISM: Artificial Sequence
<220> FEATURE:
<223> OTHER INFORMATION: C4m#19-5th4w-NN6-49

<400> SEQUENCE: 205

Gly Gly Cys Met His Pro Tyr Leu Pro Ile Arg Ser Phe His Phe Cys
1 5 10 15

Ser Cys

<210> SEQ ID NO 206
<211> LENGTH: 18
<212> TYPE: PRT
<213> ORGANISM: Artificial Sequence
<220> FEATURE:
<223> OTHER INFORMATION: C4m#19-5th4w-NN6-80

<400> SEQUENCE: 206

Gly Gly Cys Arg His Pro Phe Leu Pro Ile Phe Ser Trp His Phe Cys
1 5 10 15

Ala Val

<210> SEQ ID NO 207
<211> LENGTH: 18
<212> TYPE: PRT
<213> ORGANISM: Artificial Sequence
<220> FEATURE:
<223> OTHER INFORMATION: C4m#19-5th2w-NNS6-80

<400> SEQUENCE: 207

Gly Gly Cys Leu His Pro Phe Leu Pro Ile Val Ser Trp His Phe Cys
1 5 10 15

Pro Cys

<210> SEQ ID NO 208
<211> LENGTH: 18
<212> TYPE: PRT
<213> ORGANISM: Artificial Sequence
<220> FEATURE:
<223> OTHER INFORMATION: C4m3127-4th-NNS6-37

<400> SEQUENCE: 208

Gly Gly Cys Trp His Pro Val Leu Pro Ile Arg Ser Ile His Phe Cys
1 5 10 15

Gly Cys

<210> SEQ ID NO 209
<211> LENGTH: 18
<212> TYPE: PRT
<213> ORGANISM: Artificial Sequence
<220> FEATURE:
<223> OTHER INFORMATION: C4m#19-5th2w-NNS6-93

<400> SEQUENCE: 209

Gly Gly Cys Phe His Pro Phe Leu Pro Ile Gln Ser Arg His Phe Cys
1 5 10 15

Cys Arg

<210> SEQ ID NO 210
<211> LENGTH: 18
<212> TYPE: PRT
<213> ORGANISM: Artificial Sequence
<220> FEATURE:
<223> OTHER INFORMATION: C4m3127-4th-NNS6-95

<400> SEQUENCE: 210

Gly Gly Cys Trp His Pro Val Leu Pro Ile Arg Ser Gly His Phe Cys
1 5 10 15

Ser Arg

<210> SEQ ID NO 211
<211> LENGTH: 18
<212> TYPE: PRT
<213> ORGANISM: Artificial Sequence
<220> FEATURE:
<223> OTHER INFORMATION: C4m#19-5th2w-NNS6-41

<400> SEQUENCE: 211

Gly Gly Cys Trp His Pro Val Leu Pro Ile Arg Ser Asp His Phe Cys
1 5 10 15

Cys Arg

<210> SEQ ID NO 212
<211> LENGTH: 12
<212> TYPE: PRT
<213> ORGANISM: Artificial Sequence
<220> FEATURE:
<223> OTHER INFORMATION: artificial peptide with randomized amino acids
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:

<221> NAME/KEY: misc_feature
<222> LOCATION: (10)..(10)
<223> OTHER INFORMATION: Xaa can be any naturally occurring amino acid

<400> SEQUENCE: 212

Xaa His Pro Xaa Leu Xaa Xaa Xaa Ser Xaa His Phe
1 5 10

<210> SEQ ID NO 213
<211> LENGTH: 14
<212> TYPE: PRT
<213> ORGANISM: Artificial Sequence
<220> FEATURE:
<223> OTHER INFORMATION: artificial peptide with randomized amino acids
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 213

Xaa Xaa His Pro Xaa Leu Xaa Xaa Xaa Ser Xaa His Phe Xaa
1 5 10

<210> SEQ ID NO 214
<211> LENGTH: 16
<212> TYPE: PRT
<213> ORGANISM: Artificial Sequence
<220> FEATURE:
<223> OTHER INFORMATION: artificial peptide with randomized amino acids
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid

<400> SEQUENCE: 214

Xaa Xaa Xaa His Pro Xaa Leu Xaa Xaa Xaa Ser Xaa His Phe Xaa Xaa
1 5 10 15

<210> SEQ ID NO 215
<211> LENGTH: 14
<212> TYPE: PRT

<213> ORGANISM: Artificial Sequence
<220> FEATURE:
<223> OTHER INFORMATION: artificial cyclic peptide with randomized amino acids
<220> FEATURE:
<221> NAME/KEY: DISULFID
<222> LOCATION: (1)..(14)
<220> FEATURE:
<221> NAME/KEY: MISC_FEATURE
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..(9)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: Xaa can be any naturally occurring amino acid

<400> SEQUENCE: 215

```
Cys Xaa His Pro Xaa Leu Xaa Xaa Xaa Ser Xaa His Phe Cys
1               5                   10
```

<210> SEQ ID NO 216
<211> LENGTH: 16
<212> TYPE: PRT
<213> ORGANISM: Artificial Sequence
<220> FEATURE:
<223> OTHER INFORMATION: artificial cyclic peptide with randomized amino acids
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: DISULFID
<222> LOCATION: (2)..(15)
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (8)..(10)
<223> OTHER INFORMATION: Xaa can be any naturally occurring amino acid
<220> FEATURE:
<221> NAME/KEY: MISC_FEATURE
<222> LOCATION: (12)..(12)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 216

```
Xaa Cys Xaa His Pro Xaa Leu Xaa Xaa Xaa Ser Xaa His Phe Cys Xaa
1               5                   10                  15
```

<210> SEQ ID NO 217
<211> LENGTH: 12
<212> TYPE: PRT
<213> ORGANISM: Artificial Sequence
<220> FEATURE:
<223> OTHER INFORMATION: artificial peptide with randomized amino acids
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 217

Xaa His Pro Xaa Leu Pro Ile Xaa Ser Xaa His Phe
1 5 10

<210> SEQ ID NO 218
<211> LENGTH: 14
<212> TYPE: PRT
<213> ORGANISM: Artificial Sequence
<220> FEATURE:
<223> OTHER INFORMATION: artificial peptide with randomized amino acids
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 218

Xaa Xaa His Pro Xaa Leu Pro Ile Xaa Ser Xaa His Phe Xaa
1 5 10

<210> SEQ ID NO 219
<211> LENGTH: 16
<212> TYPE: PRT
<213> ORGANISM: Artificial Sequence
<220> FEATURE:
<223> OTHER INFORMATION: artificial peptide with randomized amino acids
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(16)

<223> OTHER INFORMATION: Xaa can be any naturally occurring amino acid

<400> SEQUENCE: 219

Xaa Xaa Xaa His Pro Xaa Leu Pro Ile Xaa Ser Xaa His Phe Xaa Xaa
1 5 10 15

<210> SEQ ID NO 220
<211> LENGTH: 14
<212> TYPE: PRT
<213> ORGANISM: Artificial Sequence
<220> FEATURE:
<223> OTHER INFORMATION: artificial cyclic peptide with randomized amino acids
<220> FEATURE:
<221> NAME/KEY: DISULFID
<222> LOCATION: (1)..(14)
<220> FEATURE:
<221> NAME/KEY: MISC_FEATURE
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: Xaa can be any naturally occurring amino acid

<400> SEQUENCE: 220

Cys Xaa His Pro Xaa Leu Pro Ile Xaa Ser Xaa His Phe Cys
1 5 10

<210> SEQ ID NO 221
<211> LENGTH: 16
<212> TYPE: PRT
<213> ORGANISM: Artificial Sequence
<220> FEATURE:
<223> OTHER INFORMATION: artificial cyclic peptide with randomized amino acids
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: DISULFID
<222> LOCATION: (2)..(15)
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (12)..(12)

-continued

```
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 221

Xaa Cys Xaa His Pro Xaa Leu Pro Ile Xaa Ser Xaa His Phe Cys Xaa
1               5                   10                  15
```

CYCLIC PEPTIDE HAVING CTLA-4 INHIBITORY ACTIVITY AND USE THEREOF

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 70,534 bytes ASCII (Text) file named "762818Sequence-Listing-Replacement.txt," created Sep. 22, 2025.

TECHNICAL FIELD

The present invention relates to a cyclic peptide that inhibits the binding of CTLA-4 to CD80/CD86, and uses thereof.

BACKGROUND ART

Small molecule drugs, which have been the core of conventional pharmaceuticals, have a problem that, for example, they are prone to cause toxicity and side effects due to their low specificity for the target molecule, and they are unsuitable for inhibiting protein-protein interactions due to their small molecular size. In addition, antibody drugs, which are developed by many pharmaceutical companies in recent years, have a problem that the application to intracellular target molecules is difficult because they do not easily enter cells, they are difficult to be administered orally, and manufacturing cost is high. Therefore, middle molecule drugs based on peptides are being developed recently, as an ideal drug that compensates for the problems of both small molecule drugs and antibody drugs (Non-Patent Document 1).

Cyclic peptides are known to have superior specificity to target molecules, stability, and membrane permeability than linear peptides (Non-Patent Document 2). Cyclic peptides with desired activity can be efficiently obtained by in vitro selection experiments such as phage display (Non-Patent Document 3), mRNA display (Non-Patent Documents 4 and 5) or the like. Cyclic peptides with desired activity can also be prepared enzymatically and selected in a cell (Non-Patent Document 6).

Ribosome display (Patent Document 1) is one of the in vitro selection methods, as well as phage display and mRNA display. Recently, the inventors have developed a novel ribosome display system using the PUREsystem, a cell-free translation system in which factors required for translation are individually prepared and reconstituted, and further optimized for ribosome display (Patent Document 2). In this ribosome display system, the concentration of oxidants and reductants optimal for S—S bond formation can be freely set, and various molecular chaperones (e.g., DsbC, PDI, GroEL-ES, DnaK and the like) can be added or combined.

Immune checkpoint molecules such as CTLA-4 (cytotoxic T-lymphocyte-associated protein 4) and PD-1 (programmed death 1) are negative regulators of T cell immune function. Inhibition of the function of these molecules results in activation of the immune system and is clinically applied as a therapeutic drug. As for CTLA-4, it was shown that an anti-CTLA-4 antibody inhibits the interaction between CTLA-4 and CD80/CD86 and suppresses cancer growth (Non-Patent Document 7). However, no middle-molecule drugs that inhibit CTLA-4 function have yet been developed.

DOCUMENT LIST

Patent Documents

Patent Document 1: JP2008-271903A

Patent Document 2: US patent application publication No. 2012/231496 specification

Non-Patent Documents

Non-Patent Document 1: Zorzi, A. et al., Curr. Opin. Chem. Biol., (2017), 38, 24-29

Non-Patent Document 2: Roxin, A. and Zheng, G., Future Med. Chem., (2012), 4(12), 1601-1618

Non-Patent Document 3: Desimmie, B. A. et al., Molecular Therapy, (2012), 20(11), 2064-2075

Non-Patent Document 4: Guillen Schlippe, Y. V. et al., J. Am. Chem. Soc., (2012), 134, 10469-10477

Non-Patent Document 5: Bashiruddin, N. K. and Suga, H., Curr. Opin. Chem. Biol., (2015), 24, 131-138

Non-Patent Document 6: Tavassoli, A., Curr. Opin. Chem. Biol., (2017), 38, 30-35

Non-Patent Document 7: Leach, D. R. et al., Science, (1996), 271(5256), 1734-1736

SUMMARY OF THE INVENTION

Problems to be Solved by the Invention

The purpose of the present invention is to provide a cyclic peptide that inhibit CTLA-4 function.

Means of Solving the Problems

The present inventors succeeded in obtaining multiple cyclic peptides that bind specifically to CTLA-4 by performing selection experiments by ribosome display under a condition optimized for S—S bond formation between two cysteines in a cyclic peptide. These cyclic peptides inhibited the interaction between CTLA-4 and CD80. Affinity Maturation was performed to obtain many high-affinity CTLA-4 binders. Furthermore, Alanine scanning was performed to successively identify the minimal amino acid residues required for binding to CTLA-4. Based on these findings, the present inventors have investigated further and completed the present invention.

Accordingly, the present invention relates to the followings.

[1] A cyclic peptide which comprises the amino acid sequence represented by formula (I):

$X_1$-His-Pro-$X_4$-Leu-$X_6$-$X_7$-$X_8$-Ser-$X_{10}$-His-PheI (SEQ ID NO: 212)

in the cycle and has an activity to specifically bind to human CTLA-4, wherein $X_1$, $X_4$, $X_6$, $X_7$, $X_8$ and $X_{10}$ are each independently any amino acid.

[2] The cyclic peptide according to [1], wherein the cyclic peptide comprises the amino acid sequence represented by formula (II):

$X_0$-$X_1$-His-Pro-$X_4$-Leu-$X_6$-$X_7$-$X_8$-Ser-$X_{10}$-His-Phe-$X_{00}$ (II) (SEQ ID NO: 213)

wherein $X_1$, $X_4$, $X_6$, $X_7$, $X_8$ and $X_{10}$ are synonymous with those defined in formula (I), $X_0$ and $X_{00}$ are each independently any amino acid, and wherein the peptide is cyclized by an intramolecular bond between $X_0$ and $X_{00}$.

[3] The cyclic peptide according to [2], wherein the cyclic peptide comprises the amino acid sequence represented by formula (III):

(Y)*m*-$X_0$-$X_1$-His-Pro-$X_4$-Leu-$X_6$-$X_7$-$X_8$-Ser-$X_{10}$-His-Phe-$X_{00}$-(Z)*n* (III) (SEQ ID NO: 214)

wherein $X_0$, $X_1$, $X_4$, $X_6$, $X_7$, $X_8$, $X_{10}$ and $X_{00}$ are synonymous with those defined in formula (II), (Y)m is an amino acid sequence having a length of m amino acid(s), (Z)n is an amino acid sequence having a length of n amino acid(s), m is any integer selected from the group consisting of 0, 1 and 2, and n is any integer selected from the group consisting of 0, 1 and 2.

[4] The cyclic peptide according to [2] or [3], wherein $X_0$ and $X_{00}$ are each independently an amino acid having a side chain containing a thiol group.

[5] The cyclic peptide according to [4], wherein $X_0$ is Cys, and $X_{00}$ is Cys.

[6] The cyclic peptide according to [4] or [5], wherein the peptide is cyclized by an intramolecular disulfide bond between a thiol group in the side chain of $X_0$ and a thiol group in the side chain of $X_{00}$.

[7] The cyclic peptide according to any of [1] to [6], wherein $X_6$ is Leu, Pro, Gln, Lys or Arg, and $X_7$ is Val, Leu, Ile or Thr.

[8] The cyclic peptide according to [7], wherein $X_6$ is Pro, and $X_7$ is Ile.

[9] The cyclic peptide according to any of [3] to [8], wherein n is 2, (Z)n consists of an amino acid sequence represented by $X_{+1}$-$X_{+2}$, and $X_{+1}$ and $X_{+2}$ are each independently any amino acid.

[10] The cyclic peptide according to any of [3] to [9], wherein m is 2, (Y)m consists of an amino acid sequence represented by $X_{-2}$-$X_{-1}$, and $X_{-2}$ and $X_{-1}$ are each independently any amino acid.

[11] The cyclic peptide according to [10], wherein $X_{-2}$ is Gly, and $X_{-1}$ is Gly, Ser or Asp.

[12] The cyclic peptide according to any of [1] to [11], wherein the amino acid sequence represented by formula (I) consists of (1a) an amino acid sequence from position 4 to position 15 in the amino acid sequence represented by any of SEQ ID NOs: 30-211, or (2a) an amino acid sequence having a substitution at least at one amino acid corresponding to one selected from $X_1$, $X_4$, $X_6$, $X_7$, $X_8$ and $X_{10}$ in an amino acid sequence from position 4 to position 15 in the amino acid sequence represented by any of SEQ ID NOs: 30-211.

[13] The cyclic peptide according to any of [2] to [12], wherein the amino acid sequence represented by formula (II) consists of (1b) an amino acid sequence from position 3 to position 16 in the amino acid sequence represented by any of SEQ ID NOs: 30-211, or (2b) an amino acid sequence having a substitution at least at one amino acid corresponding to one selected from $X_1$, $X_4$, $X_6$, $X_7$, $X_8$ and $X_{10}$ in an amino acid sequence from position 3 to position 16 in the amino acid sequence represented by any of SEQ ID NOs: 30-211

[14] The cyclic peptide according to any of [3] to [13], wherein the amino acid sequence represented by formula (III) consists of (1c) the amino acid sequence represented by any of SEQ ID NOs: 30-211, or (2c) an amino acid sequence having a substitution at least at one amino acid corresponding to one selected from X-2, X-1, $X_1$, $X_4$, $X_6$, $X_7$, $X_8$, $X_{10}$, $X_{+1}$ and $X_{+2}$ in the amino acid sequence represented by any of SEQ ID NOs: 30-211.

[15] The cyclic peptide according to any of [1] to [14], wherein the cyclic peptide has an activity to inhibit the interaction between human CTLA-4 and human CD80.

[16] A pharmaceutical composition which comprises the cyclic peptide according to any of

[1] to [14] and a pharmaceutically acceptable carrier or excipient.

[17] The pharmaceutical composition according to [16], which is for inhibiting CTLA-4.

[18] The pharmaceutical composition according to [16], which is for activating T cells.

[19] The pharmaceutical composition according to [16], which is for preventing or treating a tumor.

[20] A CTLA-4 inhibitor, which comprises the cyclic peptide according to any of [1] to [15].

[21] A method for preventing or treating a tumor in a subject, which comprises administering an effective amount of the cyclic peptide according to any of [1] to [15] to the subject.

[22] The cyclic peptide according to any of [1] to [15], which is for use in preventing or treating a tumor.

[23] Use of the cyclic peptide according to any of [1] to [15], for manufacturing a pharmaceutical composition for preventing or treating a tumor.

Effect of the Invention

According to the present invention, a cyclic peptide which inhibits CTLA-4 function is provided. The cyclic peptide of the present invention is useful as an immune checkpoint inhibitor and expected to be applied for a prophylactic or therapeutic drug against diseases (e.g., cancer) which can be treated or prevented by inhibiting CTLA-4 function.

MODE FOR CARRYING OUT THE INVENTION

I. Definition

<Peptide>

Figure 1:
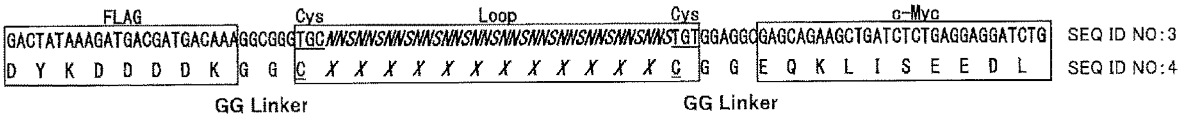
FIG. 1 Sequence information of the cyclic peptide random library is shown. 5'FLAG tag sequence and 3'c-Myc tag sequence are indicated by a rectangle frame, and a random sequence (NNS) is indicated by italic type. Two cysteine residues are underlined. GG Linker means a linker consisting of two glycine residues.

As used herein, the terms "peptide", "oligopeptide", "polypeptide" and "protein" are used interchangeably and mean a polymer of amino acids of any length. The polymer may be linear, branched or cyclic.

<Amino Acid>

As used herein, the term "amino acid" is used in the broadest sense and encompasses not only natural amino acids but also artificial amino acid variants or derivatives thereof. For example, natural proteinogenic amino acid, non-proteinogenic amino acid, and chemically synthesized compounds having properties known in the art as characteristics of an amino acid are encompassed within the term "amino acid". Although each amino acid may have L-form or D-form configuration as appropriate, typically L-form configuration is used for all amino acids. The amino acids may be represented by a commonly used three-letter or single-letter abbreviation. Except when preceded by "D", an amino acid refers to an L-amino acid. When the position of the amino group substitution is not particularly specified, an amino acid refers to an α-amino acid. L-amino acids are indicated by a single capital letter or the first capital letter in the three-letter symbol, and D-amino acids are indicated by a single lowercase letter or a lowercase three-letter symbol.

Natural proteinogenic amino acids include alanine (A or Ala), cysteine (C or Cys), aspartic acid (D or Asp), glutamic acid (E or Glu), phenylalanine (F or Phe), glycine (G or Gly), histidine (H or His), isoleucine (I or Ile), lysine (K or Lys), leucine (L or Leu), methionine (M or Met), asparagine (N or Asn), proline (P or Pro), glutamine (Q or Gln), arginine (R or Arg), serine (S or Ser), threonine (T or Thr), valine (V or Val), tryptophan (W or Trp) and tyrosine (Y or Tyr).

Non-proteinogenic amino acids refer to natural or non-natural amino acids other than natural proteinogenic amino acids. As examples of the non-proteinogenic amino acid, the followings can be exemplified:

1. Isomers of Natural Proteinogenic Amino Acids (1) Enantiomers (D-Amino Acids)

For example, D-alanine (a or ala), D-cysteine (c or cys), D-aspartic acid (d or asp), D-glutamic acid (e or glu), D-phenylalanine (f or phe), D-histidine (h or his), D-isoleucine (i or ile), D-lysine (k or lys), D-leucine (l or leu), D-methionine (m or met), D-asparagine (n or asn), D-proline (p or pro), D-glutamine (q or gln), D-arginine (r or arg), D-serine (s or ser), D-threonine (t or thr), D-valine (v or val), D-tryptophan (w or trp) and D-tyrosine (y or tyr) can be mentioned.

(2) Diastereomers

For example, allothreonine (alThr) (L-form or D-form) and alloisoleucine (AIle) (L-form or D-form) can be mentioned.

(3) Amino acids having an amino group on a carbon other than α-position (β-amino acids, γ-amino acids or the like)

For example, β-alanine (bAla), β-leucine (bLeu), β-methionine (bMet), β-phenylalanine (bPhe), β-tyrosine (bTyr), β-cysteine (bCys), β-serine (bSer), β-threonine (bThr), β-asparagine (bAsn), β-glutamine (bGln), β-aspartic acid (bAsp), β-glutamic acid (bGlu), β-lysine (bLys), β-arginine (bArg), β-histidine (bHis) can be mentioned.

(4) Amino Acids Peptide-Bonded at the β-Position of Carboxylic Acid

For example, isoaspartic acid (iAsp) and isoglutamic acid (iGlu) can be mentioned.

(5) Side Chain Isomers

For example, norleucine (Nle), tert-leucine (Tle) and norvaline (Nva) can be mentioned.

2. Substituted Natural Proteinogenic Amino Acids (1) Amino Acids Having an Additional Alkylene Group in the Main Chain The alkylene group is preferably a linear alkylene group having 1 to 4 carbon atoms. In the case of the alkylene group having one carbon atom (i.e., methylene group), the substituted natural proteinogenic amino acid may be a β-homo amino acid. Examples of the β-homo amino acid include β-homoalanine (Bha), β-homovaline (Bhv), β-homoleucine (Bhl), β-homoisoleucine (Bhi), β-homomethionine (Bhm), β-homophenylalanine (Bhf), β-homotryptophane (Bhw), β-homotyrosine (Bhy), β-homocysteine (Bhc), β-homoserine (Bhs), β-homothreonine (Bht), β-homoasparagine (Bhn), β-homoglutamine (Bhq), β-homoaspartic acid (Bhe), β-homoglutamine acid (Bhe), β-homolysine (Bhk), β-homoarginine (Bhr), β-homohistidine (Bhh) or the like.

In the case of the alkylene group other than methylene group, 3-aminobutyric acid (3Abu), 4-aminobutyric acid (4Abu), 6-aminohexanoic acid (εAhx), 5-aminopentanoic acid (δAva) or the like can be exemplified.

(2) Amino Acids Having a Substituent at a Nitrogen Atom in the Main Chain (N-Substituted Amino Acids)

Although the kinds of substituents are not particularly limited, an alkyl group and formyl group can be exemplified. The alkyl group is preferably a linear or branched alkyl group having 1 to 6 carbon atoms, and examples of the linear C1-6 alkyl group include methyl group, ethyl group, n-propyl group, n-butyl group, n-pentyl group and n-hexyl group. Examples of the branched C1-6 alkyl group include isopropyl, isobutyl, sec-butyl, tert-butyl, isopentyl, neo-pentyl, 1-ethylpropyl, isohexyl, 1,1-dimethylbutyl, 2,2-dimethylbutyl, 3,3-dimethylbutyl, 2-ethylbutyl or the like. The alkyl group may be substituted by amino group, hydroxy group, thiol group or the like.

Examples of the N-substituted amino acid include N-methylglycine (sarcosine), N-methylalanine (MeAla), N-methylvaline (MeVal), N-methylleucine (MeLeu), N-methylisoleucine (MeIle), N-methylmethionine (MeMet), N-methylproline (MePro), N-methylphenylalanine (MePhe), N-methyltryptophan (MeTyp), N-methyltyrosine (MeTyr), N-methylcysteine (MeCys), N-methylserine (MeSer), N-methylthreonine (MeThr), N-methylasparagine (MeAsn), N-methylglutamine (MeGln), N-methylaspartic acid (MeAsp), N-methylglutamic acid (MeGlu), N-methyllysine (MeLys), N-methylarginine (MeArg), N-methylhistidine (MeHis), N-ethylglycine (EtGly), N-propylglycine (PrGly), N-(4-aminobutyl)glycine, N-(4-aminopropyl)glycine, N-ethylasparagine (EtAsn), N-formylmethionine (FoMet) and N-mercaptoethylglycine (NHSEtGly).

(3) Amino Acids Having an Additional Substituent at the α-Carbon (α-Substituted Amino Acids)

Although the kinds of substituents are not particularly limited, an alkyl group can be exemplified. The alkyl group is preferably a linear or branched alkyl group having 1 to 6 carbon atoms, and examples of the linear C1-6 alkyl group include methyl group, ethyl group, n-propyl group, n-butyl group, n-pentyl group and n-hexyl group. Examples of the branched C1-6 alkyl group include isopropyl, isobutyl, sec-butyl, tert-butyl, isopentyl, neo-pentyl, 1-ethylpropyl, isohexyl, 1,1-dimethylbutyl, 2,2-dimethylbutyl, 3,3-dimethylbutyl, 2-ethylbutyl or the like. The alkyl group may be substituted by amino group, hydroxy group, thiol group or the like. A number of substituent(s) on the α-carbon is 1 or 2, preferably 1. Alkyl groups on a disubstituted α-carbon may be C—C bonded each other to construct a cycloalkyl group. Preferably, the cycloalkyl group has 4 to 6 carbon atoms. Examples of the C4-6 cycloalkyl group include cyclopropyl group, cyclopentyl group and cyclohexyl group.

Examples of the α-substituted amino acid include α-aminoisobutyric acid (methylalanine) (Aib), α-methylleucine (Aml), α-methylproline (Amp), α,α-diethylglycine (Deg), α,α-dibutylglycine (Dbg), 1-amino-cyclohexane-1-carboxylic acid (Ac6c), 1-amino-cyclopentane-1-carboxylic acid (Ac5c), 1-amino-cyclopropane-1-carboxylic acid (Ac3c), 1-amino-(4-N-piperidinyl)carboxylic acid (Apc) or the like.

(4) Amino Acids Having a Side Chain with an Alkylene Chain of Different Length

This type of amino acids has a structure in which C1-C2 alkylene chain has been eliminated from the side chain of a natural proteinogenic amino acid, or C1-C6 linear alkylene group has been inserted between the side chain and the α-carbon. Among them, examples of the amino acid having a structure in which C1 alkylene group (i.e., methylene group) has been inserted between the side chain and the α-carbon of a natural proteinogenic amino acid are indicated below along with the corresponding natural proteinogenic amino acids.

<alanine>homoalanine (2-aminobutyric acid) (hAla), 2-aminopentanoic acid (2Apn)
    <leucine>homoleucine (hLeu)
    <isoleucine>homoisoleucine (hIle)
    <methionine>homomethionine (hMet)
    <proline>pipecolic acid (Pip), azetidine-2-carboxylic acid (Az2Ca), azetidine-3-carboxylic acid (Az3Ca)
    <phenylalanine>homophenylalanine (hPhe), phenylglycine (fGly),
    <tryptophan>homotryptophane (hTrp)
    <tyrosine>homotyrosine (hTyr),
    <cysteine>homocysteine (hCys), norcysteine (Ncy)
    <serine>homoserine (hSer)
    <threonine>homothreonine (hThr),
    <glutamine>homoglutamine (hGln)
    <glutamic acid>homoglutamine acid (hGlu), 2-aminoadipic acid (Aad), 3-aminoadipic acid (βAad), 2-aminosuberic acid (Asu)(acid), 2-aminopimelic acid (Apm)
    <lysine>homolysine (hLys), ornithine (Orn), 2,4-diaminobutyric acid (2,4-A₂bu), 2,3-diaminobutyric acid (2,3-A₂bu), 2,3-diaminopropanoic acid (A2pr)
    <arginine>homoarginine (hArg), nor-arginine (nArg)
    <histidine>homohistidine (hHis)

(5) Amino acids having a substituted side chain

Examples of the amino acid having a substituted side chain are indicated below along with the corresponding natural proteinogenic amino acids.

<glycine>t-butylglycine (tbGly), 2-propargylglycine (pGly), cyclohexylglycine (chGly), cyclopentylglycine (cpGly), allylglycine (aGly)
    <alanine>t-butylalanine (tbAla), cyclohexylalanine (chAla), cyclobutylalanine (cbAla), cyclopropylalanine (cpAla), 1-naphthyl alanine (1npAla), 2-naphthyl alanine (2npAla), benzothienylalanine (btAla), thienylalanine (thAla), thiazolylalanine (taAla), furylalanine (fAla), pyridine-2-ylalanine (2pyAla), pyridine-3-ylalanine (3pAla), pyridine-4-ylalanine (4pyAla), 1-piperazinyl alanine (ppAla), styrylalanine (stAla), anthryl alanine (anAla)
    <methionine>selenomethionine (Sem), S-methylmethionine (mMet), methionine sulfoxide (Meo), methionine sulfone (Moo)
    <proline>3-hydroxyproline (3Hyp), 4-hydroxyproline (4Hyp), 5-hydroxyproline (5Hyp), 4-mercaptoproline (HSPro)
    <phenylalanine>2-methylphenylalanine (OmPhe), 3-methylphenylalanine (MmPhe), 4-methylphenylalanine (PmPhe), 2-nitrophenylalanine (OnPhe), 3-nitrophenylalanine (MnPhe), 4-nitrophenylalanine (PnPhe), 2-cyanophenylalanine (OcnPhe), 3-cyanophenylalanine (McnPhe), 4-cyanophenylalanine (PcnPhe), 3,3-diphenylalanine (ffAla), 2-trifluoromethylphenylalanine (OtPhe), 3-trifluoromethylphenylalanine (MtPhe), 4-trifluoromethylphenylalanine (PtPhe), 4-aminophenylalanine (PaPhe), 4-aminomethylphenylalanine (PamPhe), 3,4-dimethoxyphenylalanine (PmmDopa), 3,4-dihydroxyphenylalanine (Dopa), phosphonomethylphenylalanine (phmPhe), phenylalanine in which the aromatic ring has been substituted by a halogen (e.g., 2-chlorophenylalanine (OcPhe), 3-chlorophenylalanine (McPhe), 4-chlorophenylalanine (PcPhe), 2-fluorophenylalanine (OfPhe), 3-fluorophenylalanine (MfPhe), 4-fluorophenylalanine (PfPhe), 2-bromophenylalanine (ObPhe), 3-bromophenylalanine (MbPhe), 4-bromophenylalanine (PbPhe), 2-iodophenylalanine (OiPhe), 3-iodophenylalanine (MiPhe), 4-iodophenylalanine (PiPhe), 2,4-dichlorophenylalanine (OpcPhe), 3,4-dichlorophenylalanine (MpcPhe), 2,4-difluorophenylalanine (OpfPhe), 3,4-difluorophenylalanine (MpfPhe), 3,4,5-trifluorylphenylalanine (PmmfPhe), pentafluorophenylalanine (5fPhe))
    <tryptophan>5-fluorotryptophan (5fTyp), 6-fluorotryptophan (6fTyp), 1-methyltryptophan (1mTyp)
    <tyrosine>monoiodotyrosine (iTyr), diiodotyrosine (iiTyr), triiodothyronine (iiiThy), O-methyltyrosine (mTyr), 3-nitrotyrosine (nTyr), phosphotyrosine (pTyr), 3-amino-tyrosine (MaTyr)
    <cysteine>cysteineacid (Cya), S-benzyl-L-cysteine (bzCys), selenocysteine (Sec), penicillamine (Pen)
    <serine>O-methylserine (mSer), phosphoserine (pSer)
    <threonine>phosphothreonine (pThr),
    <glutamic acid>γ-hydroxyglutamic acid (hoGlu), γ-carboxyglutamic acid (caGlu)
    <lysine>Ne-acetyl lysine (AcLys), homocitrulline (Hci), 2,6-diaminopimelic acid (A2 pm), allohydroxylysine (AHyl), 2,6-diamino-4-hexyneacid (DaHea)
    <arginine>ω-nitroarginine (ntArg), ω-amino-arginine (Oar), ω-methyl-arginine (Omr), citrulline (Cit)
    <histidine>1-methylhistidine (lmHis), 3-methylhistidine (3mHis), 5-hydroxylysine (50HLys)

(6) Other Non-Proteinogenic Amino Acids

For example, 3-amino-5-phenylpentanoic acid (Afp), 1,2,3,4-tetrahydroisoquinoline-3-carboxylic acid (Tic), ω-hydroxy-nor-arginine (HOnArg), 1-aminocyclopentane-3-carboxylic acid (Acp3Ca), thiazolidine-4-carboxylic acid (thz) and 5,5-dimethyl-D-thiazolidine-4-carboxylic acid (dtc) can be mentioned but not limited to.

(7) Amino Acids Useful for Cyclization i) Amino Acids Having Chloroacetyl Group

Any amino acids in which amino group in the main chain or side chain is substituted with chloroacetyl group or 2-chloroacetamido benzoyl group (for example, the amino acids listed in Table 1)

Examples: N-chloroacetyl alanine, N-chloroacetylphenylalanine, N-chloroacetyl tyrosine, N-chloroacetyl tryptophan, N-3-(2-chloroacetamido)benzoylphenylalanine, N-3-(2-chloroacetamido)benzoyltyrosine, N-3-(2-chloroacetamido) benzoyltryptophan, β-N-chloroacetyl diaminopropanoic acid, γ-N-chloroacetyl diaminobutyric acid, σ-N-chloroacetyl ornithine, ε-N-chloroacetyl lysine ii) Amino Acids Having Ethynyl Group Propargylglycine, homopropargylglycine, 2-amino-6-heptynoic acid, 2-amino-7-octynic acid, 2-amino-8-nonynoic acid Any amino acids in which an amino group in the main chain or the side chain is substituted with 4-pentinoyl group, 5-hexynoyl group, 4-pentinoylamidobenzoyl group or 5-hexynoylamidobenzoyl group (e.g., amino acids listed in Table 1) Examples: N-(4-pentinoyl)alanine, N-(4-pentinoyl) phenylalanine, N-(4-pentinoyl)tyrosine, N-(4-pentinoyl) tryptophan, N-3-(4-pentinoylamido)benzoylphenylalanine, N-3-(4-pentinoylamido)benzoyltyrosine, N-3-(4-pentinoylamido)benzoyltryptophan, β-N-(4-pentinoyl)diaminopropanoic acid, γ-N-(4-pentinoyl)diaminobutyric acid, σ-N-(4-pentinoyl)ornithine, ε-N-(4-pentinoyl)lysine, N-(5-hexynoyl)alanine, N-(5-hexynoyl)phenylalanine, N-(5-hexynoyl)tyrosine, N-(5-hexynoyl)tryptophan, N-3-(5-hexynoylamido)benzoylphenylalanine, N-3-(5-hexynoylamido)benzoyltyrosine, N-3-(5-hexynoylamido) benzoyltryptophan, β-N-(5-hexynoyl)diaminopropanoic acid, γ-N-(5-hexynoyl)diaminobutyric acid, σ-N-(5-hexynoyl)ornithine, ε-N-(5-hexynoyl)lysine iii) Amino Acids Having Azido Group Azidealanine, 2-amino-4-azidebutanoic acid, 5-azidenorvaline, azidenorleucine, 2-amino-7-azideheptane acid and 2-amino-8-azideoctaneacid Any amino acids in which an amino group in the main chain or the side chain is substituted with azideacetyl group, 4-pentinoylamidobenzoyl group or 3-azidepentanoyl group (e.g., amino acids listed in Table 1) Examples: N-azideacetyl alanine, N-azideacetylphenylalanine, N-azideacetyl tyrosine, N-azideacetyl tryptophan, N-3-(4-pentinoylamido) benzoylphenylalanine, N-3-(4-pentinoylamido)benzoyltyrosine, N-3-(4-pentinoylamido)benzoyltryptophan, β-N-azideacetyl diaminopropanoic acid, γ-N-azideacetyl diaminobutyric acid, σ-N-azideacetyl ornithine, ε-N-azideacetyl lysine, N-3-azidepentanoylalanine, N-3-azidepentanoylphenylalanine, N-3-azidepentanoyltyrosine, N-3-azidepentanoyltryptophan, β-N-3-azidepentanoyldiaminopropanoic acid, γ-N-3-azidepentanoyldiaminobutyric acid, σ-N-3-azidepentanoylornithine, ε-N-3-azidepentanoyllysine iv) Amino Acids Having Benzylamino Group Amino acids amino having a side chain containing an aromatic ring, in which the aromatic ring in the side chain is substituted with aminomethyl group (Table 1) Examples: N-(4-aminomethylbenzoyl)phenylalanine (AMBF), 3-aminomethyltyrosine v) Amino Acids Having 5-Hydroxyindole Examples: 5-hydroxytryptophan vi) Amino acids having —C≡C—$CH_2$—X, —C=C—$CH_2$—X or —Ar—$CH_2$—X, wherein Ar is an aromatic ring which optionally has a substituent, X is a leaving group, and examples of the leaving group include a halogen atom including Cl, Br and I, or the like Examples: 2-amino-6-chlorohexyne acid, 2-amino-7-chloroheptynoic acid, 2-amino-8-chlorooctynic acid, N-3-chloromethylbenzoylphenylalanine, N-3-chloromethylbenzoyltyrosine, N-3-chloromethylbenzoyltryptophan Amino acids can be classified based on the property of their side chain. For example, amino acids can be classified into families including "hydrophobic amino acid" and "hydrophilic amino acid" based on the hydrophobicity of their side chain. Among hydrophobic amino acids, those having an alkyl group in their side chain refer to "aliphatic hydrophobic amino acids" and those having an aromatic ring in their side chain refer to "aromatic hydrophobic amino acids". Among aliphatic hydrophobic amino acids, those having a branched alkyl group in the side chain refer to branched aliphatic hydrophobic amino acids. Hydrophilic amino acids can be classified into families including "neutral hydrophilic amino acids" and "basic amino acids" based on the charge of their side chain.

In addition, amino acids can be classified based on the kind of a substituent or an atom contained in their side chain. For example, they can be classified into "amino acids having a side chain containing aromatic ring", "amino acids having a side chain containing amino group", "amino acids having a side chain containing carboxyl group", "amino acids having a side chain containing hydroxyl group", "amino acids having a side chain containing thiol group", "amino acids having a side chain containing amido group", "amino acids having a side chain containing imino group", "amino acids having a side chain containing a heterocycle", "amino acids having a side chain containing sulfur atom" and the like. One amino acid may belong to plural categories. Many of neutral hydrophilic amino acids may be classified as a family of "amino acids having a side chain containing hydroxyl, group", "amino acids having a side chain containing thiol group" or "amino acids having a side chain containing amido group". Many of basic amino acids may be classified as "amino acids having a side chain containing amino group". Many of acidic amino acids may be classified as "amino acids having a side chain containing carboxyl group".

Examples of the amino acid classification are shown in Table I. Codes of family of amino acids in Table 1 are as follows.

hydrophobic: hydrophobic amino acid
aliphatic: aliphatic hydrophobic amino acid
branched: branched aliphatic hydrophobic amino acid
aromatic: aromatic hydrophobic amino acid
hydrophilic: hydrophilic amino acid
basic: basic amino acid
acidic: acidic amino acid
neutral: neutral hydrophilic amino acid
aromatic ring: amino acid having a side chain containing aromatic ring
amino: amino acid having a side chain containing amino group
carboxy: amino acid having a side chain containing carboxy group
hydroxy: amino acid having a side chain containing hydroxyl group
thiol: amino acid having a side chain containing thiol group
amido: amino acid having a side chain containing amido group
imino: amino acid having a side chain containing imino group
heterocycle: amino acid having a side chain containing a heterocycle
sulfur: an amino acid having a side chain containing sulfur atom

TABLE 1

| Name | Abbreviation (one-letter) | Abbreviation (three or more letters) | Crassification according to hydrophobicity of side chain | | | | | | | |
|---|---|---|---|---|---|---|---|---|---|---|
| | | | hydrophobic | aliphatic | branched | aromatic | hydrophilic | basic | acidic | neutral |
| glycine | G | Gly | ○ | ○ | | | | | | |
| alanine | A | Ala | ○ | ○ | | | | | | |
| leucine | L | Leu | ○ | ○ | ○ | | | | | |
| isoleucine | I | Ile | ○ | ○ | ○ | | | | | |
| valine | V | Val | ○ | ○ | ○ | | | | | |
| methionine | M | Met | ○ | | | | | | | |
| proline | P | Pro | ○ | | | | | | | |
| phenylalanine | F | Phe | ○ | | | ○ | | | | |
| tryptophan | W | Typ | ○ | | | ○ | | | | |
| tyrosine | Y | Tyr | | | | | ○ | | | ○ |
| cysteine | C | Cys | | | | | ○ | | | ○ |
| serine | S | Ser | | | | | ○ | | | ○ |
| threonine | T | Thr | | | | | ○ | | | ○ |
| asparagine | N | Asn | | | | | ○ | | | ○ |
| glutamine | Q | Gln | | | | | ○ | | | ○ |
| aspartic acid | D | Asp | | | | | ○ | | ○ | |
| glutamic acid | E | Glu | | | | | ○ | | ○ | |
| lysine | K | Lys | | | | | ○ | ○ | | |
| arginine | R | Arg | | | | | ○ | ○ | | |
| histidine | H | His | | | | | ○ | ○ | | |
| D-alanine | s | ala | ○ | ○ | | | | | | |
| D-leucine | l | leu | ○ | ○ | ○ | | | | | |
| D-isoleucine | i | ile | ○ | ○ | ○ | | | | | |
| D-valine | v | val | ○ | ○ | ○ | | | | | |
| D-methionine | m | met | ○ | | | | | | | |
| D-proline | p | pro | ○ | | | | | | | |
| D-phenylalanine | f | phe | ○ | | | ○ | | | | |
| D-tryptophan | w | typ | ○ | | | ○ | | | | |
| D-tyrosine | y | tyr | | | | | ○ | | | ○ |
| D-cysteine | c | cys | | | | | ○ | | | ○ |
| D-serine | s | ser | | | | | ○ | | | ○ |
| D-threonine | t | thr | | | | | ○ | | | ○ |
| D-asparagine | n | asn | | | | | ○ | | | ○ |
| D-glutamine | q | gln | | | | | ○ | | | ○ |
| D-aspartic acid | d | asp | | | | | ○ | | ○ | |
| D-glutamic acid | e | glu | | | | | ○ | | ○ | |
| D-lysine | k | lys | | | | | ○ | ○ | | |
| D-arginine | r | arg | | | | | ○ | ○ | | |
| D-histidine | h | his | | | | | ○ | ○ | | |
| alloisoleucine | | AIle | ○ | ○ | ○ | | | | | |
| allothreonine | | alThr | | | | | ○ | | | ○ |
| β-alanine | | bAla | ○ | ○ | | | | | | |
| β-leucine | | bLeu | ○ | ○ | ○ | | | | | |
| β-methionine | | bMet | ○ | | | | | | | |
| β-phenylalanine | | bPhe | ○ | | | ○ | | | | |
| β-tyrosine | | bTyr | | | | | ○ | | | ○ |
| β-cysteine | | bCys | | | | | ○ | | | ○ |
| β-serine | | bSer | | | | | ○ | | | ○ |
| β-threonine | | bThr | | | | | ○ | | | ○ |
| β-asparagine | | bAsn | | | | | ○ | | | ○ |
| β-glutamine | | bGln | | | | | ○ | | | ○ |
| β-aspartic acid | | bAsp | | | | | ○ | | ○ | |
| β-glutamic acid | | bGlu | | | | | ○ | | ○ | |
| β-lysine | | bLys | | | | | ○ | ○ | | |
| β-arginine | | bArg | | | | | ○ | ○ | | |
| β-histidine | | bHis | | | | | ○ | ○ | | |
| isoaspartic acid | | iAsp | | | | | ○ | | ○ | |
| isoglutamic acid | | iGlu | | | | | ○ | | ○ | |
| norleucine | | Nle | ○ | ○ | | | | | | |
| tert-leucine | | Tle | ○ | ○ | ○ | | | | | |
| norvaline | | Nva | ○ | ○ | | | | | | |
| β-homoalanine | | Bha | ○ | ○ | | | | | | |
| β-homovaline | | Bhv | ○ | ○ | ○ | | | | | |
| β-homoleucine | | Bhi | ○ | ○ | ○ | | | | | |
| β-homoisoleucine | | Bhi | ○ | ○ | ○ | | | | | |
| β-homomethionine | | Bhm | ○ | | | | | | | |
| β-homophenylalanine | | Bhf | ○ | | | ○ | | | | |
| β-homotryptophane | | Bhw | ○ | | | ○ | | | | |
| β-homotyrosine | | Bhy | | | | | ○ | | | ○ |
| β-homocysteine | | Bhc | | | | | ○ | | | ○ |
| β-homoserine | | Bhs | | | | | ○ | | | ○ |
| β-homothreonine | | Bht | | | | | ○ | | | ○ |
| β-homoasparagine | | Bhn | | | | | ○ | | | ○ |
| β-homoglutamine | | Bhq | | | | | ○ | | | ○ |
| β-homoaspartic acid | | Bhe | | | | | ○ | | ○ | |

TABLE 1-continued

| | | | | | | | | | |
|---|---|---|---|---|---|---|---|---|---|
| β-homoglutamine acid | Bhd | | | | | ○ | | ○ | |
| β-homolysine | Bhk | | | | | ○ | ○ | | |
| β-homoarginine | Bhr | | | | | ○ | ○ | | |
| β-homohistidine | Bhh | | | | | ○ | ○ | | |
| 3-aminobutyric acid | 3Abu | ○ | ○ | | | | | | |
| 4-aminobutyric acid | 4Abu | ○ | ○ | | | | | | |
| 6-aminohexanoic acid | ε Ahx | ○ | ○ | | | | | | |
| 5-aminopentanoic acid | δ Ava | ○ | ○ | | | | | | |
| N-methylglycine (sarcosine) | MeGly | ○ | ○ | | | | | | |
| N-methylalanine | MeAla | ○ | ○ | | | | | | |
| N-methylleucine | MeLeu | ○ | ○ | ○ | | | | | |
| N-methylisoleucine | MeIle | ○ | ○ | ○ | | | | | |
| N-methylvaline | MeVal | ○ | ○ | ○ | | | | | |
| N-methylmethionine | MeMet | ○ | | | | | | | |
| N-methylproline | MePro | ○ | | | | | | | |
| N-methylphenylalanine | MePhe | ○ | | | ○ | | | | |
| N-methyltryptophan | MeTyp | ○ | | | ○ | | | | |
| N-methyltyrosine | MeTyr | | | | | ○ | | | ○ |
| N-methylcysteine | MeCys | | | | | ○ | | | ○ |
| N-methylserine | MeSer | | | | | ○ | | | ○ |
| N-methylthreonine | MeThr | | | | | ○ | | | ○ |
| N-methylasparagine | MeAsn | | | | | ○ | | | ○ |
| N-methylglutamine | MeGln | | | | | ○ | | | ○ |
| N-methylaspartic acid | MeAsp | | | | | ○ | | ○ | |
| N-methylglutamic acid | MeGlu | | | | | ○ | | ○ | |
| N-methyllysine | MeLys | | | | | ○ | ○ | | |
| N-methylarginine | MeArg | | | | | ○ | ○ | | |
| N-methylhistidine | MeHis | | | | | ○ | ○ | | |
| N-ethylglycine | EtGly | ○ | ○ | | | | | | |
| N-propylglycine | PrGly | ○ | ○ | | | | | | |
| N-(4-aminobutyl)glycine | AbGly | ○ | ○ | | | | | | |
| N-(4-aminopropyl)glycine | ApGly | ○ | ○ | | | | | | |
| N-ethylasparagine | EtAsn | | | | | ○ | | | ○ |
| N-formylmethionine | FoMet | ○ | | | | | | | |
| N-mercaptoethylglycine | NHSEtGly | ○ | | | | | | | |
| α-aminoisobutyric acid (α-methylalanine) | Aib | | ○ | | | | | | |
| α-methylleucine | Aml | ○ | ○ | ○ | | | | | |
| α-methylproline | Amp | ○ | | | | | | | |
| α,α-diethylglycine | Deg | ○ | ○ | | | | | | |
| α,α-dibutylglycine | Dbg | ○ | ○ | | | | | | |
| 1-amino-cyclohexane-1-carboxylic acid | Ac6c | ○ | ○ | | | | | | |
| 1-amino-cyclopentane-1-carboxylic acid | Ac5c | ○ | ○ | | | | | | |
| 1-amino-cyclopropane-1-carboxylic acid | Ac3c | ○ | ○ | | | | | | |
| 1-amino-(4-N-piperidinyl) carboxylic acid | Apc | ○ | ○ | | | | | | |
| homoalanine | hAla | ○ | ○ | | | | | | |
| 2-aminopentanoic acid | 2Apn | ○ | ○ | | | | | | |
| homoleucine | hLeu | ○ | ○ | ○ | | | | | |
| homoisoleucine | hIle | ○ | ○ | ○ | | | | | |
| homomethionine | hMet | ○ | | | | | | | |
| pipecolic acid | Pip | ○ | | | | | | | |
| azetidine-3-carboxylic acid | Az3Ca | ○ | | | | | | | |
| azetidine-2-carboxylic lacid | Az2Ca | ○ | | | | | | | |
| homophenylalanine | hPhe | ○ | | | ○ | | | | |
| phenylglycine | fGly | ○ | | | ○ | | | | |
| homotryptophane | hTyp | ○ | | | ○ | | | | |
| homotyrosine | hTyr | | | | | ○ | | | ○ |
| homocysteine | hCys | | | | | ○ | | | ○ |
| horcysteine | Ncy | | | | | ○ | | | ○ |
| homoserine | hSer | | | | | ○ | | | ○ |
| homothreonine | hThr | | | | | ○ | | | ○ |
| homoglutamine | hGln | | | | | ○ | | | ○ |
| homoglutamine acid | hGlu | | | | | ○ | | ○ | |
| 2-aminoadipic acid | Aad | | | | | ○ | | ○ | |
| 3-aminoadipic acid | β Aad | | | | | ○ | | ○ | |
| 2-aminosuberic acid | Asu | | | | | ○ | | ○ | |
| 2-aminopimeric acid | Apm | | | | | ○ | | ○ | |
| homolysine | hLys | | | | | ○ | ○ | | |

TABLE 1-continued

| | | | | | | | | | |
|---|---|---|---|---|---|---|---|---|---|
| ornithine | Orn | | | | | ○ | ○ | | |
| 2,4-diaminobutyric acid | 2,4-A2bu | | | | | ○ | ○ | | |
| 2,3-diaminobutyric acid | 2,3-A2bu | | | | | ○ | ○ | | |
| 2,3-diaminopropanoic acid | A2pr | | | | | ○ | ○ | | |
| homoarginine | hArg | | | | | ○ | ○ | | |
| nor-arginine | nArg | | | | | ○ | ○ | | |
| homohistidine | hHis | | | | | ○ | ○ | | |
| t-butylglycine | tbGly | ○ | ○ | ○ | | | | | |
| 2-propargylglycine | pGly | ○ | ○ | | | | | | |
| cyclohexylglycine | chGly | ○ | ○ | ○ | | | | | |
| cyclopentylglycine | aGly | ○ | ○ | | | | | | |
| t-butylalanine | tbAla | ○ | ○ | ○ | | | | | |
| cyclohexylalanine | chAla | ○ | ○ | ○ | | | | | |
| cyclobutylalanine | cbAla | ○ | ○ | ○ | | | | | |
| cyclopropylalanine | cpAla | ○ | ○ | ○ | | | | | |
| 1-naphthyl alanine | 1npAla | ○ | | | ○ | | | | |
| 2-naphthyl alanine | 2npAla | ○ | | | ○ | | | | |
| benzothienylalanine | btAla | ○ | | | ○ | | | | |
| thienylalanine | thAla | ○ | | | ○ | | | | |
| thiazolylalanine | taAla | ○ | | | ○ | | | | |
| furylalanine | FAla | ○ | | | ○ | | | | |
| pyridine-2-ylalanine | 2pyAla | | | | | ○ | ○ | | |
| pyridine-3-ylalanine | 3pyAla | | | | | ○ | ○ | | |
| pyridine-4-ylalanine | 4pyAla | | | | | ○ | ○ | | |
| 1-piperazinyl alanine | ppAla | | | | | ○ | ○ | | |
| styrylalanine | stAla | ○ | | | ○ | | | | |
| anthryl alanine | anAla | ○ | | | ○ | | | | |
| selenomethionine | Sem | ○ | | | | | | | |
| S-methylmethionine | mMet | ○ | | | | | | | |
| methionine sulfoxide | Meo | | | | | ○ | | | ○ |
| methionine sulfone | Moo | | | | | ○ | | ○ | |
| 3-hydroxyproline | 3Hyp | | | | | ○ | | | ○ |
| 4-hydroxyproline | 4Hyp | | | | | ○ | | | ○ |
| 5-hydroxyproline | 5Hyp | | | | | ○ | | | ○ |
| 4-mercaptoproline | HSPro | | | | | ○ | | | ○ |
| 2-methylphenylalanine | OmPhe | ○ | | | ○ | | | | |
| 3-methylphenylalanine | MmPhe | ○ | | | ○ | | | | |
| 4-methylphenylalanine | PmPhe | ○ | | | ○ | | | | |
| 2-nitrophenylalanine | OnPhe | ○ | | | ○ | | | | |
| 3-nitrophenylalanine | MnPhe | ○ | | | ○ | | | | |
| 4-nitrophenylalanine | PnPhe | ○ | | | ○ | | | | |
| 2-cyanophenylalanine | OcnPha | | | | | ○ | | | ○ |
| 3-cyanophenylalanine | McnPhe | | | | | ○ | | | ○ |
| 4-cyanophenylalanine | PcnPhe | | | | | ○ | | | ○ |
| 3,3-diphenylalanine | ffAla | ○ | | | ○ | | | | |
| 2-trifluoromethylphenylalanine | OtPhe | ○ | | | ○ | | | | |
| 3-trifluoromethylphenylalanine | MtPhe | ○ | | | ○ | | | | |
| 4-trifluoromethylphenylalanine | PtPhe | ○ | | | ○ | | | | |
| 4-aminophenylalanine | PaPhe | | | | | ○ | ○ | | |
| 4-aminomethylphenylalanine | PamPhe | | | | | ○ | ○ | | |
| 3,4-dimethoxyphenylalanine | PmmDopa | ○ | | | ○ | | | | |
| 3,4-dihydroxyphenylalanine | Dopa | | | | | ○ | | | ○ |
| phosphonomethylphenylalanine | phmPhe | | | | | ○ | | ○ | |
| 2-chlorophenylalanine | OcPhe | ○ | | | ○ | | | | |
| 3-chlorophenylalanine | McPhe | ○ | | | ○ | | | | |
| 4-chlorophenylalanine | PcPhe | ○ | | | ○ | | | | |
| 2-bromophenylalanine | ObPhe | ○ | | | ○ | | | | |
| 3-bromophenylalanine | MbPhe | ○ | | | ○ | | | | |
| 4-bromophenylalanine | PbPhe | ○ | | | ○ | | | | |
| 2-iodophenylalanine | OiPhe | ○ | | | ○ | | | | |
| 3-iodophenylalanine | MiPhe | ○ | | | ○ | | | | |
| 4-iodophenylalanine | PiPhe | ○ | | | ○ | | | | |
| 2,4-dichlorophenylalanine | OpcPhe | ○ | | | ○ | | | | |
| 3,4-dichlorophenylalanine | MpcPhe | ○ | | | ○ | | | | |
| 2,4-difluorophenylalanine | OpfPhe | ○ | | | ○ | | | | |
| 3.4-difluorophenylalanine | MpfPhe | ○ | | | ○ | | | | |

TABLE 1-continued

| | | | | | | | |
|---|---|---|---|---|---|---|---|
| 3,4,5-trifluorophenylalanine | PmmfPhe | ○ | ○ | | | | |
| pentafluorophenylalanine | 5fPhe | ○ | ○ | | | | |
| 5-fluorotryptophan | 5fTyp | ○ | ○ | | | | |
| 6-fluorotryptophan | 6fTyp | ○ | ○ | | | | |
| 1-methyltryptophan | 1mTyp | ○ | ○ | | | | |
| monoiodotyrosine | iTyr | | | ○ | | | ○ |
| dilodotyrosine | iiTyr | | | ○ | | | ○ |
| triiodothyronine | iiiThy | | | ○ | | | ○ |
| O-methyltyrosine | mTyr | ○ | ○ | | | | |
| 3-nitrotyrosine | nTyr | | | ○ | | | ○ |
| phosphotyrosine | pTyr | | | ○ | | ○ | |
| 3-amino-tyrosine | MaTyr | | | ○ | ○ | | |
| cysteineacid | Cya | | | ○ | | ○ | |
| S-benzyl-L-cysteine | bzCys | ○ | ○ | | | | |
| selenocysteine | Sec | | | ○ | | | ○ |
| penicillamine | Pen | | | ○ | | | ○ |
| 5-mercaptonorvaline | shNva | | | ○ | | | ○ |
| 6-mercaptonorleucine | shNle | | | ○ | | | ○ |
| 2-amino-7-mercaptoheptane acid | shHep | | | ○ | | | ○ |
| 2-amino-8-mercaptooctaneacid | shOct | | | ○ | | | ○ |
| O-methylserine | mSer | ○ | | | | | |
| phosphoserine | pSer | | | ○ | | ○ | |
| phosphothreonine | pThr | | | ○ | | ○ | |
| γ-hydroxyglutamic acid | hoGlu | | | ○ | | ○ | |
| γ-carboxyglutamio acid | caGlu | | | ○ | | ○ | |
| N ε-acetyl lysine | AcLys | | | ○ | | | ○ |
| homocitrulline | Hci | | | ○ | | | ○ |
| 2,6-diaminopimelic acid | A2pm | | | ○ | | | ○ |
| alohydroxyllysine | Ahyl | | | ○ | ○ | | |
| 2,6-diamino-4-hexyneacid | DaHea | | | ○ | ○ | | |
| ω-nitroarginine | ntArg | | | ○ | ○ | | |
| ω-amino-arginine | Oar | | | ○ | ○ | | |
| ω-methyl-arginine | Omr | | | ○ | ○ | | |
| citrulline | Cit | | | ○ | | | ○ |
| 1-methylhistidine | 1mHis | | | ○ | ○ | | |
| 3-methylhistidine | 3mHis | | | ○ | ○ | | |
| 5-methylhistidine | 5mHis | | | ○ | ○ | | |
| 3-amino-5-phenylpentanoic acid | Afp | ○ | ○ | | | | |
| 1,2,3,4-tetrahydroisoquinoline-3-carboxylic acid | Tic | ○ | ○ | | | | |
| ω-hydroxy-nor-arginine | HOnArg | | | ○ | ○ | | |
| 1-aminocyclopentane-3-carboxylic acid | Acp3Ca | ○ | | | | | |
| thiazolidine-4-carboxylic acid | thz | ○ | | | | | |
| 5,5-dimethyl-D-thiazolidine-4-carboxylic acid | dtc | ○ | | | | | |

| | Crassification according to kind of substituent or the like contained in side chain | | | | | | | | |
|---|---|---|---|---|---|---|---|---|---|
| Name | aromatic ring | amino | carboxy | hydroxy | thiol | amido | imina | heterocycle | sulfur |
| glycine | | | | | | | | | |
| alanine | | | | | | | | | |
| leucine | | | | | | | | | |
| isoleucine | | | | | | | | | |
| valine | | | | | | | | | |
| methionine | | | | | | | | | ○ |
| proline | | | | | | | ○ | ○ | |
| phenylalanine | ○ | | | | | | | | |
| tryptophan | ○ | | | | | | | ○ | |
| tyrosine | ○ | | | ○ | | | | | |
| cysteine | | | | | ○ | | | | ○ |
| serine | | | | ○ | | | | | |
| threonine | | | | ○ | | | | | |
| asparagine | | | | | | ○ | | | |
| glutamine | | | | | | ○ | | | |
| aspartic acid | | | ○ | | | | | | |
| glutamic acid | | | ○ | | | | | | |

TABLE 1-continued

| | | | | | | | | | |
|---|---|---|---|---|---|---|---|---|---|
| lysine | | ○ | | | | | | | |
| arginine | | ○ | | | | | | | |
| histidine | | ○ | | | | | | ○ | |
| D-alanine | | | | | | | | | |
| D-leucine | | | | | | | | | |
| D-isoleucine | | | | | | | | | |
| D-valine | | | | | | | | | |
| D-methionine | | | | | | | | | ○ |
| D-proline | | | | | | | ○ | ○ | |
| D-phenylalanine | ○ | | | | | | | | |
| D-tryptophan | ○ | | | | | | | ○ | |
| D-tyrosine | ○ | | | ○ | | | | | |
| D-cysteine | | | | | ○ | | | | ○ |
| D-serine | | | | ○ | | | | | |
| D-threonine | | | | ○ | | | | | |
| D-asparagine | | | | | | ○ | | | |
| D-glutamine | | | | | | ○ | | | |
| D-aspartic acid | | | ○ | | | | | | |
| D-glutamic acid | | | ○ | | | | | | |
| D-lysine | | ○ | | | | | | | |
| D-arginine | | ○ | | | | | | | |
| D-histidine | | ○ | | | | | | ○ | |
| alloisoleucine | | | | | | | | | |
| allothreonine | | | | ○ | | | | | |
| β-alanine | | | | | | | | | |
| β-leucine | | | | | | | | | |
| β-methionine | | | | | | | | | ○ |
| β-phenylalanine | ○ | | | | | | | | |
| β-tyrosine | ○ | | | | | | | | |
| β-cysteine | | | | | ○ | | ○ | | ○ |
| β-serine | | | | ○ | | | | | |
| β-threonine | | | | ○ | | | | | |
| β-asparagine | | | | | | ○ | | | |
| β-glutamine | | | | | | ○ | | | |
| β-aspartic acid | | | ○ | | | | | | |
| β-glutamic acid | | | ○ | | | | | | |
| β-lysine | | ○ | | | | | | | |
| β-arginine | | ○ | | | | | | | |
| β-histidine | | ○ | | | | | | ○ | |
| isoaspartic acid | | | ○ | | | | | | |
| isoglutamic acid | | | ○ | | | | | | |
| norleucine | | | | | | | | | |
| tert-leucine | | | | | | | | | |
| norvaline | | | | | | | | | |
| β-homoalanine | | | | | | | | | |
| β-homovaline | | | | | | | | | |
| β-homoleucine | | | | | | | | | |
| β-homoisoleucine | | | | | | | | | |
| β-homomethionine | | | | | | | | | ○ |
| β-homophenylalanine | ○ | | | | | | | | |
| β-homotryptophane | ○ | | | | | | | ○ | |
| β-homotyrosine | ○ | | | | | | | | |
| β-homocysteine | | | | | ○ | | ○ | | ○ |
| β-homoserine | | | | ○ | | | | | |
| β-homothreonine | | | | ○ | | | | | |
| β-homoasparagine | | | | | | ○ | | | |
| β-homoglutamine | | | | | | ○ | | | |
| β-homoaspartic acid | | | ○ | | | | | | |
| β-homoglutamine acid | | | ○ | | | | | | |
| β-homolysine | | ○ | | | | | | | |
| β-homoarginine | | ○ | | | | | | | |
| β-homohistidine | | ○ | | | | | | ○ | |
| 3-aminobutyric acid | | | | | | | | | |
| 4-aminobutyric acid | | | | | | | | | |
| 6-aminohexanoic acid | | | | | | | | | |
| 5-aminopentanoic acid | | | | | | | | | |
| N-methylglycine (sarcosine) | | | | | | | | | |
| N-methylalanine | | | | | | | | | |
| N-methylleucine | | | | | | | | | |
| N-methylisoleucine | | | | | | | | | |
| N-methylvaline | | | | | | | | | |
| N-methylmethionine | | | | | | | | | ○ |
| N-methylproline | | | | | | | ○ | ○ | |
| N-methylphenylalanine | ○ | | | | | | | | |
| N-methyltryptophan | ○ | | | | | | | ○ | |
| N-methyltyrosine | ○ | | | | | | | | |
| N-methylcysteine | | | | | ○ | | ○ | | ○ |
| N-methylserine | | | | ○ | | | | | |
| N-methylthreonine | | | | ○ | | | | | |

TABLE 1-continued

| | | | | | | | | | |
|---|---|---|---|---|---|---|---|---|---|
| N-methylasparagine | | | | | | ○ | | | |
| N-methylglutamine | | | | | | ○ | | | |
| N-methylaspartic acid | | | ○ | | | | | | |
| N-methylglutamic acid | | | ○ | | | | | | |
| N-methyllysine | | ○ | | | | | | | |
| N-methylarginine | | ○ | | | | | | | |
| N-methylhistidine | | ○ | | | | | | ○ | |
| N-ethylglycine | | | | | | | | | |
| N-propylglycine | | | | | | | | | |
| N-(4-aminobutyl)glycine | | | | | | | | | |
| N-(4-aminopropyl)glycine | | | | | | | | | |
| N-ethylasparagine | | | | | | ○ | | | |
| N-formylmethionine | | | | | | | | | ○ |
| N-mercaptoethylglycine | | | | | ○ | | | | |
| α-aminoisobutyric acid (α-methylalanine) | | | | | | | | | |
| α-methylleucine | | | | | | | | | |
| α-methylproline | | | | | | | ○ | ○ | |
| α,α-diethylglycine | | | | | | | | | |
| α,α-dibutylglycine | | | | | | | | | |
| 1-amino-cyclohexane-1-carboxylic acid | | | | | | | | | |
| 1-amino-cyclopentane-1-carboxylic acid | | | | | | | | | |
| 1-amino-cyclopropane-1-carboxylic acid | | | | | | | | | |
| 1-amino-(4-N-piperidinyl) carboxylic acid | | ○ | | | | | | ○ | |
| homoalanine | | | | | | | | | |
| 2-aminopentanoic acid | | | | | | | | | |
| homoleucine | | | | | | | | | |
| homoisoleucine | | | | | | | | | |
| homomethionine | | | | | | | | | ○ |
| pipecolic acid | | | | | | | ○ | ○ | |
| azetidine-3-carboxylic acid | | | | | | | ○ | ○ | |
| azetidine-2-carboxylic lacid | | | | | | | ○ | ○ | |
| homophenylalanine | ○ | | | | | | | | |
| phenylglycine | ○ | | | | | | | | |
| homotryptophane | ○ | | | | | | | ○ | |
| homotyrosine | ○ | | | | | | | | |
| homocysteine | | | | | ○ | | ○ | | ○ |
| horcysteine | | | | | ○ | | | | |
| homoserine | | | | ○ | | | | | |
| homothreonine | | | | ○ | | | | | |
| homoglutamine | | | | | | ○ | | | |
| homoglutamine acid | | | ○ | | | | | | |
| 2-aminoadipic acid | | | ○ | | | | | | |
| 3-aminoadipic acid | | | ○ | | | | | | |
| 2-aminosuberic acid | | | ○ | | | | | | |
| 2-aminopimeric acid | | | ○ | | | | | | |
| homolysine | | ○ | | | | | | | |
| ornithine | | ○ | | | | | | | |
| 2,4-diaminobutyric acid | | ○ | | | | | | | |
| 2,3-diaminobutyric acid | | ○ | | | | | | | |
| 2,3-diaminopropanoic acid | | ○ | | | | | | | |
| homoarginine | | ○ | | | | | | | |
| nor-arginine | | ○ | | | | | | | |
| homohistidine | | ○ | | | | | | ○ | |
| t-butylglycine | | | | | | | | | |
| 2-propargylglycine | | | | | | | | | |
| cyclohexylglycine | | | | | | | | | |
| cyclopentylglycine | | | | | | | | | |
| t-butylalanine | | | | | | | | | |
| cyclohexylalanine | | | | | | | | | |
| cyclobutylalanine | | | | | | | | | |
| cyclopropylalanine | | | | | | | | | |
| 1-naphthyl alanine | ○ | | | | | | | | |
| 2-naphthyl alanine | ○ | | | | | | | | |
| benzothienylalanine | ○ | | | | | | | ○ | ○ |
| thienylalanine | ○ | | | | | | | ○ | ○ |

TABLE 1-continued

| | | | | | | | |
|---|---|---|---|---|---|---|---|
| thiazolylalanine | ○ | | | | | ○ | ○ |
| furylalanine | ○ | | | | | ○ | |
| pyridine-2-ylalanine | ○ | | | | | ○ | |
| pyridine-3-ylalanine | ○ | | | | | ○ | |
| pyridine-4-ylalanine | ○ | | | | | ○ | |
| 1-piperazinyl alanine | | ○ | | | | ○ | |
| styrylalanine | ○ | | | | | | |
| anthryl alanine | ○ | | | | | | |
| selenomethionine | | | | | | | |
| S-methylmethionine | | | | | | | ○ |
| methionine sulfoxide | | | | | | | ○ |
| methionine sulfone | | | | | | | ○ |
| 3-hydroxyproline | | | ○ | | ○ | ○ | |
| 4-hydroxyproline | | | ○ | | ○ | ○ | |
| 5-hydroxyproline | | | ○ | | ○ | ○ | |
| 4-mercaptoproline | | | | ○ | ○ | ○ | |
| 2-methylphenylalanine | ○ | | | | | | |
| 3-methylphenylalanine | ○ | | | | | | |
| 4-methylphenylalanine | ○ | | | | | | |
| 2-nitrophenylalanine | ○ | | | | | | |
| 3-nitrophenylalanine | ○ | | | | | | |
| 4-nitrophenylalanine | ○ | | | | | | |
| 2-cyanophenylalanine | ○ | | | | | | |
| 3-cyanophenylalanine | ○ | | | | | | |
| 4-cyanophenylalanine | ○ | | | | | | |
| 3,3-diphenylalanine | ○ | | | | | | |
| 2-trifluoromethylphenylalanine | ○ | | | | | | |
| 3-trifluoromethylphenylalanine | ○ | | | | | | |
| 4-trifluoromethylphenylalanine | ○ | | | | | | |
| 4-aminophenylalanine | ○ | ○ | | | | | |
| 4-aminomethylphenylalanine | ○ | ○ | | | | | |
| 3,4-dimethoxyphenylalanine | ○ | | | | | | |
| 3,4-dihydroxyphenylalanine | ○ | | ○ | | | | |
| phosphonomethylphenylalanine | ○ | | | | | | |
| 2-chlorophenylalanine | ○ | | | | | | |
| 3-chlorophenylalanine | ○ | | | | | | |
| 4-chlorophenylalanine | ○ | | | | | | |
| 2-bromophenylalanine | ○ | | | | | | |
| 3-bromophenylalanine | ○ | | | | | | |
| 4-bromophenylalanine | ○ | | | | | | |
| 2-iodophenylalanine | ○ | | | | | | |
| 3-iodophenylalanine | ○ | | | | | | |
| 4-iodophenylalanine | ○ | | | | | | |
| 2,4-dichlorophenylalanine | ○ | | | | | | |
| 3,4-dichlorophenylalanine | ○ | | | | | | |
| 2,4-difluorophenylalanine | ○ | | | | | | |
| 3.4-difluorophenylalanine | ○ | | | | | | |
| 3,4,5-trifluorophenylalanine | ○ | | | | | | |
| pentafluorophenylalanine | ○ | | | | | | |
| 5-fluorotryptophan | ○ | | | | | ○ | |
| 6-fluorotryptophan | ○ | | | | | ○ | |
| 1-methyltryptophan | ○ | | | | | ○ | |
| monoiodotyrosine | ○ | | ○ | | | | |
| dilodotyrosine | ○ | | ○ | | | | |
| triiodothyronine | ○ | | ○ | | | | |
| O-methyltyrosine | ○ | | | | | | |
| 3-nitrotyrosine | ○ | | ○ | | | | |
| phosphotyrosine | ○ | | | | | | |
| 3-amino-tyrosine | ○ | ○ | ○ | | | | |
| cysteineacid | | | | | | | ○ |
| S-benzyl-L-cysteine | ○ | | | | | | ○ |
| selenocysteine | | | | | | | |
| penicillamine | | | | ○ | | | |
| 5-mercaptonorvaline | | | | ○ | | | |
| 6-mercaptonorleucine | | | | ○ | | | |
| 2-amino-7-mercaptoheptane acid | | | | ○ | | | |

TABLE 1-continued

| | | | | | | | | | |
|---|---|---|---|---|---|---|---|---|---|
| 2-amino-8-mercaptooctaneacid | | | | | ○ | | | | |
| O-methylserine | | | | | | | | | |
| phosphoserine | | | | | | | | | |
| phosphothreonine | | | | | | | | | |
| γ-hydroxyglutamic acid | | | ○ | ○ | | | | | |
| γ-carboxyglutamio acid | | | ○ | | | | | | |
| N ε-acetyl lysine | | | | | | ○ | | | |
| homocitrulline | | ○ | | | | ○ | | | |
| 2,6-diaminopimelic acid | | ○ | ○ | | | | | | |
| alohydroxyllysine | | ○ | | ○ | | | | | |
| 2,6-diamino-4-hexyneacid | | ○ | | | | | | | |
| ω-nitroarginine | | ○ | | | | | | | |
| ω-amino-arginine | | ○ | | | | | | | |
| ω-methyl-arginine | | ○ | | | | | | | |
| citrulline | | ○ | | | | ○ | | | |
| 1-methylhistidine | | ○ | | | | | | ○ | |
| 3-methylhistidine | | ○ | | | | | | ○ | |
| 5-methylhistidine | | ○ | | | | | | ○ | |
| 3-amino-5-phenylpentanoic acid | ○ | | | | | | | | |
| 1,2,3,4-tetrahydroisoquinoline-3-carboxylic acid | ○ | | | | | | ○ | | |
| ω-hydroxy-nor-arginine | | ○ | | ○ | | | | | |
| 1-aminocyclopentane-3-carboxylic acid | | | | | | | ○ | ○ | |
| thiazolidine-4-carboxylic acid | | | | | | | ○ | ○ | ○ |
| 5,5-dimethyl-D-thiazolidine-4-carboxylic acid | | | | | | | ○ | ○ | ○ |

As used herein, the term "conservative substitution" means that one amino acid constituting a peptide is replaced with another amino acid in the amino acid family with which it shares the same side chain chemical property. For example, one amino acid is replaced with another amino acid in one of the amino acid families listed in Table 1 to which said amino acid belongs. Examples of conservative substitutions are shown in Table 2.

TABLE 2

| Original amino acid | Examples of preservative substitution |
|---|---|
| Gly (G) | Ala, ala, MeGly, MeAla, EtGly, Aib, hAla, 2Abu, pGly, Sem, Nle, Nva, 2Apn, Aad, 4Abu, ε Ahx, Ava, hAla, 2Apn |
| Ala (A) | Gly, Met, ala, met, Aib, Deg, MeGly, MeAla, EtGly, hAla, 2Abu, pGly, Sem, Nle, Nva, 2Apn, Aad |
| Leu (L) | Ile, Val, Met, ile, leu, val, Aml, Deg, Dbg, MeLeu, MeIle, MeVal, Bhl, Bhv, hAla, hIle, 2Abu, tbGly, tbAla, Nle, Tle, Nva, 2Apn, AIle, pGly, aGly, chGly, cpGly, chAla, cbAla, cpAla |
| Ile (I) | Leu, Val, Met, ile, leu, val, Aml, Deg, Dbg, MeLeu, MeIle, MeVal, Bhl, Bhv, hAla, hIle, 2Abu, tbGly, tbAla, Nle, Tle, Nva, 2Apn, AIle, pGly, aGly, chGly, cpGly, chAla, cbAla, cpAla |
| Val (V) | Ile, Leu, Met, ile, leu, val, Aml, Deg, Dbg, MeLeu, MeIle, MeVal, Bhl, Bhv, hAla, hIle, 2Abu, tbGly, tbAla, Nle, Tle, Nva, 2Apn, AIle, pGly, aGly, chGly, cpGly, chAla, cbAla, cpAla |
| Met (M) | Ile, Leu, Val, ile, leu, met, val, MeMet, FoMet, Sem, mMet, Nle, Nva, 2Apn, Aad, Meo, Moo |
| Pro (P) | pro, Amp, Tic, 3Hyp, 4Hyp, 5Hyp, HSPro, Pip, Az3Ca, Az2Ca, Acp3Ca, thz, dtc |
| Phe (F) | Trp, Tyr, phe, tyr, MePhe, MeTyr, Bhf, Bhy, Afp, hPhe, hTyr, fGly, 1npAla, 2npAla, btAla, thAla, taAla, fAla, stAla, anAla, ffAla, bzCys, iTyr, iiTyr, iiiThy, mTyr, nTyr, pTyr, OmPhe, MmPhe, PmPhe, OnPhe, MnPhe, PnPhe, OcnPhe, McnPhe, PcnPhe, OcPhe, McPhe, PcPhe, OfPhe, MfPhe, PfPhe, ObPhe, MbPhe, PbPhe, OiPhe, MiPhe, PiPhe, OpcPhe, MpcPhe, OpfPhe, MpfPhe, PmmfPhe, 5fPhe, OtPhe, MtPhe, PtPhe, PaPhe, PamPhe, MaTyr, PmmDopa, Dopa, phmPhe, Tic |
| Trp (W) | Phe, Tyr, phe, tyr, trp, MePhe, MeTyr, MeTrp, Bhf, Bhy, Bhw, Afp, hPhe, hTyr, hTrp, fGly, 1npAla, 2npAla, btAla, thAla, taAla, fAla, stAla, anAla, ffAla, bzCys, iTyr, iiTyr, iiiThy, mTyr, nTyr, pTyr, OmPhe, MmPhe, PmPhe, OnPhe, MnPhe, PnPhe, OcnPhe, McnPhe, PcnPhe, OcPhe, McPhe, PcPhe, OfPhe, MfPhe, PfPhe, ObPhe, MbPhe, PbPhe, OiPhe, MiPhe, PiPhe, OpcPhe, MpcPhe, OpfPhe, MpfPhe, PmmfPhe, 5fPhe, OtPhe, MtPhe, PtPhe, PaPhe, PamPhe, MaTyr, PmmDopa, Dopa, phmPhe, 5fTyp, 6fTyp, 1mTyp, Tic |
| Tyr (Y) | Phe, Trp, phe, tyr, MePhe, MeTyr, Bhf, Bhy, Afp, hPhe, hTyr, fGly, 1npAla, 2npAla, btAla, thAla, taAla, fAla, stAla, anAla, ffAla, bzCys, iTyr, iiTyr, iiiThy, mTyr, nTyr, pTyr, OmPhe, MmPhe, PmPhe, OnPhe, MnPhe, PnPhe, OcnPhe, McnPhe, PcnPhe, OcPhe, McPhe, PcPhe, OfPhe, MfPhe, PfPhe, ObPhe, MbPhe, PbPhe, OiPhe, MiPhe, PiPhe, OpcPhe, MpcPhe, OpfPhe, MpfPhe, PmmfPhe, 5fPhe, OtPhe, MtPhe, PtPhe, PaPho, PamPhe, MaTyr, PmmDopa, Dopa, phmPhe, Tic |

TABLE 2-continued

| Original amino acid | Examples of preservative substitution |
|---|---|
| Cys (C) | cys, MeCys, Bhcp, Pen, Ncy, HSPro, NHSEtGly, Ser, Ala, Met, Leu, Ile, Val |
| Ser (S) | Thr, ser, thr, MeSer, MeThr, Bhs, Bht, bSer, bThr, hSer, hThr, alThr, pSer, pThr |
| Thr (T) | Ser, ser, thr, MeSer, MeThr, Bhs, Bht, bSer, bThr, hSer, hThr, alThr, pSer, pThr |
| Asn (N) | Gln, asn, gln, MeAsn, MeGln, EtAsn, hGln, bAsn, bGln, Bhq, Asp, Glu |
| Gln (Q) | Asn, asn, gln, MeAsn, MeGln, EtAsn, hGln, bAsn, bGln, Bhq, Asp, Glu |
| Asp (D) | Glu, asp, glu, MeAsp, MeGlu, bGlu, bAsp, hGlu, Bhe, iAsp, iGlu, Cya, Aad, β Aad, hoGlu, caGlu, Asn, Gln |
| Glu (E) | Asp, asp, glu, MeAsp, MeGlu, bGlu, bAsp, hGlu, Bhe, iAsp, iGlu, Cya, Aad, β Aad, hoGlu, caGlu, Asn, Gln |
| Lys (K) | Arg, lys, arg, MeLys, MeArg, hLys, hArg, bLys, bArg, Bhk, Bhr, nArg, HOnArg, Oar, Omr, ntArg, 5OHLys, AHyl, Orn, 2,4-A2bu, 2,3-A2bu, A2pr, DaHea, 2pyAla, 3pAla, 4pyAla, ppAla, PaPhe, PamPhe, MaTyr, Cit, Hci |
| Arg (R) | Lys, lys, arg, MeLys, MeArg, hLys, hArg, bLys, bArg, Bhk, Bhr, nArg, HOnArg, Oar, Omr, ntArg, 5OHLys, AHyl, Orn, 2,4-A2bu, 2,3-A2bu, A2pr, DaHea, 2pyAla, 3pAla, 4pyAla, ppAla, PaPhe, PamPhe, MaTyr, Cit, Hci |
| His (H) | his, MeHis, hHis, 1mHis, 3mHis, Bhh, 2pyAla, 3pAla, 4pyAla |

II. Cyclic Peptide

The present invention provides a cyclic peptide which has an activity to specifically bind to human CTLA-4 (hereinafter referred to as the cyclic peptide of the present invention).

CTLA-4 is a known membrane protein, and its amino acid sequence is also known. A representative amino acid sequence of human CTLA-4 (NCBI Reference Sequence: NP_005205.2) is depicted in SEQ ID NO: 1. In the amino acid sequence represented by SEQ ID NO: 1, the $1^{st}$ to $35^{th}$ residues correspond to the signal peptide, and the $36^{th}$ to $223^{rd}$ residues correspond to the mature human CTLA-4. In addition, in the amino acid sequence represented by SEQ ID NO: 1, the $162^{nd}$ to $182^{nd}$ residues correspond to the transmembrane region, and the $36^{th}$ to $161^{st}$ residues correspond to the extracellular region. Preferably, the cyclic polypeptide of the present invention specifically binds to the extracellular region of mature human CTLA-4.

The term "specific binding" of a cyclic peptide to antigen X means that the binding of the cyclic peptide to antigen X is selective and distinguishable from undesired or nonspecific interactions.

The dissociation constant (Kd value) for the binding affinity of the cyclic peptide of the present invention to human CTLA-4 is generally $1\times10^{-4}$ M or less (for example, $1\times10^{-5}$ M or less, $1\times10^{-6}$ M or less, $1\times10^{-7}$ M or less or $1\times10^{-8}$ M or less).

The binding affinity can be determined by using, for example, surface plasmon resonance (BIAcore (trademark)) analysis or the like. The binding affinity is preferably measured by BLItz system (Fortebio) using SA sensor chip immobilized with biotinylated CTLA-4 protein according to the Example below.

In a preferred embodiment, the cyclic peptide of the present invention has an activity to inhibit the binding between human CTLA-4 and human CD80.

CD80 is one of the ligands for CTLA-4, and also called B7-1. A representative amino acid sequence of human CD80 (NCBI Reference Sequence: NP_005182.1) is depicted in SEQ ID NO: 2. In the amino acid sequence represented by SEQ ID NO: 2, the $1^{st}$ to $34^{th}$ residues correspond to the signal peptide, and the $35^{th}$ to $288^{th}$ residues correspond to the mature human CD80. In the amino acid sequence represented by SEQ ID NO: 2, the $243^{rd}$ to $263^{nd}$ residues correspond to the transmembrane region, and the $35^{th}$ to $242^{nd}$ residues correspond to the extracellular region. The polypeptide of the present invention preferably has an activity to inhibit the binding between the extracellular region of mature human CTLA-4 and extracellular region of human CD80.

The cyclic peptide of the present invention has an $IC_{50}$ value of, for example, $1\times10^{-3}$ M or less (preferably $1\times10^{-4}$ M or less, $1\times10^{'5}$ M or less, $1\times10^{-6}$ M or less or $1\times10^{-7}$ M or less) with respect to its inhibition of binding between human CTLA-4 and human CD80. $IC_{50}$ can be determined by using, for example, competitive ELISA, surface plasmon resonance (BIAcore (trademark)) analysis or the like. $IC_{50}$ value for the cyclic peptide of the present invention with respect to its inhibition of binding between human CTLA-4 and human CD80 is preferably measured by CTLA4:B7-1 [Biotinylated] Inhibitor Screening Assay Kit (BPS Bioscience) according to the Example below.

The cyclic peptide of the present invention is characterized in that it comprises the amino acid sequence represented formula (I):

$X_1$-His-Pro-$X_4$-Leu-$X_6$-$X_7$-$X_8$-Ser-$X_{10}$-His-Phe (I) (SEQ ID NO: 212 in the cycle, wherein $X_1$, $X_4$, $X_6$, $X_7$, $X_8$ and $X_{10}$ are each independently any amino acid.

The present invention has been completed on the basis of a finding that cyclic peptides comprising the consensus sequence represented by formula (I) above in the cycle specifically bind to human CTLA-4 and inhibit the binding between human CTLA-4 and human CD80.

As used herein, the term "cyclic peptide" means a peptide in which two amino acids within the peptide are bonded to form a cyclic structure in whole or in part. The cyclic peptide may have a molecular structure other than a cyclic structure, a chain structure in which amino acids are linked by peptide bonds, or a structure other than the peptide structure. The term "cyclic structure" means, in a linear peptide, a closed ring structure formed intramolecularly by bonding, directly or via a linker or the like, of two amino acids separated from each other by plural amino acid residues (e.g., 10 or more amino acid residues). The term "separated from each other by 10 or more amino acid residues" means that at least 10 residues of amino acids exist between two amino acids.

In the cyclic peptide of the present invention, the number of amino acids constituting a cyclic structure is not particularly limited, but is, for example, 12 or more, 13 or more, or 14 or more. The upper limit of the number of amino acids constituting the cyclic structure is not particularly limited as long as the cyclic peptide has an activity to specifically bind to human CTLA-4, but is, for example, 30 or less, 25 or less, 20 or less, or 16 or less.

The number of amino acids constituting a cyclic structure is, for example, 12 or more and 30 or less, 12 or more and 25 or less, 12 or more and 20 or less, 12 or more and 16 or less. The number of amino acids constituting a cyclic structure is, for example, 12, 13, 14, 15 or 16, and preferably 14.

The ring-closing structure in the cyclic structure is formed by an intramolecular bond between two amino acids in the peptide, although it is not particularly limited. Preferably, the ring-closing structure is formed by the covalent bonding of two amino acids, either directly or indirectly via a suitable bridged structure (the bridged structure does not contain any amino acids). Examples of a covalent bond between two amino acids include, but are not limited to, disulfide bond, peptide bond, amide bond (lactam bridge), alkyl bond, alkenyl bond, ester bond, thioester bond, ether bond, thioether bond, phosphonate ether bond, azo bond, C—S—C bond, C—N—C bond, C═N—C bond, carbamoyl bond, urea bond, thiourea bond, amine bond, thioamide bond and the like. When two amino acids are bonded in the main chain of the amino acids, the ring-closing structure is formed by peptide bond, but the covalent bond between two amino acids may be formed by bonding between the side chains of two amino acids, between the side chain and the main chain or the like.

The cyclic structure may be formed by not only a covalent bond between the N-terminal amino acid and the C-terminal amino acid of a linear peptide, but also a covalent bond between the terminal amino acid and non-terminal amino acid, or a covalent bond between non-terminal amino acids.

In one embodiment, the cyclic peptide of the present invention comprises the amino acid sequence represented by formula (II):

$X_0$-$X_1$-His-Pro-$X_4$-Leu-$X_6$-$X_7$-$X_8$-Ser-$X_{10}$-His-Phe-$X_{00}$ (II) (SEQ ID NO: 213)

wherein $X_0$, $X_1$, $X_4$, $X_6$, $X_7$, $X_8$, $X_{10}$ and $X_{00}$ are each independently any amino acid, and it is cyclized by an intramolecular bond between $X_0$ and $X_{00}$.

In one embodiment, the cyclic peptide of the present invention comprises the amino acid sequence represented by formula (III):

(Y)*m*-$X_0$-$X_1$-His-Pro-$X_4$-Leu-$X_6$-$X_7$-$X_8$-Ser-$X_{10}$-His-Phe-$X_{00}$-(Z)*n* (III) (SEQ ID NO: 214)

wherein $X_0$, $X_1$, $X_4$, $X_6$, $X_7$, $X_8$, $X_{10}$ and $X_{00}$ are each independently any amino acid, (Y)m is an amino acid sequence having a length of m amino acid(s), (Z)n is an amino acid sequence having a length of n amino acid(s), m is any integer selected from the group consisting of 0, 1 and 2, n is any integer selected from the group consisting of 0, 1 and 2, and it is cyclized by an intramolecular bond between $X_0$ and $X_{00}$.

In formulae (II) and (III), the mode of intramolecular bond between $X_0$ and $X_{00}$ is not particularly limited, but can be, for example, those described above as a covalent bond between two amino acids forming a ring-closing structure.

The following are examples of specific embodiments of cyclization by an intramolecular bond between $X_0$ and $X_{00}$.

(1) $X_0$ and $X_{00}$ are each independently an amino acid having a side chain containing thiol group, and intramolecular disulfide bond is formed between the side chain thiol group in $X_0$ and the side chain thiol group in $X_{00}$.

(2) $X_0$ and $X_{00}$ are each independently any amino acid, and amino bond (peptide bond) is formed between the main chain amino group in $X_0$ and the main chain carboxyl group in $X_{00}$.

(3) One of $X_0$ and $X_{00}$ is an amino acid having a side chain containing amino group and the other is an amino acid having a side chain containing carboxy group, and amide bond (lactam bridge) is formed between the side chain amino group and the side chain carboxyl group.

(4) $X_0$ and $X_{00}$ are each independently an amino acid having a side chain containing thiol group, and thioether bond via mesitylene is formed between the side chain thiol group in $X_0$ and the side chain thiol group in $X_{00}$ (Nature Chem. Bio. 2009, 5, 502).

(5) $X_0$ is any amino acid, $X_{00}$ is an amino acid having a side chain containing amino group, and the main chain amino group in $X_0$ and the side chain amino group in $X_{00}$ are crosslinked by disuccinimidyl glutarate (DSG) (J. Am. Chem. Soc. 2002, 124, 9972).

(6) One of $X_0$ and $X_{00}$ is an amino acid having chloroacetyl group and the other is an amino acid having a side chain containing thiol group, and thioether bond is formed between the chloroacetyl group and the thiol group (US2010/168380 A1; WO2017/217545 A1).

(7) One of $X_0$ and $X_{00}$ is an amino acid having ethynyl group (—C≡CH) and the other is an amino acid having azido group (~N3), and $X_0$ and $X_{00}$ are crosslinked via triazole ring by an intramolecular Click reaction between the ethynyl group and the azido group (US2010/168380 A1; WO2017/217545 A1).

(8) One of $X_0$ and $X_{00}$ is an amino acid having benzylamino group and the other is an amino acid having 5-hydroxyindole, and $X_0$ and $X_{00}$ are crosslinked via a fluorescent structure by an intramolecular cyclization reaction between the benzylamino group and the 5-hydroxyindole (ChemBioChem 10, 1469-1472 (2009); US2010/168380 A1; WO2017/217545 A1).

(9) One of $X_0$ and $X_{00}$ is an amino acid having —C≡C—$CH_2$—X, —C═C—$CH_2$—X or —Ar—$CH_2$—X, wherein Ar is an aromatic ring which optionally has a substituent, X is a leaving group, and examples of the leaving group include a halogen atom including Cl, Br and I, or the like, the other is an amino acid having a side chain containing thiol group, and $X_0$ and $X_{00}$ are crosslinked via a thioether bond by a condensation reaction between said —C═C—$CH_2$—X, —C═C—$CH_2$—X or —Ar—$CH_2$—X and the thiol group (US2013/316910 A1).

(10) $X_0$ and $X_{00}$ are crosslinked via a covalent bone by the method described in US2015/0080549 A1, US2015/050269 A1 or the like.

In one embodiment, $X_0$ and $X_{00}$ are each independently an amino acid having a side chain containing thiol group. The amino acid having a side chain containing thiol group is preferably cysteine (C). In this embodiment, an intramolecular bond may be formed between the side chain thiol group in $X_0$ and the side chain thiol group in $X_{00}$ (e.g., (1) or (4) above). Preferably, a disulfide bond is formed between the side chain thiol group in $X_0$ and the side chain thiol group in $X_{00}$.

In one embodiment, the cyclic peptide of the present invention comprises the amino acid sequence represented by formula (IIA):

(SEQ ID NO: 215)

(IIA)

$$\underbrace{Cys-X_1-His-Pro-X_4-Leu-X_6-X_7-X_8-Ser-X_{10}-His-Phe-Cys}_{S-S}$$

wherein $X_1$, $X_4$, $X_6$, $X_7$, $X_8$ and $X_{10}$ are each independently any amino acid.

In one embodiment, the cyclic peptide of the present invention comprises the amino acid sequence represented by formula (IIIA):

(SEQ ID NO: 216)

(IIIA)

$$(Y)m-\underbrace{Cys-X_1-His-Pro-X_4-Leu-X_6-X_7-X_8-Ser-X_{10}-His-Phe-Cys}_{S-S}-(Z)n$$

wherein $X_1$, $X_4$, $X_6$, $X_7$, $X_8$ and $X_{10}$ are each independently any amino acid, (Y)m is an amino acid sequence having a length of m amino acid(s), (Z)n is an amino acid sequence having a length of n amino acid(s), m is any integer selected from the group consisting of 0, 1 and 2, and n is any integer selected from the group consisting of 0, 1 and 2.

In formulae (I), (II), (IIA), (III) and (IIIA), $X_6$ is, preferably, a hydrophobic amino acid, a neutral hydrophilic amino acid, a basic amino acid, an amino acid having a side chain containing imino group, an amino acid having a side chain containing amido group or an amino acid having a side chain containing amino group, $X_7$ is, preferably, a hydrophobic amino acid, a neutral hydrophilic amino acid or an amino acid having a side chain containing hydroxyl group. More preferably, $X_6$ is Leu, Pro, Gln, Lys or Arg, and $X_7$ is Val, Leu, Ile or Thr. Most preferably, $X_6$ is Pro, and $X_7$ is Ile.

In one embodiment, the cyclic peptide of the present invention comprises the amino acid sequence represented by formula (IB):

$X_1$-His-Pro-$X_4$-Leu-Pro-Ile-$X_8$-Ser-$X_{10}$-His-Phe (IB) (SEQ ID NO: 217)

in the cycle, wherein $X_1$, $X_4$, $X_8$ and $X_{10}$ are each independently any amino acid.

In one embodiment, the cyclic peptide of the present invention comprises the amino acid sequence represented by formula (IIB):

$X_0$-$X_1$-His-Pro-$X_4$-Leu-Pro-Ile-$X_8$-Ser-$X_{10}$-His-Phe-$X_{00}$ (IIB) SEQ ID NO: 218 wherein $X_0$, $X_1$, $X_4$, $X_8$, $X_{10}$ and $X_{00}$ are each independently any amino acid, and the cyclic peptide is cyclized by an intramolecular bond between $X_0$ and $X_{00}$.

In one embodiment, the cyclic peptide of the present invention comprises the amino acid sequence represented by formula (IIIB):

(Y)*m*-$X_0$-$X_1$-His-Pro-$X_4$-Leu-Pro-Ile-$X_8$-Ser-$X_{10}$-His-Phe-$X_{00}$-(Z)*n* (IIIB) (SEQ ID NO: 219)

wherein $X_0$, $X_1$, $X_4$, $X_8$, $X_{10}$ and $X_{00}$ are each independently any amino acid, (Y)m is an amino acid sequence having a length of m amino acid(s), (Z)n is an amino acid sequence having a length of n amino acid(s), m is any integer selected from the group consisting of 0, 1 and 2, n is any integer selected from the group consisting of 0, 1 and 2, and wherein the peptide is cyclized by an intramolecular bond.

In one embodiment, the cyclic peptide of the present invention comprises the amino acid sequence represented by formula (IIAB):

(SEQ ID NO: 220)

(IIAB)

$$\underbrace{Cys-X_1-His-Pro-X_4-Leu-Pro-Ile-X_8-Ser-X_{10}-His-Phe-Cys}_{S-S}$$

wherein, $X_1$, $X_4$, $X_8$ and $X_{10}$ are each independently any amino acid.

In one embodiment, the cyclic peptide of the present invention comprises the amino acid sequence represented by formula (IIIAB):

(SEQ ID NO: 221)

(IIIAB)

$$(Y)m-\underbrace{Cys-X_1-His-Pro-X_4-Leu-Pro-Ile-X_8-Ser-X_{10}-His-Phe-Cys}_{S-S}-(Z)n$$

wherein $X_1$, $X_4$, $X_8$, and $X_{10}$ are each independently any amino acid, (Y)m is an amino acid sequence having a length of m amino acid(s), (Z)n is an amino acid sequence having a length of n amino acid(s), m is any integer selected from the group consisting of 0, 1 and 2, and n is any integer selected from the group consisting of 0, 1 and 2.

In formulae (I), (IB), (II), (IIA), (IIB), (IIAB), (III), (IIIA), (IIIB) and (IIIAB), $X_1$ is, preferably, a hydrophobic amino acid, a neutral hydrophilic amino acid, a basic amino acid, an aromatic amino acid, an amino acid having a side chain containing a heterocycle, an amino acid having a side chain containing sulfur atom, an amino acid having a side chain containing imino group, an amino acid having a side chain containing hydroxyl group, an amino acid having a side chain containing amido group, an amino acid having a side chain containing amino group or an amino acid having a side chain containing thiol group, $X_4$ is, preferably, a hydrophobic amino acid, a neutral hydrophilic amino acid, a basic amino acid, an aromatic amino acid, an amino acid having a side chain containing a heterocycle, an amino acid having a side chain containing sulfur atom, an amino acid having a side chain containing hydroxyl group, an amino acid having a side chain containing amido group, an amino acid having a side chain containing amino group or an amino acid having a side chain containing thiol group, $X_8$ is, preferably, a hydrophobic amino acid, a neutral hydrophilic amino acid, a basic amino acid, an aromatic amino acid, an amino acid having a side chain containing a heterocycle, an amino acid having a side chain containing sulfur atom, an amino acid having a side chain containing hydroxyl group, an amino acid having a side chain containing amido group or an amino acid having a side chain containing amino group, $X_{10}$ is, preferably, a hydrophobic amino acid, a neutral hydrophilic amino acid, a basic amino acid, an acidic amino acid, an aromatic amino acid, an amino acid having a side chain containing a heterocycle, an amino acid having a side chain containing sulfur atom, an amino acid having a side chain containing imino group, an amino acid having a side chain containing hydroxyl group, an amino acid having a side chain containing amido group, an amino acid having a side chain containing amino group, an amino acid having a side chain containing carboxy group or an amino acid having a side chain containing thiol group.

More preferably, $X_1$ is Trp, Phe, Val, Leu, Ile, Met, Pro, Ala, Gly, Ser, Gln, Lys, Arg or Cys, $X_4$ is Trp, Phe, Tyr, Val, Leu, Met, Ala, Gly, Ser, Gln, His or Cys, $X_8$ is Trp, Phe, Tyr, Val, Leu, Ile, Met, Ala, Ser, Gln, Lys, Arg or His, and $X_{10}$ is Trp, Phe, Tyr, Val, Leu, Ile, Met, Pro, Ala, Gly, Ser, Thr, Gln, Asp, Lys, Arg, His or Cys.

In formulae (III), (IIIA), (IIIB) and (IIIAB), (Z)n does not exist, when n is 0, (Z)n is an amino acid represented by $X_{+1}$, when n is 1, (Z)n consists of an amino acid sequence represented by $X_{+1}$-$X_{+2}$, when n is 2, and $X_{+1}$ and $X_{+2}$ are each independently any amino acid. Preferably n is 2.

Preferably, $X_{+1}$ is a hydrophobic amino acid, a neutral hydrophilic amino acid, a basic amino acid, an acidic amino acid, an aromatic amino acid, an amino acid having a side chain containing a heterocycle, an amino acid having a side chain containing sulfur atom, an amino acid having a side chain containing imino group, an amino acid having a side chain containing hydroxyl group, an amino acid having a side chain containing amido group, an amino acid having a side chain containing amino group or an amino acid having a side chain containing thiol group, $X_{+2}$ is a hydrophobic amino acid, a neutral hydrophilic amino acid, a basic amino acid, an aromatic amino acid, an amino acid having a side chain containing a heterocycle, an amino acid having a side chain containing sulfur atom, an amino acid having a side chain containing hydroxyl group, an amino acid having a side chain containing amido group, an amino acid having a side chain containing amino group or an amino acid having a side chain containing thiol group. More preferably, $X_{+1}$ is Trp, Val, Leu, Met, Pro, Ala, Gly, Ser, Gln, Glu, Arg or Cys, and $X_{+2}$ is Trp, Phe, Tyr, Val, Leu, Ile, Met, Ala, Gly, Ser, Gln, Lys, Arg, His or Cys.

In formulae (III), (IIIA), (IIIB) and (IIIAB), (Y)m does not exist, when m is 0, (Y)m is an amino acid represented by $X_{-1}$, when m is 1, (Y)m consists of an amino acid sequence represented by $X_{-2}$-$X_{-1}$ when m is 2, and $X_{-1}$ and $X_{-2}$ are each independently any amino acid. Preferably, m is 1 or 2.

Preferably, $X_{-1}$ is a hydrophobic amino acid, a neutral hydrophilic amino acid, basic amino acid, an acidic amino acid, an amino acid having a side chain containing hydroxyl group, an amino acid containing amino group or an amino acid having a side chain containing carboxy group, and $X_{-2}$ is a hydrophobic amino acid. More preferably, $X_{-1}$ is Gly, Ser, Lys or Asp, and $X_{-2}$ is Gly.

In one embodiment, m is 2, $X_{-1}$ is a hydrophobic amino acid, a neutral hydrophilic amino acid, an acidic amino acid, an amino acid having a side chain containing hydroxyl group or an amino acid having a side chain containing carboxyl group, and $X_{-2}$ is a hydrophobic amino acid.

In said embodiment, preferably, $X_{-2}$ is Gly, and $X_{-1}$ is Gly, Ser or Asp.

In a specific embodiment, the amino acid sequence represented by formula (I) (which includes "a partial sequence of the amino acid sequence represented by formula (II)" consisting of the amino acid sequence represented by formula (I), and "a partial sequence of the amino acid sequence represented by formula (III)" consisting of the amino acid sequence represented by formula (I)) consists of (1a) an amino acid sequence from position 4 to position 15 in the amino acid sequence represented by any of SEQ ID NOs: 30-211, or (2a) an amino acid sequence having a substitution (preferably, conservative substitution) at least at one amino acid (e.g., at 1-6, 1-5, 1-4, 1-3, 1 or 2 amino acids) corresponding to one selected from $X_1$, $X_4$, $X_6$, $X_1$, $X_8$ and $X_{10}$ in an amino acid sequence from position 4 to position 15 in the amino acid sequence represented by any of SEQ ID NOs: 30-211 (i.e., the amino acids at positions 4, 7, 9, 10, 11 and 13 in the amino acid sequence represented by any of SEQ ID NOs: 30-211).

Preferably, the amino acid sequence of (2a) above has a substitution (preferably, conservative substitution) at least at one amino acid (e.g., at 1-4, 1-3, 1 or 2 amino acids) corresponding to one selected from $X_1$, $X_4$, $X_8$ and $X_{10}$ in an amino acid sequence from position 4 to position 15 in the amino acid sequence represented by any of SEQ ID NOs: 30-211 (i.e., the amino acids at positions 4, 7, 11 and 13 in the amino acid sequence represented by any of SEQ ID NOs: 30-211).

In a specific embodiment, the amino acid sequence represented by formula (II) (which includes "a partial sequence of the amino acid sequence represented by formula (III)" consisting of the amino acid sequence represented by formula (II)) consists of (1b) an amino acid sequence from position 3 to position 16 in the amino acid sequence represented by any of SEQ ID NOs: 30-211, or (2b) an amino acid sequence having a substitution (preferably, conservative substitution) at least at one amino acid (e.g., at 1-6, 1-5, 1-4, 1-3, 1 or 2 amino acids) corresponding to one selected from $X_1$, $X_4$, $X_6$, $X_7$, $X_8$ and $X_{10}$ in an amino acid sequence from position 3 to position 16 in the amino acid sequence represented by any of SEQ ID NOs: 30-211 (i.e., the amino acids at positions 4, 7, 9, 10, 11 and 13 in the amino acid sequence represented by any of SEQ ID NOs: 30-211).

Preferably, the amino acid sequence of (2b) above has a substitution (preferably, conservative substitution) at least at one amino acid (e.g., at 1-4, 1-3, 1 or 2 amino acids) corresponding to one selected from $X_1$, $X_4$, $X_8$ and $X_{10}$ in an amino acid sequence from position 3 to position 16 in the amino acid sequence represented by any of SEQ ID NOs: 30-211 (i.e., the amino acids at positions 4, 7, 11 and 13 in the amino acid sequence represented by any of SEQ ID NOs: 30-211).

In said embodiment, the side chain thiol group in the Cys at position 1 and the side chain thiol group in the Cys at position 14 in the amino acid sequence of (1b) or (2b) form an intramolecular bond. The binding manner is not particularly limited, but it is preferably a disulfide bond or a thioether bond via mesitylene (Nature Chem. Bio. 2009, 5, 502), and more preferably a disulfide bond.

In a specific embodiment, the amino acid sequence represented by formula (III) consists of (1c) an amino acid sequence from position 3 to position 18 in the amino acid sequence represented by any of SEQ ID NOs: 30-211, or (2c) an amino acid sequence having a substitution (preferably, conservative substitution) at least at one amino acid (e.g., at 1-8, 1-7, 1-6, 1-5, 1-4, 1-3, 1 or 2 amino acids) corresponding to one selected from $X_1$, $X_4$, $X_6$, $X_7$, $X_8$, $X_{10}$, $X_{+1}$ and $X_{+2}$ in an amino acid sequence from position 3 to position 18 in the amino acid sequence represented by any of SEQ ID NOs: 30-211 (i.e., the amino acids at positions 4, 7, 9, 10, 11, 13, 17 and 18 in the amino acid sequence represented by any of SEQ ID NOs: 30-211).

Preferably, the amino acid sequence of (2c) above has a substitution (preferably, conservative substitution) at least at one amino acid (e.g., at 1-6, 1-5, 1-4, 1-3, 1 or 2 amino acids) corresponding to one selected from $X_1$, $X_4$, $X_8$, $X_{10}$, $X_{+1}$ and $X_{+2}$ in an amino acid sequence from position 3 to position 18 in the amino acid sequence represented by any of SEQ ID NOs: 30-211 (i.e., the amino acids at positions 4, 7, 11, 13, 17 and 18 in the amino acid sequence represented by any of SEQ ID NOs: 30-211).

In said embodiment, the side chain thiol group in the Cys at position 1 and the side chain thiol group in the Cys at position 14 in the amino acid sequence of (1c) or (2c) form an intramolecular bond. The binding manner is not particularly limited, but it is preferably a disulfide bond or a thioether bond via mesitylene (Nature Chem. Bio. 2009, 5, 502), and more preferably a disulfide bond.

In a specific embodiment, the amino acid sequence represented by formula (III) consists of (1d) the amino acid sequence represented by any of SEQ ID NOs: 30-211, or (2d) an amino acid sequence having a substitution (preferably, conservative substitution) at least at one amino acid (e.g., at 1-10, 1-9, 1-8, 1-7, 1-6, 1-5, 1-4, 1-3, 1 or 2 amino acids) corresponding to one selected from $X_{-2}$, $X_{-1}$, $X_1$, $X_4$, $X_6$, $X_7$, $X_8$, $X_{10}$, $X_{+1}$ and $X_{+2}$ in the amino acid sequence represented by any of SEQ ID NOs: 30-211 (i.e., the amino acids at positions 1, 2, 4, 7, 9, 10, 11, 13, 17 and 18 in the amino acid sequence represented by any of SEQ ID NOs: 30-211).

Preferably, the amino acid sequence of (2d) above has a substitution (preferably, conservative substitution) at least at one amino acid (e.g., at 1-8, 1-7, 1-6, 1-5, 1-4, 1-3, 1 or 2 amino acids) corresponding to one selected from $X_{-2}$, $X_{-1}$, $X_1$, $X_4$, $X_8$, $X_{10}$, $X_{+1}$ and $X_{+2}$ in the amino acid sequence represented by any of SEQ ID NOs: 30-211 (i.e., the amino acids at positions 1, 2, 4, 7, 11, 13, 17 and 18 in the amino acid sequence represented by any of SEQ ID NOs: 30-211).

In one embodiment, the amino acid sequence of (2d) above preferably has a substitution (preferably, conservative substitution) at least at one amino acid (e.g., at 1-6, 1-5, 1-4, 1-3, 1 or 2 amino acids) corresponding to one selected from $X_1$, $X_4$, $X_8$, $X_{10}$, $X_{+1}$ and $X_{+2}$ in the amino acid sequence represented by any of SEQ ID NOs: 30-211 (i.e., the amino acids at positions 4, 7, 11, 13, 17 and 18 amino acids in the amino acid sequence represented by any of SEQ ID NOs: 30-211).

In said embodiment, the side chain thiol group in the Cys at position 3 and the side chain thiol group in the Cys at position 16 in the amino acid sequence of (1 d) or (2d) form an intramolecular bond. The binding manner is not particularly limited, but it is preferably a disulfide bond or a thioether bond via mesitylene (Nature Chem. Bio. 2009, 5, 502), and more preferably a disulfide bond.

In one embodiment, the cyclic peptide of the present invention comprises the amino acid sequence represented by formula (II):

$X_0$-$X_1$-His-Pro-$X_4$-Leu-$X_6$-$X_7$-$X_8$-Ser-$X_{10}$-His-Phe-$X_{00}$ (II) (SEQ ID NO: 213)

wherein $X_1$ is Trp, Phe, Val, Leu, Ile, Met, Pro, Ala, Gly, Ser, Gln, Lys, Arg or Cys, $X_4$ is Trp, Phe, Tyr, Val, Leu, Met, Ala, Gly, Ser, Gln, His or Cys, $X_6$ is Leu, Pro, Gln, Lys or Arg, $X_7$ is Val, Leu, Ile or Thr, $X_8$ is Trp, Phe, Tyr, Val, Leu, Ile, Met, Ala, Ser, Gln, Lys, Arg or His, $X_{10}$ is Trp, Phe, Tyr, Val, Leu, Ile, Met, Pro, Ala, Gly, Ser, Thr, Gln, Asp, Lys, Arg, His or Cys, $X_0$ and $X_{00}$ are each independently any amino acid, and the peptide is cyclized by an intramolecular bond between $X_0$ and $X_{00}$.

In said embodiment, preferably, $X_6$ is Pro, and $X_7$ is Ile.

As a specific embodiment of the cyclization by an intramolecular bond between $X_0$ and $X_{00}$, those described above can be exemplified. Preferably, $X_0$ and $X_{00}$ are each independently an amino acid having a side chain containing thiol group, and more preferably, $X_0$ and $X_{00}$ are Cys. The binding manner between the side chain thiol group in $X_0$ and the side chain thiol group in $X_{00}$ is not particularly limited, but it is preferably a disulfide bond or a thioether bond via mesitylene (Nature Chem. Bio. 2009, 5, 502), and more preferably a disulfide bond.

In one embodiment, the cyclic peptide of the present invention comprises the amino acid sequence represented by formula (II):

$X_0$-$X_1$-His-Pro-$X_4$-Leu-$X_6$-$X_7$-$X_8$-Ser-$X_{10}$-His-Phe-$X_{00}$ (II) (SEQ ID NO: 213 wherein the partial sequence ($X_1$-His-Pro-$X_4$-Leu-$X_6$-$X_7$-$X_8$-Ser-$X_{10}$-His-Phe (SEQ ID NO: 212) consists of (1e) an amino acid sequence from the 4th to 15th positions in the amino acid sequence represented by any of SEQ ID NOs: 30-211, or (2e) an amino acid sequence having a substitution (preferably, conservative substitution) at least at one amino acid (e.g., at 1-6, 1-5, 1-4, 1-3, 1 or 2 amino acids) corresponding to one selected from $X_1$, $X_4$, $X_6$, $X_7$, $X_8$ and $X_{10}$ in an amino acid sequence from position 4 to position 15 in the amino acid sequence represented by any of SEQ ID NOs: 30-211 (i.e., the amino acids at positions 4, 7, 9, 10, 11 and 13 in the amino acid sequence represented by any of SEQ ID NOs: 30-211), $X_0$ and $X_{00}$ are each independently any amino acid, and the peptide is cyclized by an intramolecular bond between $X_0$ and $X_{00}$.

Preferably, the amino acid sequence of (2e) above has a substitution (preferably, conservative substitution) at least at one amino acid (e.g., at 1-4, 1-3, 1 or 2 amino acids) corresponding to one selected from $X_1$, $X_4$, $X_8$ and $X_{10}$ in an amino acid sequence from position 4 to position 15 in the amino acid sequence represented by any of SEQ ID NOs: 30-211 (i.e., the amino acids at positions 4, 7, 11 and 13 in the amino acid sequence represented by any of SEQ ID NOs: 30-211).

As a specific embodiment of the cyclization by an intramolecular bond between $X_0$ and $X_{00}$, those described above can be exemplified. Preferably, $X_0$ and $X_{00}$ are each independently an amino acid having a side chain containing thiol group, and more preferably, $X_0$ and $X_{00}$ are Cys. The binding manner between the side chain thiol group in $X_0$ and the side chain thiol group in $X_{00}$ is not particularly limited, but it is preferably a disulfide bond or a thioether bond via mesitylene (Nature Chem. Bio. 2009, 5, 502), and more preferably a disulfide bond.

In one embodiment, the cyclic peptide of the present invention comprises the amino acid sequence represented by formula (III):

(Y)*m*-$X_0$-$X_1$-His-Pro-$X_4$-Leu-$X_6$-$X_7$-$X_8$-Ser-$X_{10}$-His-Phe-$X_{00}$-(Z)*n* (III) (SEQ ID NO: 214)

wherein $X_1$ is Trp, Phe, Val, Leu, Ile, Met, Pro, Ala, Gly, Ser, Gln, Lys, Arg or Cys, $X_4$ is Trp, Phe, Tyr, Val, Leu, Met, Ala, Gly, Ser, Gln, His or Cys, $X_6$ is Leu, Pro, Gln, Lys or Arg, $X_7$ is Val, Leu, Ile or Thr, $X_8$ is Trp, Phe, Tyr, Val, Leu, Ile, Met, Ala, Ser, Gln, Lys, Arg or His, $X_{10}$ is Trp, Phe, Tyr, Val, Leu, Ile, Met, Pro, Ala, Gly, Ser, Thr, Gln, Asp, Lys, Arg, His or Cys, (Y)m is an amino acid sequence having a length of m amino acid(s), (Z)n is an amino acid sequence having a length of n amino acid(s), m is any integer selected from the group consisting of 0, 1 and 2, n is any integer selected from the group consisting of 0, 1 and 2, $X_0$ and $X_{00}$ are each independently any amino acid, and the peptide is cyclized by an intramolecular bond between $X_0$ and $X_{00}$.

In said embodiment, preferably, $X_6$ is Pro, and $X_7$ is Ile.

As a specific embodiment of the cyclization by an intramolecular bond between $X_0$ and $X_{00}$, those described above can be exemplified. Preferably, $X_0$ and $X_{00}$ are each independently an amino acid having a side chain containing thiol group, and more preferably, $X_0$ and $X_{00}$ are Cys. The binding manner between the side chain thiol group in $X_0$ and the side chain thiol group in $X_{00}$ is not particularly limited, but it is preferably a disulfide bond or a thioether bond via mesitylene (Nature Chem. Bio. 2009, 5, 502), and more preferably a disulfide bond.

n is preferably 2, (Z)n consists of an amino acid sequence represented by $X_{+1}$-$X_{+2}$, and $X_{+1}$ and $X_{+2}$ are each independently any amino acid. Preferably, $X_{+1}$ is Trp, Val, Leu, Met, Pro, Ala, Gly, Ser, Gln, Glu, Arg or Cys, $X_{+2}$ is Trp, Phe, Tyr, Val, Leu, Ile, Met, Ala, Gly, Ser, Gln, Lys, Arg, His or Cys.

m is preferably 2, (Y)m consists of an amino acid sequence represented by $X_{-2}$-$X_{-1}$, and $X_{-1}$ and $X_{-2}$ are each independently any amino acid. Preferably, $X_{-1}$ is Gly, Ser or Asp, and $X_{-2}$ is Gly.

In one embodiment, the cyclic peptide of the present invention comprises an amino acid sequence represented by formula (III):

(Y)*m*-$X_0$-$X_1$-His-Pro-$X_4$-Leu-$X_6$-$X_7$-$X_8$-Ser-$X_{10}$-His-Phe-$X_{00}$-(Z)*n* (III) (SEQ ID NO: 214)

wherein the partial sequence ($X_1$-His-Pro-$X_4$-Leu-$X_6$-$X_7$-$X_8$-Ser-$X_{10}$-His-Phe (SEQ ID NO: 212)) consists of (1f) an amino acid sequence from position 4 to position 15 in the amino acid sequence represented by any of SEQ ID NOs: 30-211, or (2f) an amino acid sequence having a substitution (preferably, conservative substitution) at least at one amino acid (e.g., at 1-6, 1-5, 1-4, 1-3, 1 or 2 amino acids) corresponding to one selected from $X_1$, $X_4$, $X_6$, $X_7$, $X_8$ and $X_{10}$ in an amino acid sequence from position 4 to position 15 in the amino acid sequence represented by any of SEQ ID NOs: 30-211 (i.e., the amino acids at positions 4, 7, 9, 10, 11 and 13 in the amino acid sequence represented by any of SEQ ID NOs: 30-216), (Y)m is an amino acid sequence having a length of m amino acid(s), (Z)n is an amino acid sequence having a length of n amino acid(s), m is any integer selected from the group consisting of 0, 1 and 2, n is any integer selected from the group consisting of 0, 1 and 2, $X_0$ and $X_{00}$ are each independently any amino acid, and the peptide is cyclized by an intramolecular bond between $X_0$ and $X_{00}$.

Preferably, the amino acid sequence of (2f) above has a substitution (preferably, conservative substitution) at least at one amino acid (e.g., at 1-4, 1-3, 1 or 2 amino acids) corresponding to one selected from $X_1$, $X_4$, $X_8$ and $X_{10}$ in an amino acid sequence from position 4 to position 15 in the amino acid sequence represented by any of SEQ ID NOs: 30-211 (i.e., the amino acids at positions 4, 7, 11 and 13 in the amino acid sequence represented by any of SEQ ID NOs: 30-211).

As a specific embodiment of the cyclization by an intramolecular bond between $X_0$ and $X_{00}$, those described above can be exemplified. Preferably, $X_0$ and $X_{00}$ are each independently an amino acid having a side chain containing thiol group, and more preferably, $X_0$ and $X_{00}$ are Cys. The binding manner between the side chain thiol group in $X_0$ and the side chain thiol group in $X_{00}$ is not particularly limited, but it is preferably a disulfide bond or a thioether bond via mesitylene (Nature Chem. Bio. 2009, 5, 502), and more preferably a disulfide bond.

n is preferably 2, (Z)n consists of an amino acid sequence represented by $X_{+1}$-$X_{+2}$, and $X_{+1}$ and $X_{+2}$ are each independently any amino acid. Preferably, $X_{+1}$ is Trp, Val, Leu, Met, Pro, Ala, Gly, Ser, Gln, Glu, Arg or Cys, $X_{+2}$ is Trp, Phe, Tyr, Val, Leu, Ile, Met, Ala, Gly, Ser, Gln, Lys, Arg, His or Cys.

m is preferably 2, $(Y)m$ consists of an amino acid sequence represented by $X_{-2}$-$X_{-1}$, and $X_{-1}$ and $X_{-2}$ are each independently any amino acid. Preferably, $X_{-1}$ is Gly, Ser or Asp, and $X_{-2}$ is Gly.

The length (amino acid length) of the cyclic peptide of the present invention is not particularly limited as long as it has an activity to specifically bind to human CTLA-4, but it is, for example, 12 or more, 13 or more, 14 or more, 15 or more, 16 or more, 17 or more or 18 or more. The upper limit of the length of the cyclic peptide of the present invention is not particularly limited as long as the peptide has an activity to specifically bind to human, but it is, for example, 2000 or less, 1000 or less, 500 or less, 250 or less or 100 or less. In one embodiment, the length (amino acid length) of the cyclic peptide of the present invention is 12, 13, 14, 15, 16, 17 or 18.

The cyclic peptide of the present invention may comprise an additional sequence at N-terminal side and/or C-terminal side of an amino acid sequence represented by formulae (I), (IB), (II), (IIA), (IIB), (IIAB), (III), (IIIA), (IIIB) or (IIIAB). As the additional sequence, for example, an amino acid sequence of a tag that facilitates detection, purification or the like of the peptide can be mentioned. Examples of the tag include, but not limited to, Flag tag, histidine tag, c-Myc tag, HA tag, AU1 tag, GST tag, MBP tag, fluorescence protein tag (e.g., GFP, YFP, RFP, CFP, BFP etc.), immunoglobulin Fc tag and the like.

The cyclic peptide of the present invention is preferably isolated. Being "isolated" means that an operation to remove components other than the component of interest has been applied to the state of natural presence. The purity of the isolated cyclic peptide of the present invention determined by, for example, electrophoresis (e.g., SDS-PAGE, isoelectric focusing electrophoresis (IEF), capillary electrophoresis) or chromatography (e.g., ion exchange or reverse-phase HPLC) and the like is generally 50% or more, preferably 70% or more, more preferably 90% or more, most preferably 95% or more (e.g., substantially 100%). For a method to evaluate the purity of a compound, see Flatman et al., J. Chromatogr. B 848:79-87 (2007).

The cyclic peptide of the present invention may be modified by acylation (e.g., acylation of N-terminal amino group), amidation (e.g., amidation of C-terminal carboxyl group), phosphorylation, methylation, acetylation, adenylation, ADP-ribosylation, esterification, halogenation, glycosylation, PEG addition, alkyl chain addition or the like. In addition, the cyclic peptide of the present invention may be fused with other peptides or proteins.

The cyclic peptide of the present invention may be labeled by a labeling agent. As the labeling agent, for example, biotin, enzyme, fluorescent substance, luminescent substance, radioisotope, toxin or the like may be used. As the enzyme, a stable enzyme having a high specific activity is preferable, for example, β-galactosidase, β-glucosidase, alkaline phosphatase, peroxidase, malate dehydrogenase or the like may be used. As the fluorescent substance, for example, fluorescamine, fluorescein isothiocyanate or the like may be used. As the luminescent substance, for example, luminol, luminol derivative, luciferin, lucigenin or the like may be used. As the radioisotope, for example, $^{125}I$, $^{131}I$, $^{3}H$, $^{14}C$ or the like may be used.

The cyclic peptide of the present invention includes the salt form. As a salt of the cyclic peptide, a salt with physiologically acceptable base or acid may be used, and examples of the salt include addition salts with an inorganic acid (hydrochloric acid, hydrobromic acid, hydriodic acid, sulfuric acid, phosphoric acid or the like), addition salts with an organic salt (p-toluenesulfonic acid, methanesulfonic acid, oxalic acid, p-bromophenylsulfonic acid, carboxylic acid, succinic acid, citric acid, benzoic acid, acetic acid or the like), addition salts with an inorganic base (ammonium hydroxide or alkali- or alkaline-earth metal hydroxides, carbonates, bicarbonates or the like), amino acid and the like.

The cyclic peptide of the present invention can be produced by using known peptide synthesis techniques. Examples of a method for synthesizing cyclic peptides include chemical synthesis methods such as solid-phase synthesis method, liquid-phase synthesis method, and hybrid methods; genetic recombination methods; and translation synthesis methods using cell-free translation system.

The synthesis of the cyclic peptide of the present invention by a translation synthesis method using a cell-free translation system can be prepared by preparing a nucleic acid encoding the cyclic peptide, and translating the nucleic acid in the cell-free translation system. When a cyclic peptide cyclized by a disulfide bond is synthesized in a cell-free translation system, an optimized reaction solution supplemented with oxidized glutathione, reduced glutathione, and DsbC, a molecular chaperon may be used (Shimizu et al., (2005) Methods, vol. 36, p. 299-304). A person having ordinary skill in the art can appropriately design a nucleic acid encoding a cyclic peptide based on the amino acid sequence of the cyclic amino acid. The nucleic acid may be DNA or RNA. Natural amino acids as well as non-natural amino acids can be efficiently introduced to the cyclic peptide by using tRNA aminoacylated with non-natural amino acids. The cyclization of the peptide can be performed by know methods, for example, as described above as an example of ring-closing structure in the cyclic structure.

After the synthesis reaction, the cyclic peptide of the present can be isolated or purified by using purification methods generally used in the field of peptide, for example, solvent extraction, distillation, column chromatography, liquid chromatography, recrystallization or the like, in combination.

The cyclic peptide of the present invention can specifically bind to CTLA-4 and inhibit a function of human CTLA-4. Accordingly, the cyclic peptide of the present invention is useful as a CTLA-4 inhibitor (preferably, a human CTLA-4 inhibitor). The present invention provides a CTLA-4 inhibitor (preferably, a human CTLA-4 inhibitor) comprising the cyclic peptide of the present invention described above (hereinafter referred to as the CTLA-4 inhibitor of the present invention). A function of CTLA-4 in a subject (e.g., human) can be inhibited by administering an effective amount of the cyclic peptide of the present invention to the subject. A function of CTLA-4 can be inhibited by contacting CTLA-4 with an effective amount of the cyclic peptide of the invention in vivo or in vitro. The function of CTLA-4 includes binding to its ligands, CD80 or CD86. The CTLA-4 inhibitor of the present invention inhibits binding of CTLA-4 to its ligand (CD80 or CD86) and suppresses the subsequent downstream cascade (biological responses). The CTLA-4 inhibitor of the present invention inhibits binding of CTLA-4 (e.g., human CTLA-4) to CD80 (e.g., human CD80) and/or binding of CTLA-4 (e.g., human CTLA-4) to CD86 (e.g., human CD86), preferably inhibits binding of CTLA-4 (e.g., human CTLA-4) to CD80 (e.g., human CD80).

CTLA-4 is a receptor expressed on the surface of T cells (e.g., cytotoxic T cells) and is known to compete with the co-stimulatory molecule CD28 to bind to CD80 and CD86 on antigen-presenting cells, thereby suppressing CD28 co-stimulatory signals and inhibiting T cell activation. The CTLA-4 inhibitor of the present invention inhibits binding of CTLA-4 to CD80, thereby blocking the suppression of co-stimulatory signals and activating T cells (e.g., cytotoxic T cells). Accordingly, the present invention also provides a T cell activating agent (preferably, a cytotoxic T cell activating agent) comprising the cyclic peptide of the present invention described above (hereinafter referred to as the T cell activating agent of the present invention). T cells in a subject (e.g., human) can be activated by administering an effective amount of the cyclic peptide of the present invention.

In addition, it is also known that inhibition of the binding of CTLA-4 to CD80 and CD86 on antigen-presenting cells enhances anti-tumor immunity by blocking suppressive regulation in activated T cells and enhancing proliferation, activation and cytotoxicity or the like of tumor antigen-specific T cells. Accordingly, the CTLA-4 inhibitor of the present invention is useful for enhancing anti-tumor immunity and preventing or treating a tumor. The present invention provides an agent for preventing or treating a tumor/an agent for enhancing anti-tumor immunity comprising the cyclic peptide of the present invention. A tumor in a subject (e.g., human) can be prevented or treated by administering an effective amount of the cyclic peptide of the present invention to the subject. In addition, anti-tumor immunity in a subject (e.g., human) can be enhanced by administering an effective amount of the cyclic peptide of the present invention to the subject. The subject is preferably a human tumor patient. The cyclic peptide of the present invention may be useful for treating a metastatic cancer, suppressing metastasis or suppressing recurrence of a tumor.

As used herein, the term "effective amount" means an amount which results in an aimed effect (e.g., therapeutic effective) on the subject, and means, for example, that in the subject who has received the amount, the symptom of the disease or condition is alleviated, mitigated, eliminated or the development of the symptom of the disease or condition is delayed or inhibited compared with a subject who has not received the amount. An effective amount can be appropriately determined by doctors in view of the age, weight, sex and the severity of the disease or the like of the subject.

As used herein, the term "treatment of a tumor" means bringing about at least one effect of reduction of a tumor size, suppression of tumor growth (retardation or stopping), suppression of tumor metastasis (retardation or stopping), suppression of the recurrence (prevention or retardation), and alleviation of one or a plurality of symptoms associated with cancer.

The type of tumor is not particularly limited, but examples include leukemia (for example, acute myelogenous leukemia, chronic myelogenous leukemia, acute lymphocytic leukemia, chronic lymphocytic leukemia), malignant lymphoma (Hodgkin lymphoma, non-Hodgkin lymphoma (for example, adult T cell leukemia, follicular lymphoma, diffuse large B-cell lymphoma)), multiple myeloma, myelodysplastic syndrome, head or neck cancer, esophageal cancer, esophageal adenocarcinoma, stomach cancer, colorectal cancer, colorectal cancer, rectal cancer, liver cancer (for example, hepatoma), gallbladder/bile duct cancer, biliary cancer, pancreatic cancer, thyroid cancer, lung cancer (for example, non-small cell lung cancer (for example, squamous non-small cell lung cancer, non-squamous non-small cell lung cancer), small cell lung cancer), breast cancer, ovarian cancer (for example, serous ovarian cancer), cervical cancer, endometrial cancer, endometrial cancer, vaginal cancer, vulvar cancer, renal cancer (for example, renal cell cancer), urothelial cancer (for example, bladder cancer, upper urinary tract cancer), prostate cancer, testicular tumor (for example, germ cell tumor), osteosarcoma/soft tissue sarcoma, skin cancer (for example, uveal malignant melanoma, malignant melanoma, Merkel cell carcinoma), glioma, brain tumor (for example, glioblastoma), and pleural mesothelioma and cancer of unknown primary).

The cyclic peptides of the invention can be formulated into a pharmaceutical composition according to the conventional methods (for example, Remington's Pharmaceutical Science, latest edition, Mark Publishing Company, Easton, U.S.A). Pharmaceutical dosage forms include, for example, a liquid (for example injection), a dispersant, a suspension, a tablet, a pill, a particle, a suppository, a powder, a fine granule, a granule, a capsule, a syrup, a troche, an inhalant, an ointment, an eye-drop, a nasal drop, an ear-drop, a gel patch and the like. In the pharmaceutical composition, the cyclic peptide of the present invention may be used directly as an active ingredient, or a pharmaceutically acceptable carrier and/or additive may be contained. For example, a surfactant (PEG, Tween or the like), an excipient, an anti-oxidant (ascorbic acid or the like), a coloring, a fragrance, a preservative, a stabilizer, a buffer (phosphoric acid, citric acid, other organic acids or the like), a chelating agent (EDTA or the like), a suspending agent, an isotonizing agent, a binder, a disintegrant, a lubricant, a plasticizer, a taste masking agent or the like may be contained. Although they are not particularly limited, the pharmaceutical composition may also contain other carriers as appropriate. Specific examples include light anhydrous silicic acid, lactose, crystalline cellulose, mannitol, starch, carmellose calcium, carmellose sodium, hydroxypropyl cellulose, hydroxypropyl methylcellulose, polyvinyl acetaldiethylaminoacetate, polyvinyl pyrrolidone, gelatin, medium-chain triglyceride, polyoxyethylene hydrogenated castor oil 60, sucrose, carboxymethyl cellulose, cornstarch, inorganic salts and the like. In addition, other small molecular weight polypeptide, a protein such as serum albumin, gelatin and immunoglobulin, an amino acid may be contained. When an aqueous solution for injection is formulated, the cyclic peptide of the present invention is dissolved in, for example, isotonic solution containing saline, glucose or other auxiliary agents. Examples of the auxiliary agent include D-sorbitol, D-mannose, D-mannitol, and sodium chloride, and may be used in combination with suitable solubilizing agents, for example, alcohol (ethanol etc.), polyalcohol (propylene glycol, PEG etc.), non ionic surfactant (polysorbate 80, HCO-50) and the like.

The content of the cyclic peptide of the present invention in the pharmaceutical composition is not particularly limited but is, for example, about 0.00001-100 wt %, 0.0001-99.9% or the like of the whole pharmaceutical composition.

The pharmaceutical composition of the present invention can be administered both orally and parenterally. For example, it is administered to a patient by injection or transdermal administration. It can be administered systemically or topically by, for example, intravenously injection, intramuscular injection, subcutaneous injection or other dosage forms of injection. It may also be injected at or near the treatment site topically or intramuscularly. Examples of the dosage form of transdermal administration include an ointment, gel, a cream, a plaster, a patch and the like, which can be administered systemically or topically.

All references cited in the present specification, including publication, patent document and the like, are hereby incorporated individually and specifically by reference, to the extent that the entireties thereof have been specifically disclosed herein.

The present invention is explained in more detail in the following by referring to Examples, which are not to be construed as limitative.

Examples

1. Method (1) Construction of a Gene Library for Ribosome Display Encoding Randomized Cyclic Peptides To construct a cyclic peptide library, a library of oligo DNAs was synthesized, in which the oligo DNAs encode randomized amino acid sequences consisting of 12 amino acids flanked by two cysteines, to which a FLAG tag sequence is added to the 5' side and a c-Myc tag sequence is added to the 3' side (FIG. 1). The randomized amino acid residues are encoded by 12 NNS codons, wherein N is G, C, T or A and S is G or C.

Furthermore, an oligo DNA of 5'UTR sequence was synthesized, where the 5'UTR sequence comprises T7 promoter and SD sequence necessary for performing ribosome display (the formula below) (FASMAC). FLAG sequence (underlined portion) was added to the 3' end as a region overlapped with oligo DNAs in the cyclic peptide library.

```
5' UTR:
                                        (SEQ ID NO: 5)
GAAATTAATACGACTCACTATAGGGAGACCACAACGGTTTCCCTCTAGAA

ATAATTTTGTTTAACTTTAAGAAGGAGATATACCAATGGACTATAAAGAT

GACGATGACAAA
```

Using a M13KO7-derived phage genome as a template, a partial sequence of M13 phage genIII (g3p) was amplified by PCR with the primer set below and KOD Plus DNA Polymerase (TOYOBO) (denature: 94° C. for 10 seconds, annealing: 57° C. for 30 seconds, extension: 68° C. for 60 seconds, cycles: 25 cycles), and purified by NeucleoSpin Gel and PCR Clean-up (Takara).

```
Myc-g3p:
                                        (SEQ ID NO: 6)
GAGCAGAAGCTGATCTCTGAGGAGGATCTGAAGCTTGAATATCAAGGCCA

ATCGTCTGAC

g3p-SecMstop:
                                        (SEQ ID NO: 7)
CTCGAGTTATTCATTAGGTGAGGCGTTGAGGGCCAGCACGGATGCCTTGC

GCCTGGCTTATCCAGACGGGCGTGCTGAATTTTGCGCCGGAAACGTCACC

AATGAAAC
```

PCR reaction solution (KOD Plus DNA Polymerase, 500 μL total) containing 1 pmol each of the synthesized oligo DNAs (5'UTR, and the oligo DNA library encoding randomized cyclic peptides) and g3p gene fragment was prepared and subjected to PCR for 15 cycles (denature: 94° C. for 10 seconds, annealing: 58° C. for 30 seconds, extension: 68° C. for 60 seconds). The reaction solution (50 μL×10 tubes) was additionally added with two primers below (10 pmol each) and 1 μL of KOD Plus DNA Polymerase and subjected to PCR for 10 cycles (denature: 94° C. for 10 seconds, annealing: 58° C. for 30 seconds, extension: 68° C. for 60 seconds).

```
5'primer:
                                        (SEQ ID NO: 9)
GAAATTAATACGACTCACTATAGGGAGACCACAACGGTTTCCCTCTAG

SecMstop:
                                        (SEQ ID NO: 8)
GGATTAGTTATTCATTAGGTGAGGCGTTGAGG
```

The reaction product was separated by electrophoresis using 1% agarose, and the amplified band in which all the intended fragments were connected was cut out and purified by NeucleoSpin Gel and PCR clean-up (Takara) to finally obtain a gene library for ribosome display encoding randomized cyclic peptides.

(2) Biotinylation of Antigen Protein

CTLA-4 protein (Recombinant Human CTLA4-Fc chimera: R&D systems) was biotinylated according to the standard protocol for EZ-Link NHS-PEO12-Biotin (PIERCE). Biotinylation of CTLA-4 protein was confirmed mobility shift of the band in SDS-PAGE. The concentration of biotinylated CTLA-4 protein was measured by using BCA Protein Assay Kit (PIERCE)

(3) In Vitro Transcription

1 μg of the purified gene library DNA was transcribed into mRNA with 20 μl of In vitro transcription Kit (T7 Ribomax™ Express Large Scale RNA Production System: Promega), and the obtained mRNA library was column-purified (NucleoSpin RNA clean-up: Takara).

(4) In Vitro Selection

According to the method of Shimizu et al., a cell-free translation system (PUREsystem) for use in ribosome display was prepared as a reaction solution partially optimized for S—S bond formation (Shimizu et al., (2005) Methods, vol. 36, p. 299-304). Oxidized glutathione (GSSG: SIGMA) and reduced glutathione (GSH: SIGMA) were added at a final concentration of 3 mM each, and a molecular chaperon, DsbC, was added at a final concentration of 0.63 μM. Prepared reaction solution (100 μl) was added with 10 pmol of mRNA library and incubated at 37° C. for 30 min to form ribosome display complexes (peptide-ribosome-mRNA complexes). The reaction product was added with 500 μL of ice-cold wash buffer solution (50 mM Tris-OAc, pH7.5, 150 mM NaCl, 50 mM $Mg(OAc)_2$, 0.5% Tween 20, 1 μg/mL *Saccharomyces cerevisiae* total RNA (Sigma)).

Dynabeads MyOne Streptavidin T1 magnetic beads (100 μL slurry, Invitrogen) pre-blocked overnight with 5% SuperBlock at 4° C. was trapped with MagneSphere Magnetic Separation Stand (Promega) and washed twice with 500 μL of wash buffer solution. 100 pmol of biotinylated antigen protein was added and immobilized on the magnetic beads at 4° C. After 60 min, the magnetic beads were trapped with MagneSphere Magnetic Separation Stand (Promega) and washed 3 times with 500 μL of wash buffer solution. The recovered magnetic beads were added with post-translation reaction solution containing ribosome display complexes (peptide-ribosome-mRNA complexes) and stirred with rotation at 4° C. for 1 hr. A supernatant was discarded by MagneSphere Magnetic Separation Stand (Promega), and the recover magnetic beads were added with 1 mL of wash buffer solution and stirred with rotation at 4° C. for 5 min. This series of operations were repeated 30 times, and then the recovered magnetic beads were added with 100 μL of Elution buffer solution (50 mM Tris-HCl, pH7.4, 150 mM NaCl, 50 mM EDTA) and allowed to stand at 4° C. for 10 min to release mRNA from the magnetic beads. The magnetic beads were trapped by MagneSphere Magnetic Separation Stand (Promega) to recover a supernatant containing mRNA, and the mRNA was purified by NucleoSpin RNA clean-up (Takara). A part of purified mRNA was reacted with RNA-direct SYBR Green Realtime PCR Master Mix (TOYOBO) and quantified by using Light Cycler 480 (Roche).

(5) RT-PCR

The purified mRNA was reverse-transcribed into cDNA by Transcriptor High Fidelity cDNA Synthesis Kit (Roche), and PCR (50 μL total, denature: 94° C. for 15 seconds, annealing: 57° C. for 30 seconds, extension: 68° C. for 60 seconds, 30 cycles) was performed using the obtained cDNA as a template with KOD Plus DNA Polymerase. The used primers are shown below.

```
<reverse transcription reverse primer>
                                        (SEQ ID NO: 10)
Myc R: CAGATCCTCCTCAGAGATCAGC

<PCR primers>
                                        (SEQ ID NO: 11)
FLAG F: ATGGACTATAAAGATGACGATGACAAAGG

                                        (SEQ ID NO: 10)
Myc R: CAGATCCTCCTCAGAGATCAGC
```

The reaction solution after PCR was separated by electrophoresis using 2% agarose, and a band with corresponding size was cut out and purified by NeucleoSpin Gel and PCR clean-up (Takara)

(6) Reconstruction of Genes for Ribosome Display

The reconstruction of genes for ribosome display of the second or later round was performed as follows. PCR reaction solution (200 μL total) containing purified genes after RT-PCR (1 pmol), 5'UTR (1 pmol), g3p gene fragment (1 pmol), 5' primer (10 pmol), SecMstop (10 pmol) and KOD Plus DNA Polymerase (TOYOBO) was prepared and subjected to PCR for 15 cycles (denature: 94° C. for 15 seconds, annealing: 57° C. for 30 seconds, extension: 68° C. for 60 seconds). The reaction product was separated by electrophoresis using 1% agarose, and a band with all the genes connected was cut out and purified by NeucleoSpin Gel and PCR clean-up (Takara).

Figure 3:
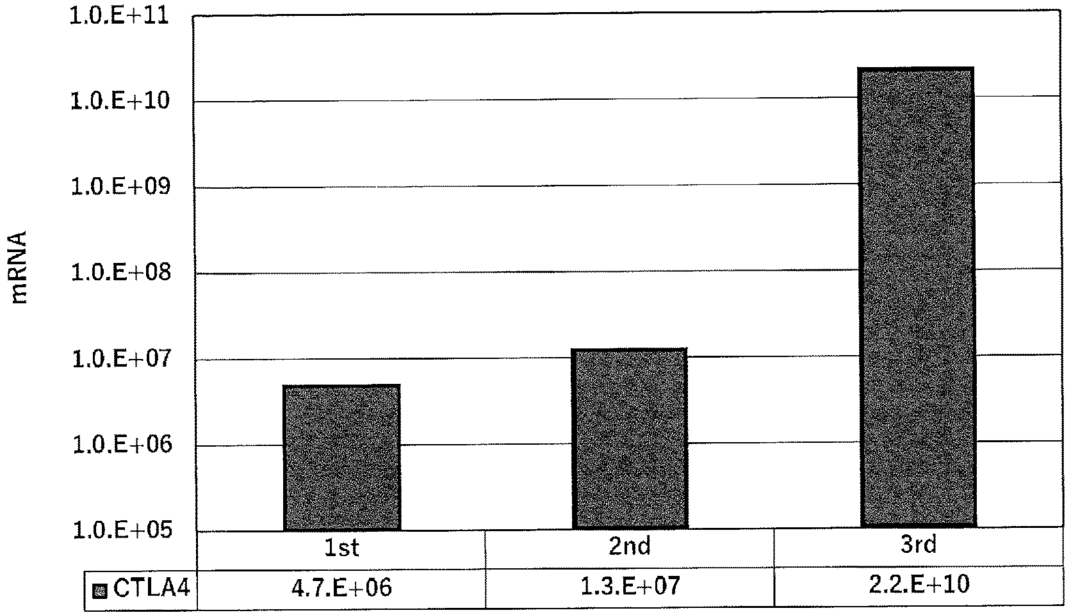
FIG. 3 The results of the selection experiment by ribosome display against CTLA-4-Fc are shown. The amount of recovered mRNA got increased with each selection round.

A series of operations including in vitro transcription, in vitro Selection, RT-PCR, and reconstruction of genes for ribosome display was considered as one round, and three rounds were conducted. The amount of recovered mRNA is shown in FIG. 3.

(7) Subcloning

Figure 2:
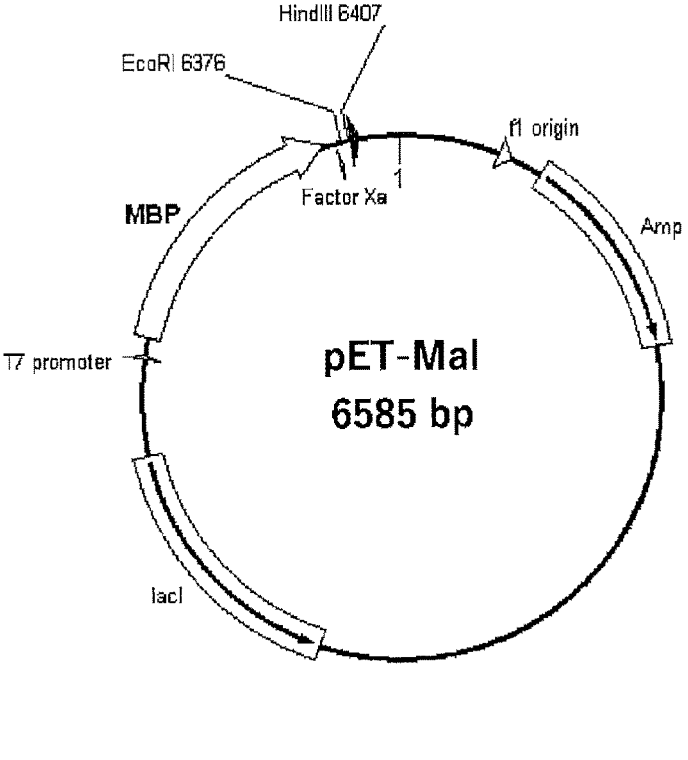
FIG. 2 A schematic of pET-Mal vector is shown. MBP fusion protein-expression vector was constructed by inserting a cyclic peptide gene at EcoRI-HindIII site located downstream of the MBP gene.

The recovered genes after three rounds were cloned into *E. coli* expression vector pET-Mal (FIG. 2) as a N-terminal MBP fusion protein. In brief, PCR reaction solution (KOD Plus DNA Polymerase, 100 μL total) containing the cDNAs obtained by reverse transcription of mRNAs recovered after three rounds,

```
primer Eco1-(-M)-FLAG_F:
                              (SEQUENCE ID NO: 12)
CCGAATTCGACTATAAAGATGACGATGACAAAGGC,
and

primerMyc-Hind3_R:
                              (SEQUENCE ID NO: 13)
AAAAAAAAAAGCTTCAGATCCTCCTCAGAGATC
```

was prepared and subjected to PCR amplification (denature: 94° C. for 15 seconds, annealing: 57° C. for 30 seconds, extension: 68° C. for 30 seconds) for 20 cycles, and the PCR product was purified by NeucleoSpin Gel and PCR clean-up (Takara). The primer Eco1-(-M)-FLAG_F introduces EcoRI cleavage site for 5' side and the primer Myc-Hind3_R introduces HindIII cleavage site for 3' side. 1 μg of the purified PCR product and an expression vector were treated with EcoRI (TOYOBO) and HindIII (TOYOBO) at 37° C. for 1 hour, the reaction product was separated by electrophoresis using 2% agarose, the corresponding bands were cut out and purified by NeucleoSpin Gel and PCR clean-up (Takara). The insert and the vector were mixed at a mol ratio of 5:1 and reacted at room temperature for 30 min by using LigaFast Rapid DNA Ligation Kit (Promega). *E. coli* BL21 (DE3) competent cells prepared by Z-competent *E. coli* Transformation Set (ZYMO RESEARCH) were transformed with the ligation product, and cultured on LB agar plates containing ampicillin (final concentration 50 μg/mL) at 37° C., overnight.

(8) Base Sequence Analysis 94 subcloned *E. coli* single colonies were subjected to the base sequence analysis. The following sequence primer was used.

```
                              (SEQ ID NO: 14)
pET-MALseqF: CCAGAAAGGTGAAATCATGCCGAACATC
```

(9) Ribosome Display Pull Down Assay for Enriched Clones

From the clones that were found to be enriched in sequence analysis (Table 3), genes for ribosome display were reconstituted and the ribosome display pull down assay was performed using the same method as for the in vitro selection described above (scaled down to 10 μL) (FIG. 4).

TABLE 3

| Number of enriched clones | clone name | clone No. | Sequence Cys | 1 | 2 | 3 | 4 | 5 | 6 | 7 | 8 | 9 | 10 | 11 | 12 | Cys | SEQ ID NO: |
|---|---|---|---|---|---|---|---|---|---|---|---|---|---|---|---|---|---|
| 51 | H12SSI-Ctla4-3-02 | 2 | C | M | H | P | F | L | L | V | V | S | H | H | F | C | 15 |
| 6 | H12SSI-Ctla4-3-51 | 3 | C | G | L | G | Q | G | Y | W | F | K | V | W | F | C | 16 |
| 4 | H12SSI-Ctla4-3-33 | 6 | C | A | K | N | F | G | Y | W | Y | H | Q | W | F | C | 17 |
| 3 | H12SSI-Ctla4-3-80 | 5 | C | G | A | G | K | G | F | W | F | K | V | W | F | C | 18 |
| 2 | H12SSI-Ctla4-2-23 | 1 | C | G | F | H | D | G | F | W | Y | N | V | W | F | C | 19 |

TABLE 3-continued

| Number of enriched clones | clone name | clone No. | Cys | 1 | 2 | 3 | 4 | 5 | 6 | 7 | 8 | 9 | 10 | 11 | 12 | Cys | SEQ ID NO: |
|---|---|---|---|---|---|---|---|---|---|---|---|---|---|---|---|---|---|
| 2 | H12SSI-Ctla4-3-90 | 4 | C | G | V | N | L | G | F | W | F | N | V | W | F | C | 20 |
| 2 | H12SSI-Ctla4-3-38 | 7 | C | I | I | Q | G | Q | Y | W | W | N | I | W | H | C | 21 |

(10) Overexpression and purification of CTLA-4-binding clone (H12SSI-Ctla4-3-02)

For clones that were found to specifically bind to CTLA-4 in the ribosome display pull down assay, N-terminal MBP fusion proteins were overexpressed in *E. coli* (BL21BE3) and purified. *E. coli* transformants were inoculated into 200 mL of 2×YT medium containing ampicillin (final concentration 50 μg/mL), incubated at 37° C. for 3-5 hours (OD600=0.5-0.8), and then added with IPTG (final concentration 0.5 mM) and incubated at 25° C. overnight. The grown *E. coli* cells were collected by centrifugation, resuspended in 60 mL of lysis buffer (20 mM Tris HCl pH 7.5, 500 mM NaCl), and disrupted by a sonicator (Bioruptor UCD-250). The disrupted cell suspension was centrifuged, the supernatant was collected, filtered through a 0.22 μm filter, and subjected to affinity purification by MBPTrap (GE Healthcare). The purified protein solution was subjected to a buffer exchange into PBS by a dialysis membrane. Purity was confirmed by SDS-PAGE and protein concentration was determined using the BCA Protein Assay Kit (PIERCE).

(11) Affinity Measurement of CTLA-4-Binding Clone (H12SSI-Ctla4-3-02)

The affinity of the purified CTLA-4 binding clone (H12SSI-Ctla4-3-02) to CTLA-4 was measured using BLItz system (forte Bio). All operations were performed according to the instruction manual of the BLItz system. The biotinylated CTLA-4 protein was immobilized on the SA sensor chip via streptavidin.

(12) Preparation of Error-Prone Library for Affinity Maturation of CTLA-4 Binding Clone (H12SSI-Ctla4-3-02)

Error-Prone Library was prepared by the method of Zhao et al. (Nat. Biotechnol., (1998) vol. 16, p. 258-261) using H12SSI-Ctla4-3-02, which was confirmed to bind specifically to CTLA-4, as a template. The following PCR primer set was used.

```
<5' primer>
                                (SEQUENCE ID NO: 11)
FLAG F: ATGGACTATAAAGATGACGATGACAAAGG

<3' primer>
                                     (SEQ ID NO: 10)
Myc R: CAGATCCTCCTCAGAGATCAGC
```

When the above primer set is used for Error-Prone PCR, mutations are also introduced in the GG linker portion immediately after the FLAG tag sequence and in the GG linker portion immediately before the c-Myc tag sequence (see FIG. 1). For the mutant products obtained by Error-Prone PCR, genes for ribosome display were reconstructed by the same method described above.

(13) Affinity Maturation of CTLA-4-Binding Clone (H12SSI-Ctla4-3-02)

The basic operation of ribosome display was performed in the same manner as described above. Detailed experimental conditions for Affinity Maturation are indicated below. 2 μL of Nanolink streptavidin magnetic beads (SoluLink) were used as magnetic beads to immobilize the antigen, and 1 mL of CTLA-4 protein solution (1 μM) was used as a wash solution. The amount of biotinylated CTLA-4 immobilized on the magnetic beads was 10 pmol in the 1$^{st}$ round, 2 pmol in the 2$^{nd}$ round, and 1 pmol in the 3$^{rd}$ round, respectively. The washing period was 2 hours for the 1$^{st}$ round, 19 hours for the 2$^{nd}$ round, and 67 hours for the 3$^{r}$d round. The number of wash cycle was one time (2 hours) in the 1$^{st}$ round, two times (about every 10 hours) in the rd round, and six times (about every 10 hours) in the 3rd round. After each round of RT-PCR, Error-Prone PCR was performed in the same manner as described above.

(14) Evaluation of Binding after Affinity Maturation Selection by ELISA

After each round of Affinity Maturation, the cyclic peptide genes were recovered and subcloned into pET-Mal vector (FIG. 2) in the same manner as described above to perform base sequence analysis. For the 94 single colonies analyzed for sequence, *E. coli* transformants were inoculated into 100 μL of 2×YT medium containing ampicillin (final concentration 50 μg/mL), incubated at 37° C. for 3-5 hours (OD600=0.5-0.8), then added with IPTG (final concentration 0.5 mM) and incubated at 25° C. overnight. 10 μL of *E. coli* cultured medium was added with 90 μL of PBS and 40 μL of lysis reagent (20 μL BugBuster Protein Extraction Reagent (Novagen), 20 μL Lysozyme solution 2.5 mg/mL) to lyse *E. coli* cells for 1 hour at room temperature. The cell lysate was added with 40 μL of 12.5% skim milk solution (TBST) and blocked for 1 hour at room temperature. In parallel, antigen protein was immobilized overnight at 4° C. in 384-well plates at 100 ng/20 μL per well, and each well was washed twice with 100 μL/well of TBST, added with 100 μL/well of 5% skim milk solution (TBST) for blocking for 1 hour at room temperature, and washed twice with 100 μL/well of TBST to obtain antigen-immobilized plates. 20 μL/well of blocking-treated *E. coli* extract was added to the antigen-immobilized plates and gently stirred at room temperature using a plate mixer. After 1 hour, the plates were washed 5 times with 100 μL/well of TBST, 20 μL/well of anti-FLAG M2-HRP conjugate (1:2000 dilution, Sigma) was added and gently stirred on a plate mixer for 1 hour at room temperature. The plates were washed 5 times with 100 μL/well of TBST, and binding of cyclic peptides to the antigen was detected by 20 μL/well of chromogenic substrate (0.4 mg/mL 3,3',5,5'-Tetramethyl-benzidine, 0.01% hydrogen peroxide). After 15 minutes of reaction at room temperature, the reaction was stopped with 20 μL/well of 2N HCl, and absorbance at 450 nm was measured using a plate reader (infinite F200: TECAN) (Table 5).

(15) Affinity Measurement of CTLA-4 Binding Clones after Affinity Maturation (EC50 Measurement)

For the top 27 clones with the highest ELISA signals among the clones obtained in the Affinity Maturation selection experiment, N-terminal MBP fusion proteins were overexpressed by *E. coli* and purified using the same method described above, and the EC50 values were calculated by ELISA.

For each of the CTLA-4 binding clones obtained by Affinity Maturation, purified N-terminal MBP fusion protein solution (400 μg/mL) was prepared and samples serially 2-fold diluted with PBS were prepared. CTLA-4 was immobilized overnight at 4° C. in 384-well plates at 100 ng/20 μL per well, and each well was washed twice with 100 μL/well of TBST, added with 100 μL/well of 5% skim milk solution (TBST) for blocking for 1 hour at room temperature, and washed twice with 100 μL/well of TBST to obtain antigen-immobilized plates. 20 μL/well of serially-diluted N-terminal MBP fusion protein solution was added to the antigen-immobilized plates and gently stirred at room temperature using a plate mixer. After 1 hour, the plates were washed 5 times with 100 μL/well of TBST, 20 μL/well of anti-FLAG M2-HRP conjugate (1:2000 dilution, Sigma) was added and gently stirred on a plate mixer for 1 hour at room temperature. Further, the plates were washed 5 times with 100 μL/well of TBST, and binding of N-terminal MBP fusion proteins to the antigen was detected by 20 μL/well of chromogenic substrate (0.4 mg/mL 3,3',5,5'-Tetramethylbenzidine, 0.01% hydrogen peroxide). After 15 minutes of reaction at room temperature, the reaction was stopped with 20 μL/well of 2N HCl, and absorbance at 450 nm was measured using a plate reader (infinite F200: TECAN). The graph was plotted with the vertical axis as the absorbance of ELISA and the horizontal axis as the concentration of N-terminal MBP fusion protein of the CTLA4-binding clones (FIG. 5), and the EC50 was calculated from the obtained binding curve (Table 6).

(16) Measurement of Inhibitory Activity of CTLA-4 Binding Clones (IC50 Measurement)

Among the clones obtained in the Affinity Maturation selection experiment, clone #19 (CMHPFLPIVSHHFCER) (SEQ ID NO: 22), which has high affinity to CTLA-4 in EC50 measurement, was measured for its activity to inhibit binding of CTLA-4 to CD80. The measurement of inhibitory activity was performed using the CTLA4:B7-1[Biotinylated] Inhibitor Screening Assay Kit (BPS Biosciences). The experiment was performed according to the standard protocol attached to the kit.

(17) Measurement of Affinity and Inhibitory Activity of Synthetic Peptides

For the high-affinity CTLA-4 binding clone #19 (CMHPFLPIVSHHFCER) (SEQ ID NO: 22) obtained by Affinity Maturation and the original clone H12SSI-Ctla4-3-02 (CMHPFLLVVSHHFC) (SEQ ID NO: 15), peptides with PEG4-biotin added via N-terminal lysine residue and cyclized by S—S bond between two cysteine residues (biotinylated clone #19: Biotin-PEG4-KCMHPFLPIVSHHFCER (SEQ ID NO: 24)/biotinylated H12SSI-Ctla4-3-02: Biotin-PEG4-KCMHPFLLVVSHHFC (SEQ ID NO: 23)) were chemically synthesized (Toray Research Center). Affinity for CTLA-4 was measured using the BLItz system (forte Bio). All operations were performed according to the instruction manual of the BLItz system. The biotinylated peptides were immobilized on the SA sensor chip via streptavidin.

In addition, peptides with glycine added to the N-terminus (Gly-clone #19: GCMHPFLPIVSHHFCER (SEQ ID NO: 26)/Gly-H12SSI-Ctla4-3-02: GCMHPFLLVVSHHFC (SEQ ID NO: 25)) were chemically synthesized for the measurement of inhibitory activity. Inhibitory activity was measured using the CTLA4:B7-1 [Biotinylated] Inhibitor Screening Assay Kit (BPS Biosciences) as described above.

(18) Identification of Amino Acids Essential for CTLA-4 Binding in High Affinity Clones by Alanine Scanning Using the CTLA-4 binding clone #10 (CLHPFLPIVSHHFCGR) (SEQ ID NO: 27), which had high affinity, as the original clone, a series of oligo DNAs encoding mutants in which any one amino acid residue except cysteine was sequentially replaced with alanine were synthesized and each oligo DNA was subcloned into pET-Mal vector (FIG. 2), and the binding activity of the alanine substitution mutants to CTLA-4 was evaluated by ELISA as described above.

(19) Affinity Maturation with Random Library

Oligo DNAs of a library were synthesized (see below), in which amino acid residues (positions 1, 4, 8, 10, +1 and +2) (corresponding to $X_1$, $X_1$, $X_8$, $X_{10}$, $X_{+1}$ and $X_{+2}$) other than those essential or advantageous for CTLA-4 binding (2H, 3P, 5L, 6P, 7I, 9S, 11H, 12F) identified by alanine scanning were randomized (NNS).

```
(No. 19) NNS6:
                                          (SEQ ID NO: 28)
GACTATAAAGATGACGATGACAAAGGCGGTTGCNNSCATCCANNSCTGC

CGATANNSTCANNSCATTTCTGTNNSNNSGGATCCGAGCAGAAGCTGAT

CTCTGAGGAGGATCTG
```

The gene format for ribosome display (coupling with 5' UTR and g3p) was prepared in the same manner as described above.

Affinity Maturation was performed in the same manner as described above. The amount of biotinylated CTLA-4 immobilized on the magnetic beads was 10 pmol in the $1^{st}$ round, 2 pmol in the $2^{nd}$ round, and 1 pmol in the $3^{nd}$-$5^{th}$ rounds, respectively. The washing period was 2 hours for the $1^{st}$ round, 19 hours for the 2nd round, 67 hours for the $3^{nd}$ round, 140 hours for the $4^{th}$ round, and 340 hours for the 5th round. Washing frequency was 1 time (2 hours) in the 1st round, 2 times (every 10 hours) in the 2nd round, 6 times (every 10 hours) in the 3rd round, 14 times (every 10 hours) in the 4th round, and 36 times (every 10 hours) in the 5th round.

2. Results and Discussion (1) Results of In Vitro Selection and Sequence Analysis As shown in FIG. 3, sufficient mRNA enrichment was observed in three rounds of selection experiments. The results of sequence analysis (Table 3) indicate that multiple enriched clones were obtained. About half (51/94) of the clones were H12SSI-Ctla4-3-02 (Clone No. 2).

(2) Ribosome Display Pull Down Assay of Enriched Clones

Figure 4:
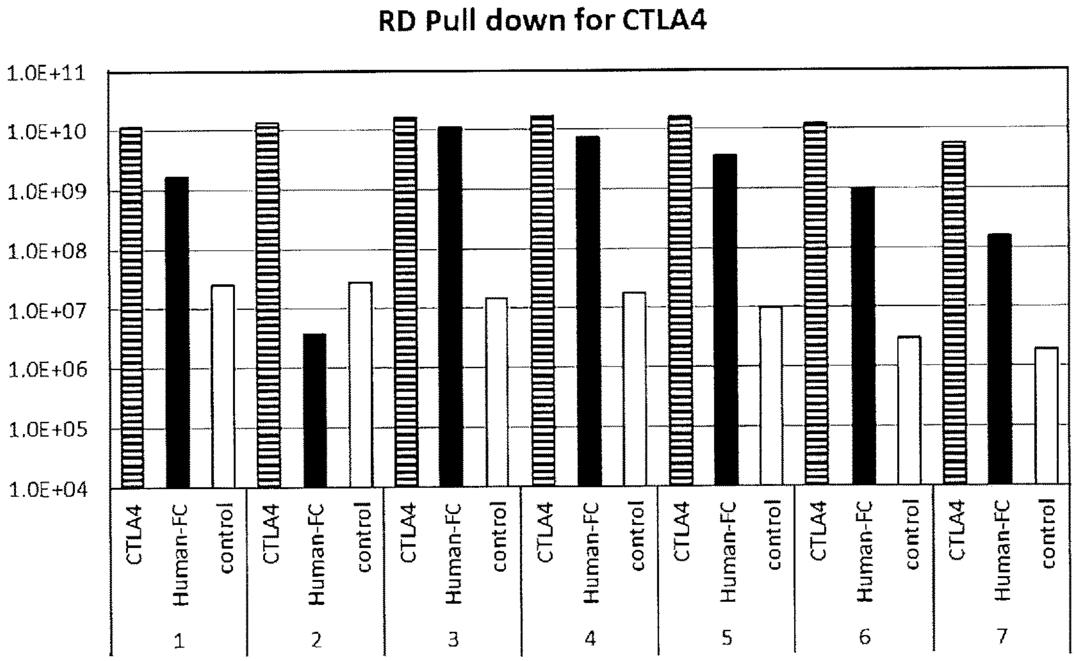
FIG. 4 The results of the ribosome display pull down assay are shown. All clones except No. 2 are clones specifically binding to Fc moiety, since they bound to both CTLA-4 Fc and Human Fc.

The CTLA-4 binding activity of the seven clones (Table 3) enriched by in vitro selection was evaluated by Ribosome Display pull down assay (FIG. 4). The results showed that only Clone No. 2 (H12SSI-Ctla4-3-02), which had the highest number in enrichment in the sequence analysis, bound specifically to CTLA-4, while all other clones were specific binders to the Fc moiety of CTLA-4-Fc used as an antigen.

(3) Large Scale Purification and Affinity Measurement of H12SSI-Ctla4-3-02

H12SSI-Ctla4-3-02, which was confirmed to bind specifically to CTLA-4, was overexpressed in *E. coli* as an MBP fusion protein, subjected to affinity purification, and the affinity for CTLA-4 was determined by the BLItz system. The results suggest that H12SSI-Ctla4-3-02 has a much lower affinity for CTLA-4 (KD=3.88 μM) than the existing anti-CTLA-4 antibody ipilimumab (KD=5.25±3.62 nM, Assessment Report For Yervoy, European Medicines Agency), as shown in Table 4.

TABLE 4

| $k_a$ [1/Ms] | $k_d$ [1/s] | $R^2$ | $K_D$ |
|---|---|---|---|
| 3.18E+03 | 1.23E−02 | 0.9932 | 3.88E−06 |

(4) Affinity Maturation of H12SSI-Ctla4-3-02

An Error-Prone Library was prepared based on H12SSI-Ctla4-3-02, and Affinity Maturation selection experiments were performed. The cyclic peptide genes obtained in each round were subcloned, 94 single colonies were cultured in 96-well plates, and the CTLA-4 binding activity of each MBP-fused cyclic peptide was examined by ELISA. Clones confirmed to have binding activity (S/N ratio not less than 2) by ELISA were summarized in Table 5.

TABLE 5

| | | | ELISA MBP-fusion | | | GlyGly | | Cys | Loop | | | |
|---|---|---|---|---|---|---|---|---|---|---|---|---|
| No. | Round | Sample name | Orencia | SA | S/N(SA) | −2 | −1 | 0 | 1 | 2 | 3 | 4 |
| | | original clone | 0.2278 | 0.0536 | 4.3 | G | G | C | M | H | P | F |
| #1 | 1st | C4-302mat-1-1-24 | 0.7799 | 0.0529 | 14.7 | G | G | C | M | H | P | F |
| #2 | 2nd | C4-302mat-2-100-18 | 0.857 | 0.0533 | 16.1 | G | G | C | M | H | P | F |
| #3 | 3rd | C4-302mat-3-1-48 | 0.9029 | 0.0617 | 14.6 | G | G | C | M | H | P | F |
| #4 | 3rd | C4-302mat-3-100-37 | 1.1667 | 0.0647 | 18.0 | G | G | C | M | H | P | F |
| #5 | 1st | C4-302mat-1-1-35 | 0.5339 | 0.0475 | 11.2 | G | G | C | M | H | P | F |
| #6 | 3rd | C4-302mat-3-1-22 | 1.1053 | 0.0584 | 18.9 | G | G | C | M | H | P | F |
| #7 | 3rd | C4-302mat-3-100-27 | 0.9267 | 0.0559 | 16.6 | G | G | C | M | H | P | F |
| #8 | 2nd | C4-302mat-2-1-2 | 1.2008 | 0.0546 | 23.5 | G | G | C | L | H | P | F |
| #9 | 2nd | C4-302mat-2-1-38 | 0.8075 | 0.0492 | 16.4 | G | G | C | L | H | P | F |
| #10 | 3rd | C4-302mat-3-100-44 | 1.1444 | 0.0617 | 18.5 | G | G | C | L | H | P | F |
| #11 | 3rd | C4-302mat-3-1-45 | 0.6887 | 0.0615 | 11.2 | G | G | C | R | H | P | F |
| #12 | 3rd | C4-302mat-3-100-20 | 0.2214 | 0.0599 | 3.7 | G | G | C | V | H | P | F |
| #13 | 3rd | C4-302mat-3-100-9 | 0.7793 | 0.054 | 14.4 | G | G | C | K | H | P | F |
| #14 | 3rd | C4-302mat-3-1-10 | 0.5861 | 0.0569 | 10.3 | G | G | C | K | H | P | Y |
| #15 | 2nd | C4-302mat-2-1-27 | 0.7848 | 0.0571 | 13.7 | G | G | C | M | H | P | Y |
| #16 | 3rd | C4-302mat-3-100-12 | 1.1792 | 0.0607 | 19.4 | G | G | C | M | H | P | Y |
| #17 | 2nd | C4-302mat-2-1-3 | 0.8018 | 0.0542 | 14.8 | G | G | C | M | H | P | F |
| #18 | 2nd | C4-302mat-2-100-27 | 1.2889 | 0.0512 | 25.2 | G | G | C | M | H | P | F |
| #19 | 3rd | C4-302mat-3-1-27 | 1.0658 | 0.0591 | 18.0 | G | G | C | M | H | P | F |
| #20 | 3rd | C4-302mat-3-1-23 | 1.2104 | 0.0614 | 19.7 | G | G | C | M | H | P | F |
| #21 | 3rd | C4-302mat-3-1-32 | 0.6564 | 0.0578 | 11.4 | G | G | C | M | H | P | F |
| #23 | 3rd | C4-302mat-3-1-31 | 0.868 | 0.0656 | 13.2 | G | S | C | M | H | P | F |
| #24 | 3rd | C4-302mat-3-1-5 | 0.4377 | 0.0739 | 5.9 | G | G | C | M | H | P | F |
| #25 | 3rd | C4-302mat-3-1-12 | 0.9496 | 0.053 | 17.9 | G | G | C | M | H | P | F |
| #22 | 3rd | C4-302mat-3-1-35 | 0.2989 | 0.0569 | 5.3 | G | G | C | M | H | P | F |
| #26 | 2nd | C4-302mat-2-1-35 | 0.9038 | 0.0504 | 17.9 | G | G | C | M | H | P | F |
| #27 | 2nd | C4-302mat-2-100-4 | 0.5451 | 0.0587 | 9.3 | G | G | C | M | H | P | F |
| #28 | 1st | C4-302mat-1-1-21 | 0.1553 | 0.0572 | 2.7 | G | G | C | I | H | P | F |
| #29 | 1st | C4-302mat-1-100-23 | 0.25 | 0.0467 | 5.4 | G | G | C | V | H | P | F |
| #30 | 2nd | C4-302mat-2-1-40 | 0.3661 | 0.0529 | 6.9 | G | G | C | M | H | P | F |
| #31 | 3rd | C4-302mat-3-1-2 | 1.4489 | 0.0662 | 21.9 | G | G | C | M | H | P | Y |
| #32 | 1st | C4-302mat-1-1-37 | 0.6653 | 0.0467 | 14.2 | G | G | C | M | H | P | F |
| #33 | 3rd | C4-302mat-3-1-14 | 0.9848 | 0.0634 | 15.5 | G | G | C | M | H | P | F |
| #34 | 2nd | C4-302mat-2-1-12 | 0.5104 | 0.06 | 8.5 | G | G | C | K | H | P | F |
| #35 | 2nd | C4-302mat-2-1-24 | 0.1402 | 0.0576 | 2.4 | G | G | C | M | H | P | F |
| #36 | 3rd | C4-302mat-3-1-8 | 0.5553 | 0.0674 | 8.2 | G | G | C | M | H | P | F |
| #37 | 2nd | C4-302mat-2-1-37 | 0.1198 | 0.0514 | 2.3 | G | G | C | M | H | P | F |
| #38 | 2nd | C4-302mat-2-100-33 | 0.1165 | 0.0499 | 2.3 | G | S | C | M | H | P | F |
| #39 | 3rd | C4-302mat-3-1-9 | 0.5735 | 0.0653 | 8.8 | G | G | C | M | H | P | Y |
| #40 | 2nd | C4-302mat-2-100-24 | 0.2268 | 0.0566 | 4.0 | G | G | C | M | H | P | Y |
| #41 | 3rd | C4-302mat-3-1-15 | 0.3511 | 0.0655 | 5.4 | G | G | C | M | H | P | Y |
| #42 | 3rd | C4-302mat-3-1-25 | 0.2637 | 0.062 | 4.3 | G | D | C | K | H | P | Y |

TABLE 5-continued

| | | | | | | | | | | | |
|---|---|---|---|---|---|---|---|---|---|---|---|
| #43 | 2nd | C4-302mat-2-100-40 | 0.2036 | 0.0516 | 3.9 | G | G | C | M | H | P | F |
| #44 | 3rd | C4-302mat-3-1-11 | 0.4123 | 0.0509 | 8.1 | G | G | C | M | H | P | F |
| #45 | 3rd | C4-302mat-3-100-39 | 0.136 | 0.0585 | 2.3 | G | G | C | K | H | P | F |

| | | | Loop | | | | | | | | Cys | GlyGly | | SEQ ID |
|---|---|---|---|---|---|---|---|---|---|---|---|---|---|---|
| No. | Round | Sample name | 5 | 6 | 7 | 8 | 9 | 10 | 11 | 12 | G | +1 | +2 | NO: |
| | | original clone | L | L | V | V | S | H | H | F | C | G | G | 29 |
| #1 | 1st | C4-302mat-1-1-24 | L | P | V | V | S | H | H | F | C | G | G | 30 |
| #2 | 2nd | C4-302mat-2-100-18 | L | P | V | V | S | H | H | F | C | R | G | 31 |
| #3 | 3rd | C4-302mat-3-1-48 | L | P | V | V | S | H | H | F | C | G | A | 32 |
| #4 | 3rd | C4-302mat-3-100-37 | L | P | V | V | S | H | H | F | C | G | R | 33 |
| #5 | 1st | C4-302mat-1-1-35 | L | P | V | A | S | H | H | F | C | G | G | 34 |
| #6 | 3rd | C4-302mat-3-1-22 | L | P | V | A | S | H | H | F | C | G | R | 35 |
| #7 | 3rd | C4-302mat-3-100-27 | L | P | V | A | S | H | H | F | C | A | G | 36 |
| #8 | 2nd | C4-302mat-2-1-2 | L | P | V | V | S | H | H | F | C | G | D | 37 |
| #9 | 2nd | C4-302mat-2-1-38 | L | P | L | V | S | H | H | F | C | G | G | 38 |
| #10 | 3rd | C4-302mat-3-100-44 | L | P | I | V | S | H | H | F | C | G | R | 39 |
| #11 | 3rd | C4-302mat-3-1-45 | L | P | I | V | S | R | H | F | C | R | G | 40 |
| #12 | 3rd | C4-302mat-3-100-20 | L | P | V | V | S | H | H | F | C | R | G | 41 |
| #13 | 3rd | C4-302mat-3-100-9 | L | P | V | V | S | H | H | F | C | G | G | 42 |
| #14 | 3rd | C4-302mat-3-1-10 | L | P | V | A | S | H | H | F | C | R | G | 43 |
| #15 | 2nd | C4-302mat-2-1-27 | L | P | V | I | S | H | H | F | C | G | G | 44 |
| #16 | 3rd | C4-302mat-3-100-12 | L | P | V | I | S | H | H | F | C | G | R | 45 |
| #17 | 2nd | C4-302mat-2-1-3 | L | P | V | T | S | H | H | F | C | G | G | 46 |
| #18 | 2nd | C4-302mat-2-100-27 | L | P | I | V | S | H | H | F | C | G | S | 47 |
| #19 | 3rd | C4-302mat-3-1-27 | L | P | I | V | S | H | H | F | C | E | R | 48 |
| #20 | 3rd | C4-302mat-3-1-23 | L | P | I | A | S | L | H | F | C | G | R | 49 |
| #21 | 3rd | C4-302mat-3-1-32 | L | P | I | L | S | H | H | F | C | A | G | 50 |
| #23 | 3rd | C4-302mat-3-1-31 | L | P | V | A | S | R | H | F | C | G | R | 51 |
| #24 | 3rd | C4-302mat-3-1-5 | L | P | V | V | S | R | H | F | C | G | G | 52 |
| #25 | 3rd | C4-302mat-3-1-12 | L | P | V | V | S | R | H | F | C | G | R | 53 |
| #22 | 3rd | C4-302mat-3-1-35 | L | Q | T | V | S | H | H | F | C | G | G | 54 |
| #26 | 2nd | C4-302mat-2-1-35 | L | Q | V | V | S | H | H | F | C | G | S | 55 |
| #27 | 2nd | C4-302mat-2-100-4 | L | Q | V | V | S | H | H | F | C | G | G | 56 |
| #28 | 1st | C4-302mat-1-1-21 | L | Q | V | V | S | H | H | F | C | G | G | 57 |
| #29 | 1st | C4-302mat-1-100-23 | L | Q | V | V | S | H | H | F | C | G | G | 58 |
| #30 | 2nd | C4-302mat-2-1-40 | L | Q | V | A | S | H | H | F | C | G | G | 59 |
| #31 | 3rd | C4-302mat-3-1-2 | L | Q | V | V | S | H | H | F | C | G | R | 60 |
| #32 | 1st | C4-302mat-1-1-37 | L | R | V | V | S | H | H | F | C | G | G | 61 |
| #33 | 3rd | C4-302mat-3-1-14 | L | R | V | V | S | H | H | F | C | G | R | 62 |
| #34 | 2nd | C4-302mat-2-1-12 | L | R | V | V | S | H | H | F | C | R | R | 63 |
| #35 | 2nd | C4-302mat-2-1-24 | L | R | I | V | S | Q | H | F | C | R | R | 64 |
| #36 | 3rd | C4-302mat-3-1-8 | L | K | I | A | S | H | H | F | C | G | G | 65 |
| #37 | 2nd | C4-302mat-2-1-37 | L | L | V | A | S | H | H | F | C | G | V | 66 |
| #38 | 2nd | C4-302mat-2-100-33 | L | L | V | A | S | H | H | F | C | R | G | 67 |
| #39 | 3rd | C4-302mat-3-1-9 | L | L | V | A | S | H | H | F | C | E | R | 68 |
| #40 | 2nd | C4-302mat-2-100-24 | L | L | V | V | S | H | H | F | C | G | R | 69 |
| #41 | 3rd | C4-302mat-3-1-15 | L | L | V | V | S | R | H | F | C | G | R | 70 |
| #42 | 3rd | C4-302mat-3-1-25 | L | L | T | V | S | H | H | F | C | G | R | 71 |
| #43 | 2nd | C4-302mat-2-100-40 | L | L | V | V | S | R | H | F | C | G | R | 72 |
| #44 | 3rd | C4-302mat-3-1-11 | L | L | T | V | S | R | H | F | C | G | G | 73 |
| #45 | 3rd | C4-302mat-3-100-39 | L | L | I | V | S | H | H | F | C | G | R | 74 |

The number of binding clones obtained in each round was 5 in the 1st round, 15 in the 2nd round, and 25 in the 3rd round. It was confirmed that the number of clones with CTLA-4 binding activity increased with increasing selection pressure. Sequence analysis of these clones revealed that the leucine at position 6 (corresponding to $X_6$) of the loop portion tends to be replaced by proline, glutamine, or arginine. In particular, it was confirmed that the proline mutant tends to have high binding activity.

(5) Evaluation of Affinity after Affinity Maturation (EC50 Measurement)

For clones that showed high S/N ratio in ELISA (L6P mutants (No. #1-#25), L6Q mutant (No. #26) and L6R mutant (No. #32)), MBP fusion cyclic peptides were over-expressed in *E. coli*, subjected to affinity purification and the EC50 was measured. The results revealed that almost all clones had improved affinity compared to the original clone (Table 6). In particular, the CTLA-4 affinity of clones #19, #10 and #25 was about 50-fold improved over the original clone.

TABLE 6

| | | GlyGly | | Cys | Loop | | | | | | | | | | | | Cys | GlyGly | | EC50 | SEQ |
|---|---|---|---|---|---|---|---|---|---|---|---|---|---|---|---|---|---|---|---|---|---|
| No. | Sample name | −2 | −1 | 0 | 1 | 2 | 3 | 4 | 5 | 6 | 7 | 8 | 9 | 10 | 11 | 12 | 0 | +1 | +2 | (μM) | ID NO: |
| Original | C4-302mat-2-1-5 | G | G | C | M | H | P | F | L | L | V | V | S | H | H | F | C | G | G | 3.921 | 29 |
| #19 | C4-302mat-3-1-27 | G | G | C | M | H | P | F | L | P | I | V | S | H | H | F | C | E | R | 0.075 | 48 |
| #10 | C4-302mat-3-100-44 | G | G | C | L | H | P | F | L | P | I | V | S | H | H | F | C | G | R | 0.082 | 39 |
| #25 | C4-302mat-3-1-12 | G | G | C | M | H | P | F | L | P | V | V | S | R | H | F | C | G | R | 0.085 | 53 |
| #20 | C4-302mat-3-1-23 | G | G | C | M | H | P | F | L | P | I | A | S | L | H | F | C | G | R | 0.160 | 49 |
| #3 | C4-302mat-3-1-48 | G | G | C | M | H | P | F | L | P | V | V | S | H | H | F | C | G | A | 0.187 | 32 |
| #18 | C4-302mat-2-100-27 | G | G | C | M | H | P | F | L | P | I | V | S | H | H | F | C | G | S | 0.189 | 47 |
| #16 | C4-302mat-3-100-12 | G | G | C | M | H | P | Y | L | P | V | I | S | H | H | F | C | G | R | 0.217 | 45 |
| #6 | C4-302mat-3-1-22 | G | G | C | M | H | P | F | L | P | V | A | S | H | H | F | C | G | R | 0.222 | 35 |
| #4 | C4-302mat-3-100-37 | G | G | C | M | H | P | F | L | P | V | V | S | H | H | F | C | G | R | 0.225 | 33 |
| #5 | C4-302mat-1-1-35 | G | G | C | M | H | P | F | L | P | V | A | S | H | H | F | C | G | G | 0.288 | 34 |
| #11 | C4-302mat-3-1-45 | G | G | C | R | H | P | F | L | P | I | V | S | R | H | F | C | R | G | 0.300 | 40 |
| #21 | C4-302mat-3-1-32 | G | G | C | M | H | P | F | L | P | I | L | S | H | H | F | C | A | G | 0.322 | 50 |
| #23 | C4-302mat-3-1-31 | G | S | C | M | H | P | F | L | P | V | A | S | R | H | F | C | G | R | 0.342 | 51 |
| #7 | C4-302mat-3-100-27 | G | G | C | M | H | P | F | L | P | V | A | S | H | H | F | C | A | G | 0.352 | 36 |
| #2 | C4-302mat-2-100-18 | G | G | C | M | H | P | F | L | P | V | V | S | H | H | F | C | R | G | 0.369 | 31 |
| #8 | C4-302mat-2-1-2 | G | G | C | L | H | P | F | L | P | V | V | S | H | H | F | C | G | D | 0.474 | 37 |
| #22 | C4-302mat-3-1-35 | G | G | C | M | H | P | F | L | Q | T | V | S | H | H | F | C | G | G | 0.668 | 54 |
| #24 | C4-302mat-3-1-5 | G | G | C | M | H | P | F | L | P | V | V | S | R | H | F | C | G | G | 0.674 | 52 |
| #14 | C4-302mat-3-1-10 | G | G | C | K | H | P | Y | L | P | V | A | S | H | H | F | C | R | G | 0.703 | 43 |
| #17 | C4-302mat-2-1-3 | G | G | C | M | H | P | F | L | P | V | T | S | H | H | F | C | G | G | 0.826 | 46 |
| #13 | C4-302mat-3-100-9 | G | G | C | K | H | P | F | L | P | V | V | S | H | H | F | C | G | G | 0.832 | 42 |
| #9 | C4-302mat-2-1-38 | G | G | C | L | H | P | F | L | P | L | V | S | H | H | F | C | G | G | 0.867 | 38 |
| #12 | C4-302mat-3-100-20 | G | G | C | V | H | P | F | L | P | V | V | S | H | H | F | C | R | G | 0.889 | 41 |
| #1 | C4-302mat-1-1-24 | G | G | C | M | H | P | F | L | P | V | V | S | H | H | F | C | G | G | 1.035 | 30 |
| #32 | C4-302mat-1-1-37 | G | G | C | M | H | P | F | L | R | V | V | S | H | H | F | C | G | G | 1.493 | 61 |
| #15 | C4-302mat-2-1-27 | G | G | C | M | H | P | Y | L | P | V | I | S | H | H | F | C | G | G | 1.637 | 44 |
| #27 | C4-302mat-2-100-4 | G | G | C | M | H | P | F | L | Q | V | V | S | H | H | F | C | G | G | 4.181 | 56 |

(6) Evaluation of Inhibitory Activity after Affinity Maturation (IC50 Measurement)

For clone #19 which showed high affinity in the EC50 measurement, IC50 of the MBP fusion protein was measured using the CTLA4:B7-1[Biotinylated] Inhibitor Screening Assay Kit (BPS Bioscience). The results are shown in Table 7. The IC50 value of clone #19, whose affinity was increased by Affinity Maturation, was 1.36 μM.

TABLE 7

| Clone | GlyGly | | Cys | Loop | | | | | | | | | | | | Cys | GlyGly | | IC50 | SEQ |
|---|---|---|---|---|---|---|---|---|---|---|---|---|---|---|---|---|---|---|---|---|
| No. | −2 | −1 | 0 | 1 | 2 | 3 | 4 | 5 | 6 | 7 | 8 | 9 | 10 | 11 | 12 | 0 | +1 | +2 | (μM) | ID NO: |
| #19 | G | G | C | M | H | P | F | L | P | I | V | S | H | H | F | C | E | R | 1.36 | 48 |

(7) Measurement of Affinity and Inhibitory Activity of Synthetic Peptides

From the results shown in Table 8, it was confirmed that the inhibitory activity was maintained in the synthesized peptide (Clone No. #19) (IC50=11.5 μM).

TABLE 8

| Clone | Gly | Cys | Loop | | | | | | | | | | | | Cys | GlyGly | | IC50 | SEQ |
|---|---|---|---|---|---|---|---|---|---|---|---|---|---|---|---|---|---|---|---|
| No. | − 1 | 0 | 1 | 2 | 3 | 4 | 5 | 6 | 7 | 8 | 9 | 10 | 11 | 12 | 0 | +1 | +2 | (μM) | ID NO: |
| #19 | G | C | M | H | P | F | L | P | I | V | S | H | H | F | C | E | R | 11.50 | 26 |

From the results of affinity measurement by the BLItz system (Table 9), it was confirmed that the high binding activity to CTLA-4 protein was maintained even for the synthetic peptide, and that clone #19 had about 3-fold higher affinity than the original clone (H12SSI-Ctla4-3-02).

TABLE 9

| Clone | Biotin- | Loop | | | | | | | | | | | | | | | | ka | kd | | | SEQ ID |
|---|---|---|---|---|---|---|---|---|---|---|---|---|---|---|---|---|---|---|---|---|---|---|
| No. | Lys | 0 | 1 | 2 | 3 | 4 | 5 | 6 | 7 | 8 | 9 | 10 | 11 | 12 | 0 | +1 | +2 | (1/Ms) | (1/s) | $R^2$ | $K_D$ | NO: |
| Original | Biotin-K | C | M | H | P | F | L | L | V | V | S | H | H | F | C | | | 1.15E+05 | 2.20E−02 | 0.9782 | 1.91E−07 | 23 |
| #19 | Biotin-K | C | M | H | P | F | L | P | I | V | S | H | H | F | C | E | R | 2.08E+05 | 1.28E−02 | 0.9969 | 6.18E−08 | 24 |

Figure 5:
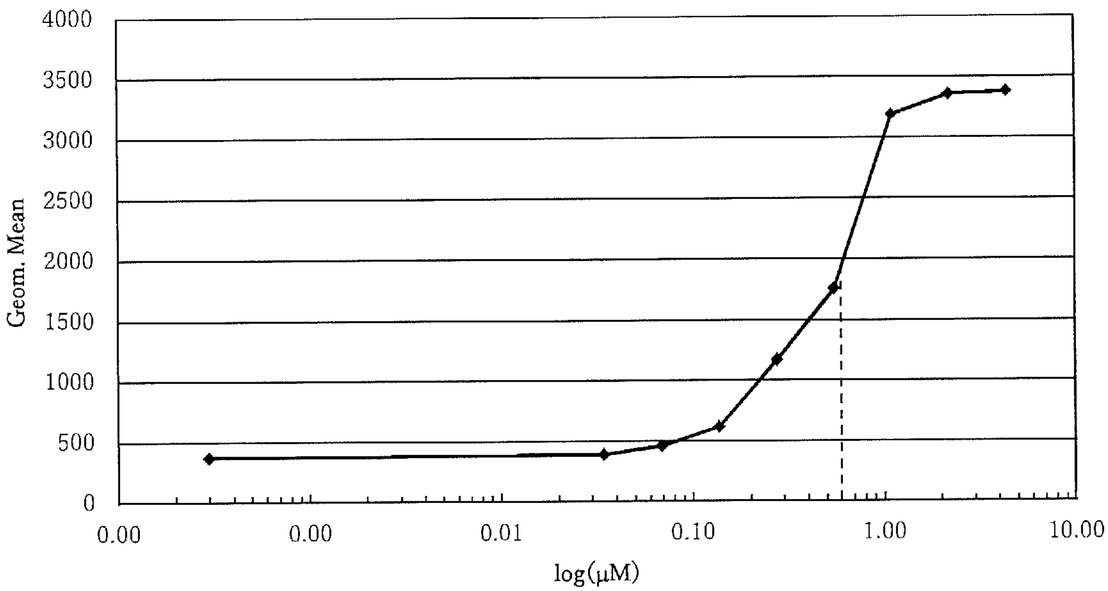
FIG. 5 The results of measured affinity of synthetic peptides to CTLA-4 expressed on the cell surface analyzed by FACS are shown.

(8) Measurement of Affinity of Synthetic Peptide for CTLA-4 Expressed on the Cell Surface FACS analysis on the cells (CHO cells) expressing CTLA-4 showed that the EC50 of No. #19 was 0.47 μM, confirming that it binds specifically to CTLA-4 with its natural structure expressed on the cell surface (FIG. 5).

Figure 6:
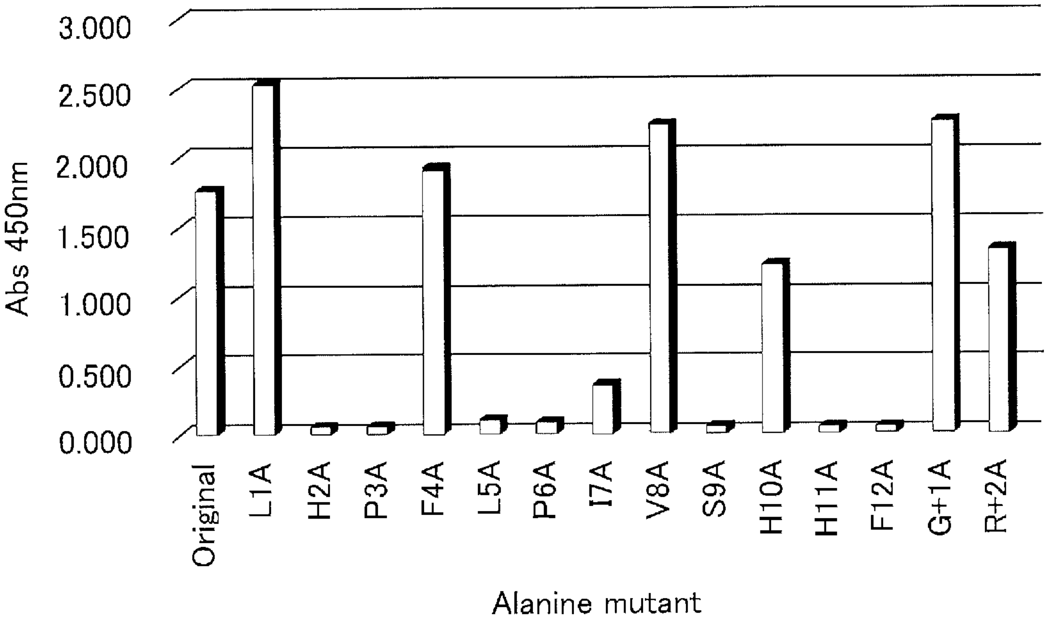
FIG. 6 The results of the alanine scanning are shown.

(9) Identification of Amino Acids Essential for CTLA-4 Binding by Canine Scanning Alanine scanning was performed on the high-affinity clone No. #10 (CLHPFLPIVSHHFCGR) (SEQ ID NO: 27) to identify amino acids essential for binding to CTLA-4 (FIG. 6). The results showed that the amino acid residues critical for binding to CTLA-4 were histidine at position 2, proline at position 3, leucine at position 5, proline at position 6, serine at position 9, histidine at position 11, and phenylalanine at position 12, with the N-terminal amino acid of the loop portion as position 1. In addition, since the I7A mutant showed weak binding activity, isoleucine at position 7 was expected to be the residue that slightly affected binding activity.

(10) Affinity Maturation by Random Library and Results of Sequence Analysis

The results of sequence of clones that showed CTLA-4 binding activity in ELISA after Affinity Maturation from a random library are shown in Table 10. Table 11 also summarizes the appearance frequency of amino acids in them.

TABLE 10

| | | | | | | Loop | | | | | | |
|---|---|---|---|---|---|---|---|---|---|---|---|---|
| | | ELISA | GlyGly | | Cys | (NNS) | H | P | (NNS) | L | P | I |
| round | Sample Name | S/N(SA) | −2 | −1 | 0 | 1 | 2 | 3 | 4 | 5 | 6 | 7 |
| 5th | C4m#19-5th4w-NN6-67 | 45.4 | G | G | C | L | H | P | F | L | P | I |
| 5th | C4m#19-5th4w-NN6-15 | 39.9 | G | G | C | L | H | P | F | L | P | I |
| 5th | C4m#19-5th4w-NN6-25 | 38.9 | G | G | C | L | H | P | V | L | P | I |
| 5th | C4m#19-5th4w-NN6-21 | 37.5 | G | G | C | W | H | P | W | L | P | I |
| 5th | C4m#19-5th4w-NN6-39 | 35.6 | G | G | C | W | H | P | F | L | P | I |

TABLE 10-continued

| | | | | | | | | | | | | |
|---|---|---|---|---|---|---|---|---|---|---|---|---|
| 5th | C4m#19-5th4w-NN6-70 | 35.5 | G | G | C | M | H | P | F | L | P | I |
| 5th | C4m#19-5th2w-NNS6-14 | 34.7 | G | G | C | W | H | P | F | L | P | I |
| 5th | C4m#19-5th4w-NN6-47 | 34.2 | G | G | C | P | H | P | W | L | P | I |
| 5th | C4m#19-5th4w-NN6-54 | 33.3 | G | G | C | L | H | P | G | L | P | I |
| 5th | C4m#19-5th4w-NN6-81 | 32.3 | G | G | C | F | H | P | Y | L | P | I |
| 5th | C4m#19-5th4w-NN6-53 | 32.2 | G | G | C | R | H | P | F | L | P | I |
| 5th | C4m#19-5th4w-NN6-34 | 32.2 | G | G | C | F | H | P | F | L | P | I |
| 5th | C4m#19-5th4w-NN6-4 | 31.6 | G | G | C | R | H | P | Y | L | P | I |
| 5th | C4m#19-5th2w-NNS6-21 | 31.1 | G | G | C | W | H | P | F | L | P | I |
| 5th | C4m#19-5th4w-NN6-20 | 30.6 | G | G | C | S | H | P | Q | L | P | I |
| 5th | C4m#19-5th4w-NN6-77 | 30.5 | G | G | C | R | H | P | F | L | P | I |
| 5th | C4m#19-5th4w-NN6-23 | 30.2 | G | G | C | R | H | P | H | L | P | I |
| 5th | C4m#19-5th4w-NN6-44 | 30.1 | G | G | C | R | H | P | F | L | P | I |
| 5th | C4m#19-5th4w-NN6-92-1 | 30.0 | G | G | C | V | H | P | F | L | P | I |
| 5th | C4m#19-5th4w-NN6-91 | 30.0 | G | G | C | M | H | P | Y | L | P | I |
| 5th | C4m#19-5th4w-NN6-19 | 29.7 | G | G | C | R | H | P | Y | L | P | I |
| 5th | C4m#19-5th4w-NN6-65-1 | 29.5 | G | G | C | W | H | P | F | L | P | I |
| 5th | C4m#19-5th4w-NN6-55-4 | 29.5 | G | G | C | V | H | P | S | L | P | I |
| 5th | C4m#19-5th2w-NNS6-22 | 29.3 | G | G | C | M | H | P | F | L | P | I |
| 5th | C4m#19-5th4w-NN6-93 | 28.9 | G | G | C | C | H | P | W | L | P | I |
| 5th | C4m#19-5th4w-NN6-9 | 28.8 | G | G | C | F | H | P | Y | L | P | I |
| 5th | C4m#19-5th4w-NN6-52 | 28.6 | G | G | C | L | H | P | F | L | P | I |
| 5th | C4m#19-5th2w-NNS6-55 | 28.3 | G | G | C | M | H | P | Y | L | P | I |
| 5th | C4m#19-5th4w-NN6-82 | 28.3 | G | G | C | F | H | P | F | L | P | I |
| 5th | C4m#19-5th4w-NN6-50 | 28.1 | G | G | C | K | H | P | V | L | P | I |
| 5th | C4m#19-5th4w-NN6-78 | 27.9 | G | G | C | W | H | P | A | L | P | I |
| 5th | C4m#19-5th4w-NN6-57 | 27.7 | G | G | C | M | H | P | Y | L | P | I |
| 5th | C4m#19-5th4w-NN6-59 | 27.6 | G | G | C | L | H | P | H | L | P | I |
| 5th | C4m#19-5th4w-NN6-24 | 27.6 | G | G | C | W | H | P | W | L | P | I |
| 5th | C4m#19-5th4w-NN6-32 | 27.2 | G | G | C | P | H | P | F | L | P | I |
| 5th | C4m#19-5th4w-NN6-56 | 27.1 | G | G | C | W | H | P | F | L | P | I |
| 5th | C4m#19-5th2w-NNS6-67 | 25.5 | G | G | C | Q | H | P | W | L | P | I |
| 5th | C4m#19-5th4w-NN6-69-1 | 24.9 | G | G | C | S | H | P | F | L | P | I |
| 5th | C4m#19-5th4w-NN6-69-3 | 24.9 | G | G | C | L | H | P | W | L | P | I |
| 5th | C4m#19-5th4w-NN6-79 | 24.9 | G | G | C | W | H | P | V | L | P | I |
| 5th | C4m#19-5th4w-NN6-68 | 24.7 | G | G | C | L | H | P | W | L | P | I |
| 4th | C4m3127-4th-NNS6-28 | 23.2 | G | G | C | L | H | P | F | L | P | I |
| 5th | C4m#19-5th4w-NN6-7 | 23.0 | G | G | C | R | H | P | F | L | P | I |
| 5th | C4m#19-5th4w-NN6-85 | 22.9 | G | G | C | W | H | P | F | L | P | I |
| 5th | C4n#19-5th2w-NNS6-71 | 22.9 | G | G | C | R | H | P | Y | L | P | I |
| 4th | C4m3127-4th-NNS6-90 | 22.9 | G | G | C | K | H | P | V | L | P | I |
| 5th | C4m#19-5th4w-NN6-37 | 22.7 | G | G | C | L | H | P | F | L | P | I |
| 5th | C4m#19-5th2w-NNS6-94 | 22.4 | G | G | C | F | H | P | Y | L | P | I |
| 5th | C4m#19-5th4w-NN6-51 | 22.1 | G | G | C | W | H | P | Y | L | P | I |
| 5th | C4m#19-5th4w-NN6-11 | 22.1 | G | G | C | R | H | P | F | L | P | I |
| 5th | C4m#19-5th4w-NN6-87 | 21.4 | G | G | C | L | H | P | V | L | P | I |
| 4th | C4m3127-4th-NNS6-87 | 21.4 | G | G | C | R | H | P | W | L | P | I |
| 5th | C4m#19-5th4w-NN6-90 | 21.2 | G | G | C | R | H | P | W | L | P | I |
| 5th | C4m#19-5th2w-NNS6-25 | 21.1 | G | G | C | K | H | P | F | L | P | I |
| 4th | C4m3127-4th-NNS6-83 | 20.7 | G | G | C | R | H | P | F | L | P | I |
| 4th | C4m3127-4th-NNS6-17 | 20.4 | G | G | C | R | H | P | V | L | P | I |
| 5th | C4m#19-5th2w-NNS6-12 | 20.4 | G | G | C | W | H | P | Y | L | P | I |
| 4th | C4m3127-4th-NNS6-72 | 20.0 | G | G | C | V | H | P | Y | L | P | I |
| 5th | C4m#19-5th2w-NNS6-90 | 19.7 | G | G | C | R | H | P | F | L | P | I |
| 5th | C4m#19-5th4w-NN6-86 | 19.7 | G | G | C | A | H | P | V | L | P | I |
| 5th | C4m#19-5th4w-NN6-58 | 18.7 | G | G | C | R | H | P | F | L | P | I |
| 5th | C4m#19-5th2w-NNS6-3 | 18.4 | G | G | C | A | H | P | F | L | P | I |
| 5th | C4m#19-5th4w-NN6-2 | 18.4 | G | G | C | W | H | P | H | L | P | I |
| 5th | C4m#19-5th4w-NN6-71 | 17.4 | G | G | C | P | H | P | W | L | P | I |
| 5th | C4m#19-5th4w-NN6-62 | 17.2 | G | G | C | Q | H | P | Y | L | P | I |
| 5th | C4m#19-5th4w-NN6-30 | 16.7 | G | G | C | W | H | P | F | L | P | I |
| 5th | C4m#19-5th4w-NN6-38 | 16.6 | G | G | C | S | H | P | F | L | P | I |
| 5th | C4m#19-5th2w-NNS6-8 | 16.5 | G | G | C | R | H | P | F | L | P | I |
| 4th | C4m3127-4th-NNS6-16 | 16.5 | G | G | C | W | H | P | Y | L | P | I |
| 5th | C4m#19-5th4w-NN6-63 | 16.5 | G | G | C | W | H | P | Y | L | P | I |
| 5th | C4m#19-5th4w-NN6-14 | 16.1 | G | G | C | W | H | P | F | L | P | I |
| 5th | C4m#19-5th4w-NN6-1 | 16.1 | G | G | C | R | H | P | Y | L | P | I |
| 5th | C4m#19-5th4w-NN6-6 | 16.1 | G | G | C | M | H | P | F | L | P | I |
| 5th | C4m#19-5th2w-NNS6-51 | 15.8 | G | G | C | R | H | P | F | L | P | I |
| 5th | C4m#19-5th4w-NN6-45 | 15.8 | G | G | C | R | H | P | W | L | P | I |
| 4th | C4m3127-4th-NNS6-12 | 15.8 | G | G | C | S | H | P | F | L | P | I |
| 5th | C4m#19-5th2w-NNS6-75 | 15.3 | G | G | C | W | H | P | W | L | P | I |
| 5th | C4m#19-5th4w-NN6-74 | 15.1 | G | G | C | F | H | P | F | L | P | I |
| 5th | C4m#19-5th4w-NN6-5-1 | 14.7 | G | G | C | W | H | P | Y | L | P | I |
| 5th | C4m#19-6th4w-NN6-5-3 | 14.7 | G | G | C | W | H | P | F | L | P | I |
| 5th | C4m#19-5th4w-NN6-46-1 | 14.2 | G | G | C | V | H | P | A | L | P | I |
| 5th | C4m#19-5th4w-NN6-64 | 13.7 | G | G | C | W | H | P | V | L | P | I |
| 4th | C4m3127-4th-NNS6-48 | 13.5 | G | G | C | F | H | P | W | L | P | I |
| 4th | C4m3127-4th-NNS6-64 | 12.9 | G | G | C | L | H | P | Y | L | P | I |
| 4th | C4m3127-4th-NNS6-80 | 12.8 | G | G | C | G | H | P | F | L | P | I |

TABLE 10-continued

| | | | | | | | | | | | | |
|---|---|---|---|---|---|---|---|---|---|---|---|---|
| 4th | C4m3127-4th-NNS6-79 | 12.8 | G | G | C | L | H | P | F | L | P | I |
| 4th | C4m3127-4th-NNS6-2 | 12.8 | G | G | C | W | H | P | S | L | P | I |
| 5th | C4m#19-5th4w-NN6-65 | 12.5 | G | G | C | W | H | P | F | L | P | I |
| 5th | C4m#19-5th4w-NN6-83 | 12.0 | G | G | C | L | H | P | L | L | P | I |
| 4th | C4m3127-4th-NNS6-60 | 11.9 | G | G | C | W | H | P | F | L | P | I |
| 5th | C4m#19-5th2w-NNS6-53 | 11.4 | G | G | C | L | H | P | W | L | P | I |
| 5th | C4m#19-5th2w-NNS6-45 | 11.0 | G | G | C | R | H | P | F | L | P | I |
| 4th | C4m3127-4th-NNS6-3 | 10.9 | G | G | C | S | H | P | F | L | P | I |
| 5th | C4m#19-5th2w-NNS6-6 | 10.3 | G | G | C | W | H | P | Y | L | P | I |
| 5th | C4m#19-5th2w-NNS6-27 | 9.9 | G | G | C | F | H | P | F | L | P | I |
| 5th | C4m#19-5th2w-NNS6-37 | 9.4 | G | G | C | I | H | P | F | L | P | I |
| 5th | C4m#19-5th2w-NNS6-33 | 9.4 | G | G | C | R | H | P | F | L | P | I |
| 5th | C4m#19-5th2w-NNS6-79 | 9.2 | G | G | C | R | H | P | F | L | P | I |
| 4th | C4m3127-4th-NNS6-85 | 9.1 | G | G | C | G | H | P | F | L | P | I |
| 5th | C4m#19-5th2w-NNS6-30 | 9.0 | G | G | C | W | H | P | F | L | P | I |
| 5th | C4m#19-5th4w-NN6-89 | 8.3 | G | G | C | M | H | P | F | L | P | I |
| 5th | C4m#19-5th2w-NNS6-86 | 7.7 | G | G | C | F | H | P | Y | L | P | I |
| 4th | C4m3127-4th-NNS6-30 | 7.5 | G | G | C | W | H | P | C | L | P | I |
| 4th | C4m3127-4th-NNS6-26 | 7.1 | G | G | C | A | H | P | A | L | P | I |
| 5th | C4m#19-5th2w-NNS6-74 | 7.0 | G | G | C | M | H | P | F | L | P | I |
| 4th | C4m3127-4th-NNS6-89 | 6.6 | G | G | C | W | H | P | F | L | P | I |
| 5th | C4m#19-5th2w-NNS6-84 | 6.4 | G | G | C | W | H | P | F | L | P | I |
| 5th | C4m#19-5th2w-NNS6-28 | 6.3 | G | G | C | A | H | P | Y | L | P | I |
| 5th | C4m#19-5th2w-NNS6-4 | 6.3 | G | G | C | F | H | P | W | L | P | I |
| 5th | C4m#19-5th2w-NNS6-46 | 6.1 | G | G | C | F | H | P | F | L | P | I |
| 5th | C4m#19-5th4w-NN6-61 | 5.9 | G | G | C | P | H | P | M | L | P | I |
| 4th | C4m3127-4th-NNS6-94 | 5.9 | G | G | C | R | H | P | V | L | P | I |
| 5th | C4m#19-5th2w-NNS6-26 | 5.8 | G | G | C | L | H | P | F | L | P | I |
| 5th | C4m#19-5th4w-NN6-36 | 5.7 | G | G | C | R | H | P | Y | L | P | I |
| 5th | C4m#19-5th4w-NN6-75 | 5.6 | G | G | C | W | H | P | F | L | P | I |
| 5th | C4m#19-5th2w-NNS6-70 | 5.1 | G | G | C | R | H | P | F | L | P | I |
| 5th | C4m#19-5th2w-NNS6-34 | 5.0 | G | G | C | C | H | P | F | L | P | I |
| 5th | C4m#19-5th4w-NN6-94 | 5.0 | G | G | C | L | H | P | F | L | P | I |
| 4th | C4m3127-4th-NNS6-66 | 4.8 | G | G | C | A | H | P | H | L | P | I |
| 5th | C4m#19-5th2w-NNS6-43 | 4.8 | G | G | C | R | H | P | F | L | P | I |
| 4th | C4m3127-4th-NNS6-7 | 4.7 | G | G | C | R | H | P | F | L | P | I |
| 5th | C4m#19-5th4w-NN6-72 | 4.6 | G | G | C | W | H | P | W | L | P | I |
| 4th | C4m3127-4th-NNS6-70 | 4.6 | G | G | C | S | H | P | Y | L | P | I |
| 5th | C4m#19-5th2w-NNS6-68 | 4.6 | G | G | C | L | H | P | W | L | P | I |
| 5th | C4m#19-5th2w-NNS6-87 | 4.5 | G | G | C | L | H | P | Y | L | P | I |
| 5th | C4m#19-5th2w-NNS6-66 | 4.4 | G | G | C | R | H | P | F | L | P | I |
| 4th | C4m3127-4th-NNS6-20 | 4.4 | G | G | C | L | H | P | F | L | P | I |
| 5th | C4m#19-5th2w-NNS6-61 | 4.3 | G | G | C | C | H | P | W | L | P | I |
| 4th | C4m3127-4th-NNS6-19 | 4.1 | G | G | C | M | H | P | S | L | P | I |
| 5th | C4m#19-5th4w-NN6-40 | 4.0 | G | G | C | F | H | P | F | L | P | I |
| 5th | C4m#19-5th4w-NN6-49 | 4.0 | G | G | C | M | H | P | Y | L | P | I |
| 5th | C4m#19-5th4w-NN6-80 | 3.8 | G | G | C | R | H | P | F | L | P | I |
| 5th | C4m#19-5th2w-NNS6-80 | 3.6 | G | G | C | L | H | P | F | L | P | I |
| 4th | C4m3127-4th-NNS6-37 | 3.5 | G | G | C | W | H | P | V | L | P | I |
| 5th | C4m#19-5th2w-NNS6-93 | 3.4 | G | G | C | F | H | P | F | L | P | I |
| 4th | C4m3127-4th-NNS6-95 | 3.4 | G | G | C | W | H | P | V | L | P | I |
| 5th | C4m#19-5th2w-NNS6-41 | 3.1 | G | G | C | W | H | P | V | L | P | I |

| | | Loop | | | | | | | | |
|---|---|---|---|---|---|---|---|---|---|---|
| round | Sample Name | (NNS) 8 | S 9 | (NNS) 10 | H 11 | F 12 | Cys 0 | (NNS) +1 | (NNS) +2 | SEQ ID NO: |
| 5th | C4m#19-5th4w-NN6-67 | R | S | V | H | F | C | P | R | 75 |
| 5th | C4m#19-5th4w-NN6-15 | R | S | V | H | F | C | P | F | 76 |
| 5th | C4m#19-5th4w-NN6-25 | R | S | R | H | F | C | P | V | 77 |
| 5th | C4m#19-5th4w-NN6-21 | L | S | P | H | F | C | P | R | 78 |
| 5th | C4m#19-5th4w-NN6-39 | R | S | L | H | F | C | P | R | 79 |
| 5th | C4m#19-5th4w-NN6-70 | R | S | M | H | F | C | P | L | 80 |
| 5th | C4m#19-5th2w-NNS6-14 | R | S | Y | H | F | C | P | W | 81 |
| 5th | C4m#19-5th4w-NN6-47 | F | S | R | H | F | C | P | V | 82 |
| 5th | C4m#19-5th4w-NN6-54 | R | S | L | H | F | C | P | R | 83 |
| 5th | C4m#19-5th4w-NN6-81 | R | S | W | H | F | C | S | R | 84 |
| 5th | C4m#19-5th4w-NN6-53 | Y | S | V | H | F | C | A | C | 85 |
| 5th | C4m#19-5th4w-NN6-34 | R | S | D | H | F | C | S | R | 86 |
| 5th | C4m#19-5th4w-NN6-4 | V | S | R | H | F | C | P | F | 87 |
| 5th | C4m#19-5th2w-NNS6-21 | R | S | S | H | F | C | P | S | 88 |
| 5th | C4m#19-5th4w-NN6-20 | L | S | D | H | F | C | S | A | 89 |
| 5th | C4m#19-5th4w-NN6-77 | V | S | T | H | F | C | S | R | 90 |
| 5th | C4m#19-5th4w-NN6-23 | W | S | W | H | F | C | G | R | 91 |
| 5th | C4m#19-5th4w-NN6-44 | V | S | W | H | F | C | G | R | 92 |
| 5th | C4m#19-5th4w-NN6-92-1 | R | S | V | H | F | C | A | L | 93 |
| 5th | C4m#19-5th4w-NN6-91 | I | S | P | H | F | C | R | G | 94 |
| 5th | C4m#19-5th4w-NN6-19 | W | S | I | H | F | C | Q | K | 95 |
| 5th | C4m#19-5th4w-NN6-65-1 | S | S | P | H | F | C | G | R | 96 |

TABLE 10-continued

| | | | | | | | | | | |
|---|---|---|---|---|---|---|---|---|---|---|
| 5th | C4m#19-5th4w-NN6-55-4 | L | S | V | H | F | C | P | R | 97 |
| 5th | C4m#19-5th2w-NNS6-22 | Q | S | V | H | F | C | S | R | 98 |
| 5th | C4m#19-5th4w-NN6-93 | V | S | T | H | F | C | G | L | 99 |
| 5th | C4m#19-5th4w-NN6-9 | R | S | W | H | F | C | G | R | 100 |
| 5th | C4m#19-5th4w-NN6-52 | R | S | V | H | F | C | G | C | 101 |
| 5th | C4m#19-5th2w-NNS6-55 | K | S | V | H | F | C | P | L | 102 |
| 5th | C4m#19-5th4w-NN6-82 | R | 5 | L | H | F | C | C | R | 103 |
| 5th | C4m#19-5th4w-NN6-50 | W | S | W | H | F | C | R | I | 104 |
| 5th | C4m#19-5th4w-NN6-78 | R | S | W | H | F | C | P | R | 105 |
| 5th | C4m#19-5th4w-NN6-57 | V | S | V | H | F | C | P | C | 106 |
| 5th | C4m#19-5th4w-NN6-59 | W | S | L | H | F | C | P | L | 107 |
| 5th | C4m#19-5th4w-NN6-24 | Y | S | H | H | F | C | P | I | 108 |
| 5th | C4m#19-5th4w-NN6-32 | W | S | V | H | F | C | P | F | 109 |
| 5th | C4m#19-5th4w-NN6-56 | Q | S | L | H | F | C | G | V | 110 |
| 5th | C4m#19-5th2w-NNS6-67 | S | S | W | H | F | C | P | R | 111 |
| 5th | C4m#19-5th4w-NN6-69-1 | L | S | V | H | F | C | P | F | 112 |
| 5th | C4m#19-5th4w-NN6-69-3 | V | S | V | H | F | C | A | R | 113 |
| 5th | C4m#19-5th4w-NN6-79 | R | S | C | H | F | C | A | V | 114 |
| 5th | C4m#19-5th4w-NN6-68 | R | S | R | H | F | C | S | R | 115 |
| 4th | C4m3127-4th-NNS6-28 | F | S | S | H | F | C | A | L | 116 |
| 5th | C4m#19-5th4w-NN6-7 | W | S | W | H | F | C | P | F | 117 |
| 5th | C4m#19-5th4w-NN6-85 | F | S | V | H | F | C | G | C | 118 |
| 5th | C4n#19-5th2w-NNS6-71 | A | S | P | H | F | C | P | G | 119 |
| 4th | C4m3127-4th-NNS6-90 | V | S | L | H | F | C | P | W | 120 |
| 5th | C4m#19-5th4w-NN6-37 | S | S | W | H | F | C | G | R | 121 |
| 5th | C4m#19-5th2w-NNS6-94 | S | S | V | H | F | C | G | R | 122 |
| 5th | C4m#19-5th4w-NN6-51 | V | S | W | H | F | C | S | R | 123 |
| 5th | C4m#19-5th4w-NN6-11 | W | S | H | H | F | C | V | C | 124 |
| 5th | C4m#19-5th4w-NN6-87 | R | S | F | H | F | C | W | R | 125 |
| 4th | C4m3127-4th-NNS6-87 | V | S | W | H | F | C | S | R | 126 |
| 5th | C4m#19-5th4w-NN6-90 | V | S | Y | H | F | C | S | S | 127 |
| 5th | C4m#19-5th2w-NNS6-25 | S | S | H | H | F | C | P | Y | 128 |
| 4th | C4m3127-4th-NNS6-83 | F | S | K | H | F | C | E | L | 129 |
| 4th | C4m3127-4th-NNS6-17 | V | S | L | H | F | C | P | G | 130 |
| 5th | C4m#19-5th2w-NNS6-12 | R | S | V | H | F | C | G | R | 131 |
| 4th | C4m3127-4th-NNS6-72 | S | S | I | H | F | C | S | M | 132 |
| 5th | C4m#19-5th2w-NNS6-90 | V | S | F | H | F | C | P | F | 133 |
| 5th | C4m#19-5th4w-NN6-86 | R | S | L | H | F | C | P | H | 134 |
| 5th | C4m#19-5th4w-NN6-58 | S | S | I | H | F | C | C | I | 135 |
| 5th | C4m#19-5th2w-NNS6-3 | F | S | P | H | F | C | P | F | 136 |
| 5th | C4m#19-5th4w-NN6-2 | V | S | S | H | F | C | L | F | 137 |
| 5th | C4m#19-5th4w-NN6-71 | A | S | V | H | F | C | P | F | 138 |
| 5th | C4m#19-5th4w-NN6-62 | W | S | F | H | F | C | P | F | 139 |
| 5th | C4m#19-5th4w-NN6-30 | M | S | F | H | F | C | P | Y | 140 |
| 5th | C4m#19-5th4w-NN6-38 | F | S | L | H | F | C | P | V | 141 |
| 5th | C4m#19-5th2w-NNS6-8 | F | S | L | H | F | C | A | R | 142 |
| 4th | C4m3127-4th-NNS6-16 | F | S | V | H | F | C | P | R | 143 |
| 5th | C4m#19-5th4w-NN6-63 | L | S | R | H | F | C | Q | A | 144 |
| 5th | C4m#19-5th4w-NN6-14 | R | S | V | H | F | C | C | R | 145 |
| 5th | C4m#19-5th4w-NN6-1 | F | S | A | H | F | C | R | S | 146 |
| 5th | C4m#19-5th4w-NN6-6 | K | S | S | H | F | C | R | K | 147 |
| 5th | C4m#19-5th2w-NNS6-51 | V | S | L | H | F | C | P | F | 148 |
| 5th | C4m#19-5th4w-NN6-45 | W | S | V | H | F | C | G | V | 149 |
| 4th | C4m3127-4th-NNS6-12 | R | S | R | H | F | C | P | F | 150 |
| 5th | C4m#19-5th2w-NNS6-75 | K | S | P | H | F | C | A | L | 151 |
| 5th | C4m#19-5th4w-NN6-74 | Y | S | W | H | F | C | A | R | 152 |
| 5th | C4m#19-5th4w-NN6-5-1 | Q | S | L | H | F | C | P | F | 153 |
| 5th | C4m#19-6th4w-NN6-5-3 | L | S | L | H | F | C | G | W | 154 |
| 5th | C4m#19-5th4w-NN6-46-1 | W | S | F | H | F | C | P | S | 155 |
| 5th | C4m#19-5th4w-NN6-64 | R | S | V | H | F | C | C | R | 156 |
| 4th | C4m3127-4th-NNS6-48 | A | S | W | H | F | C | G | R | 157 |
| 4th | C4m3127-4th-NNS6-64 | V | S | S | H | F | C | P | F | 158 |
| 4th | C4m3127-4th-NNS6-80 | F | S | L | H | F | C | P | R | 159 |
| 4th | C4m3127-4th-NNS6-79 | R | S | V | H | F | C | L | R | 160 |
| 4th | C4m3127-4th-NNS6-2 | Y | S | P | H | F | C | P | L | 161 |
| 5th | C4m#19-5th4w-NN6-65 | L | S | L | H | F | C | S | R | 162 |
| 5th | C4m#19-5th4w-NN6-83 | L | S | V | H | F | C | P | S | 163 |
| 4th | C4m3127-4th-NNS6-60 | S | S | W | H | F | C | G | L | 164 |
| 5th | C4m#19-5th2w-NNS6-53 | R | S | F | H | F | C | G | A | 165 |
| 5th | C4m#19-5th2w-NNS6-45 | W | S | V | H | F | C | W | R | 166 |
| 4th | C4m3127-4th-NNS6-3 | W | S | V | H | F | C | G | Q | 167 |
| 5th | C4m#19-5th2w-NNS6-6 | L | S | L | H | F | C | Q | R | 168 |
| 5th | C4m#19-5th2w-NNS6-27 | R | S | C | H | F | C | A | R | 169 |
| 5th | C4m#19-5th2w-NNS6-37 | W | S | I | H | F | C | S | R | 170 |
| 5th | C4m#19-5th2w-NNS6-33 | W | S | F | H | F | C | W | G | 171 |
| 5th | C4m#19-5th2w-NNS6-79 | V | S | R | H | F | C | V | A | 172 |
| 4th | C4m3127-4th-NNS6-85 | F | S | S | H | F | C | P | L | 173 |
| 5th | C4m#19-5th2w-NNS6-30 | L | S | W | H | F | C | G | R | 174 |
| 5th | C4m#19-5th4w-NN6-89 | I | S | Q | H | F | C | A | F | 175 |
| 5th | C4m#19-5th2w-NNS6-86 | W | S | L | H | F | C | R | S | 176 |

TABLE 10-continued

| | | | | | | | | | | |
|---|---|---|---|---|---|---|---|---|---|---|
| 4th | C4m3127-4th-NNS6-30 | L | S | P | H | F | C | P | R | 177 |
| 4th | C4m3127-4th-NNS6-26 | W | S | C | H | F | C | P | F | 178 |
| 5th | C4m#19-5th2w-NNS6-74 | R | S | W | H | F | C | S | R | 179 |
| 4th | C4m3127-4th-NNS6-89 | F | S | A | H | F | C | M | R | 180 |
| 5th | C4m#19-5th2w-NNS6-84 | V | S | F | H | F | C | P | F | 181 |
| 5th | C4m#19-5th2w-NNS6-28 | R | S | V | H | F | C | P | C | 182 |
| 5th | C4m#19-5th2w-NNS6-4 | S | S | L | H | F | C | P | F | 183 |
| 5th | C4m#19-5th2w-NNS6-46 | F | S | Y | H | F | C | G | L | 184 |
| 5th | C4m#19-5th4w-NN6-61 | F | S | V | H | F | C | P | Y | 185 |
| 4th | C4m3127-4th-NNS6-94 | W | S | S | H | F | C | P | W | 186 |
| 5th | C4m#19-5th2w-NNS6-26 | V | S | I | H | F | C | S | A | 187 |
| 5th | C4m#19-5th4w-NN6-36 | W | S | A | H | F | C | C | R | 188 |
| 5th | C4m#19-5th4w-NN6-75 | K | S | V | H | F | C | C | A | 189 |
| 5th | C4m#19-5th2w-NNS6-70 | V | S | W | H | F | C | A | A | 190 |
| 5th | C4m#19-5th2w-NNS6-34 | Y | S | V | H | F | C | A | S | 191 |
| 5th | C4m#19-5th4w-NN6-94 | Y | S | L | H | F | C | P | C | 192 |
| 4th | C4m3127-4th-NNS6-66 | R | S | V | H | F | C | S | F | 193 |
| 5th | C4m#19-5th2w-NNS6-43 | W | S | S | H | F | C | A | A | 194 |
| 4th | C4m3127-4th-NNS6-7 | R | S | P | H | F | C | G | S | 195 |
| 5th | C4m#19-5th4w-NN6-72 | V | S | V | H | F | C | G | C | 196 |
| 4th | C4m3127-4th-NNS6-70 | H | S | R | H | F | C | L | S | 197 |
| 5th | C4m#19-5th2w-NNS6-68 | V | S | C | H | F | C | P | R | 198 |
| 5th | C4m#19-5th2w-NNS6-87 | F | S | V | H | F | C | A | L | 199 |
| 5th | C4m#19-5th2w-NNS6-66 | F | S | V | H | F | C | P | F | 200 |
| 4th | C4m3127-4th-NNS6-20 | L | S | L | H | F | C | P | F | 201 |
| 5th | C4m#19-5th2w-NNS6-61 | R | S | V | H | F | C | P | F | 202 |
| 4th | C4m3127-4th-NNS6-19 | W | S | W | H | F | C | P | H | 203 |
| 5th | C4m#19-5th4w-NN6-40 | R | S | H | H | F | C | M | L | 204 |
| 5th | C4m#19-5th4w-NN6-49 | R | S | F | H | F | C | S | C | 205 |
| 5th | C4m#19-5th4w-NN6-80 | F | S | W | H | F | C | A | V | 206 |
| 5th | C4m#19-5th2w-NNS6-80 | V | S | W | H | F | C | P | C | 207 |
| 4th | C4m3127-4th-NNS6-37 | R | S | I | H | F | C | G | C | 208 |
| 5th | C4m#19-5th2w-NNS6-93 | Q | S | R | H | F | C | C | R | 209 |
| 4th | C4m3127-4th-NNS6-95 | R | S | G | H | F | C | S | R | 210 |
| 5th | C4m#19-5th2w-NNS6-41 | R | S | D | H | F | C | C | R | 211 |

TABLE 11

| | Apparance frequency of amino acids | | | | | | | | | | | | | | | Usage | Usage frequency/codon | Codon |
|---|---|---|---|---|---|---|---|---|---|---|---|---|---|---|---|---|---|---|
| #19 | M | H | P | F | L | P | I | V | S | H | H | F | C | E | R | frequency | numbers | numbers |
| W | 34 | | | 18 | | | | 21 | | 22 | | | | 3 | 5 | 103 | 103.00 | 1 |
| F | 14 | | | 68 | | | | 17 | | 9 | | | | 0 | 22 | 130 | 65.00 | 2 |
| Y | 0 | | | 27 | | | | 6 | | 3 | | | | 0 | 3 | 39 | 19.50 | 2 |
| V | 4 | | | 13 | | | | 24 | | 33 | | | | 2 | 7 | 83 | 20.75 | 4 |
| L | 21 | | | 1 | | | | 12 | | 21 | | | | 3 | 14 | 72 | 12.00 | 6 |
| I | 1 | | | 0 | | | | 2 | | 7 | | | | 0 | 3 | 13 | 4.33 | 3 |
| M | 10 | | | 1 | | | | 1 | | 1 | | | | 2 | 1 | 16 | 16.00 | 1 |
| P | 4 | | | 0 | | | | 0 | | 9 | | | | 57 | 0 | 70 | 17.50 | 4 |
| A | 5 | | | 3 | | | | 3 | | 3 | | | | 16 | 9 | 39 | 9.75 | 4 |
| G | 2 | | | 1 | | | | 0 | | 1 | | | | 22 | 4 | 30 | 7.50 | 4 |
| S | 6 | | | 3 | | | | 9 | | 8 | | | | 18 | 9 | 53 | 8.83 | 6 |
| T | 0 | | | 0 | | | | 0 | | 2 | | | | 0 | 0 | 2 | 0.50 | 4 |
| N | 0 | | | 0 | | | | 0 | | 0 | | | | 0 | 0 | 0 | 0.00 | 2 |
| Q | 2 | | | 1 | | | | 4 | | 1 | | | | 4 | 1 | 13 | 6.50 | 2 |
| D | 0 | | | 0 | | | | 0 | | 3 | | | | 0 | 0 | 3 | 1.50 | 2 |
| E | 0 | | | 0 | | | | 0 | | 0 | | | | 1 | 0 | 1 | 0.50 | 2 |
| K | 4 | | | 0 | | | | 4 | | 1 | | | | 0 | 3 | 12 | 6.00 | 2 |
| R | 31 | | | 0 | | | | 37 | | 9 | | | | 5 | 47 | 129 | 21.50 | 6 |
| H | 0 | | | 4 | | | | 1 | | 4 | | | | 0 | 2 | 11 | 5.50 | 2 |
| C | 3 | | | 1 | | | | 0 | | 4 | | | | 8 | 11 | 27 | 13.50 | 2 |

As a result, all amino acids except asparagine were used at positions 1, 4, 8, 10, +1 and +2 (corresponding to $X_1$, $X_4$, $X_8$, $X_{10}$, $X_{+1}$ and $X_{+2}$), and mutations at these positions were expected to have little effect on the presence or absence of binding activity. It was also observed that hydrophobic amino acids (especially aromatic amino acids) and amino acids with long side chains tend to appear more frequently, while hydrophilic amino acids with short side chains tend to appear less frequently. This was expected to be caused by the fact that hydrophobic bonds have been added due to the mutation to hydrophobic amino acids with long side chains, and the molecular structure of the peptide has been stabilized more tightly.

INDUSTRIAL APPLICABILITY

According to the present invention, a cyclic peptide which inhibits CTLA-4 function is provided. The cyclic peptide of the present invention is useful as an immune checkpoint inhibitor and expected to be applied for a prophylactic or therapeutic drug against diseases (e.g., cancer) which can be treated or prevented by inhibiting CTLA-4 function.

This application is based on a patent application No. 2019-185266 filed in Japan (filing date: Oct. 8, 2019), the contents of which are incorporated in full herein.

The invention claimed is:

1. A cyclic peptide having a cyclic structure formed by an intrapeptide bond between two amino acids in the peptide, which comprises the amino acid sequence represented by formula (I):

$X_1$-His-Pro-$X_4$-Leu-$X_6$-$X_7$-$X_8$-Ser-$X_{10}$-His-Phe (I) (SEQ ID NO: 212)

in the cyclic structure and has an activity to specifically bind to human CTLA-4, wherein $X_1$, $X_4$, $X_6$, $X_7$, $X_8$ and $X_{10}$ are each independently any amino acid.

2. The cyclic peptide according to claim 1, wherein the cyclic peptide comprises the amino acid sequence represented by formula (II):

$X_0$-$X_1$-His-Pro-$X_4$-Leu-$X_6$-$X_7$-$X_8$-Ser-$X_{10}$-His-Phe-$X_{00}$ (II) (SEQ ID NO: 213)

wherein $X_0$ and $X_{00}$ are each independently any amino acid, and wherein the peptide is cyclized by an intramolecular bond between $X_0$ and $X_{00}$.

3. The cyclic peptide according to claim 2, wherein the cyclic peptide comprises the amino acid sequence represented by formula (III):

$(Y)m$-$X_0$-$X_1$-His-Pro-$X_4$-Leu-$X_6$-$X_7$-$X_8$-Ser-$X_{10}$-His-Phe-$X_{00}$-$(Z)n$ (III) (SEQ ID NO: 214)

wherein (Y)m is an amino acid sequence having a length of m amino acid(s), (Z)n is an amino acid sequence having a length of n amino acid(s), m is any integer selected from the group consisting of 0, 1 and 2, and n is any integer selected from the group consisting of 0, 1 and 2.

4. The cyclic peptide according to claim 2, wherein $X_0$ and $X_{00}$ are each independently an amino acid having a side chain containing a thiol group.

5. The cyclic peptide according to claim 4, wherein $X_0$ is Cys, and $X_{00}$ is Cys.

6. The cyclic peptide according to claim 4, wherein the peptide is cyclized by an intramolecular disulfide bond between a thiol group in the side chain of $X_0$ and a thiol group in the side chain of $X_{00}$.

7. The cyclic peptide according to claim 1, wherein $X_6$ is Leu, Pro, Gln, Lys or Arg, and $X_7$ is Val, Leu, Ile or Thr.

8. The cyclic peptide according to claim 7, wherein $X_6$ is Pro, and $X_7$ is Ile.

9. The cyclic peptide according to claim 3, wherein n is 2, (Z)n consists of an amino acid sequence represented by $X_{+1}$-$X_{+2}$, and $X_{+1}$ and $X_{+2}$ are each independently any amino acid.

10. The cyclic peptide according to claim 3, wherein m is 2, (Y)m consists of an amino acid sequence represented by $X_{-2}$-$X_{-1}$, and $X_{-2}$ and $X_{-1}$ are each independently any amino acid.

11. The cyclic peptide according to claim 10, wherein $X_{-2}$ is Gly, and $X_{-1}$ is Gly, Ser or Asp.

12. The cyclic peptide according to claim 1, wherein the amino acid sequence represented by formula (I) consists of (1a) an amino acid sequence from the position 4 to position 15 in the amino acid sequence represented by any of SEQ ID NOs: 30-211, or (2a) an amino acid sequence having a substitution at least at one amino acid corresponding to one selected from $X_1$, $X_4$, $X_6$, $X_7$, $X_8$ and $X_{10}$ in an amino acid sequence from the position 4 to position 15 in the amino acid sequence represented by any of SEQ ID NOs: 30-211.

13. The cyclic peptide according to claim 2, wherein the amino acid sequence represented by formula (II) consists of (1b) an amino acid sequence from position 3 to position 16 in the amino acid sequence represented by any of SEQ ID NOs: 30-211, or (2b) an amino acid sequence having a substitution at least at one amino acid corresponding to one selected from $X_1$, $X_4$, $X_6$, $X_7$, $X_8$ and $X_{10}$ in an amino acid sequence from position 3 to position 16 in the amino acid sequence represented by any of SEQ ID NOs: 30-211.

14. The cyclic peptide according to claim 3, wherein the amino acid sequence represented by formula (III) consists of (1c) the amino acid sequence represented by any of SEQ ID NOs: 30-211, or (2c) an amino acid sequence having a substitution at least at one amino acid corresponding to one selected from X-2, X-1, $X_1$, $X_4$, $X_6$, $X_7$, $X_8$, $X_{10}$, $X_{+1}$ and $X_{+2}$ in the amino acid sequence represented by any of SEQ ID NOs: 30-211.

15. A pharmaceutical composition which comprises the cyclic peptide according to claim 1 and a pharmaceutically acceptable carrier or excipient.

16. A method for treating a tumor in a subject, which comprises administering an effective amount of the cyclic peptide according to claim 1 to the subject, wherein the tumor is selected from the group consisting of malignant lymphoma, colorectal cancer, non-small cell lung cancer, ovarian cancer, renal cancer, prostate cancer, and malignant melanoma.

* * * * *